(12) United States Patent
Spetzler et al.

(10) Patent No.: US 9,409,966 B2
(45) Date of Patent: *Aug. 9, 2016

(54) GLUCAGON-LIKE PEPTIDE-1 DERIVATIVES AND THEIR PHARMACEUTICAL USE

(71) Applicant: Novo Nordisk A/S, Bagsvaerd (DK)

(72) Inventors: Jane Spetzler, Broenshoej (DK); Lauge Schaeffer, Lyngby (DK); Jesper Lau, Farum (DK); Thomas Kruse, Herlev (DK); Patrick W. Garibay, Holte (DK); Steffen Reedtz-Runge, Frederiksberg (DK); Henning Thoegersen, Farum (DK); Ingrid Pettersson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 143 days.

This patent is subject to a terminal disclaimer.

(21) Appl. No.: 14/506,052

(22) Filed: Oct. 3, 2014

(65) Prior Publication Data

US 2015/0025003 A1 Jan. 22, 2015

Related U.S. Application Data

(63) Continuation of application No. 12/676,451, filed as application No. PCT/EP2008/061755 on Sep. 5, 2008, now Pat. No. 8,895,694.

(60) Provisional application No. 60/971,930, filed on Sep. 13, 2007, provisional application No. 61/024,345, filed on Jan. 29, 2008.

(30) Foreign Application Priority Data

Sep. 5, 2007 (EP) .................................... 07115746
Jan. 28, 2008 (EP) .................................... 08101008

(51) Int. Cl.
*C07K 14/605* (2006.01)
*A61K 38/26* (2006.01)

(52) U.S. Cl.
CPC .............. *C07K 14/605* (2013.01); *A61K 38/26* (2013.01)

(58) Field of Classification Search
None
See application file for complete search history.

(56) References Cited

U.S. PATENT DOCUMENTS

| | | | |
|---|---|---|---|
| 5,968,899 | A | 10/1999 | Sekine et al. |
| 6,268,343 | B1 | 7/2001 | Knudsen et al. |
| 6,458,924 | B2 | 10/2002 | Knudsen et al. |
| 7,235,627 | B2 | 6/2007 | Knudson et al. |
| 7,271,149 | B2 | 9/2007 | Glaesner et al. |
| 8,097,698 | B2 | 1/2012 | Knudsen et al. |
| 8,895,694 | B2 | 11/2014 | Spetzler et al. |
| 2001/0011071 | A1 | 8/2001 | Knudsen et al. |
| 2007/0203058 | A1 | 8/2007 | Lau et al. |

FOREIGN PATENT DOCUMENTS

| | | |
|---|---|---|
| EP | 1364967 A2 | 11/2003 |
| JP | 05-506427 | 9/1993 |
| JP | 2001-504105 A | 3/2001 |
| JP | 2006-520818 A | 9/2006 |
| WO | 96/29342 | 9/1996 |
| WO | 9808871 A1 | 3/1998 |
| WO | 99/43708 A1 | 9/1999 |
| WO | 00/34331 | 6/2000 |
| WO | 00/69911 | 11/2000 |
| WO | 01/04156 | 1/2001 |
| WO | 02/46227 A2 | 6/2002 |
| WO | 03/011892 A2 | 2/2003 |
| WO | 2005/027978 A2 | 3/2005 |
| WO | 2005/058954 A1 | 6/2005 |
| WO | 2006/005667 A2 | 1/2006 |
| WO | 2006/037810 | 4/2006 |
| WO | 2006/097535 A2 | 9/2006 |
| WO | 2006/097536 A2 | 9/2006 |
| WO | 2006/097537 A2 | 9/2006 |
| WO | 2006/097538 | 9/2006 |

OTHER PUBLICATIONS

Runge et al., "Crystal Structure of the Ligand-Bound Glucagon-Like Peptide-1 Receptor Extracellular Domain," J Biol Chem 2008, vol. 283, No. 17, pp. 11340-11347.
Adelhorst, K et al Journal of Biological Chemistry Structure Activity Studies of GLP-1 1994 269 9 6275-6278.
Knudsen, L.B. Journal of Medicinal Chemistry Glucagon-Like Peptide-1: The Basis of a New Class of Treatment for Type 2 Diabetes 2004 47 17 4128-4134.
Leger et al., "Identification of CJC-1131-Albumin Bioconjugate as a Stable and Bioactive GLP-1 (7-36) Analog," Bioorganic and Medicinal Chemistry Letters, vol. 14, pp. 4395-4398 (2004).
Pan, 2006 Journal of Biological Chemistry vol. 281 pp. 12506-12515.
The Medical Dictionary Online. http://cancerweb.ncl.ac.uklomd/about.html. 2005.
Nauck, M A. Regulatory Peptides. "Glucagon-Like Peptide 1 and its Derivatives in the Treatment od Diabetes." 2005. vol. 128(2). pp. 135-148.
David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.

*Primary Examiner* — Amber D Steele
*Assistant Examiner* — Schuyler Milton
(74) *Attorney, Agent, or Firm* — Richard W. Bork

(57) ABSTRACT

The invention relates to protracted Glucagon-Like Peptide-1 (GLP-1) derivatives and therapeutic uses thereof. The GLP-1 derivative of the invention comprises a modified GLP-1(7-37) sequence having a total of 2-12 amino acid modifications, including Glu22 and Arg26, and being derivatised with an albumin binding residue or pegylated in position 18, 20, 23, 30, 31, 34, 36, 37, or 39. These compounds are useful in the treatment or prevention of diabetes type 2 and related diseases. The compounds are potent, stable, have long half-lives, a high affinity of binding to albumin, and/or a high affinity of binding to the extracellular domain of the GLP-1 receptor (GLP-1R), all of which is of potential relevance for the overall aim of achieving long-acting, stable and active GLP-1 derivatives with a potential for once weekly administration.

22 Claims, No Drawings

GLUCAGON-LIKE PEPTIDE-1 DERIVATIVES AND THEIR PHARMACEUTICAL USE

CROSS-REFERENCE TO RELATED APPLICATIONS

This application is a Continuation of U.S. application Ser. No. 12/676,451, filed Oct. 13, 2010, which is a 35 U.S.C. §371 national stage application of International Patent Application PCT/EP2008/061755 (published as WO 2009/030738), filed Sep. 5, 2008, which claimed priority of European Patent Applications 07115746.5, filed Sep. 5, 2007 and 08101008.4, filed Jan. 28, 2008; this application further claims priority under 35 U.S.C. §119 of U.S. Provisional Applications 60/971,930, filed Sep. 13, 2007 and 61/024,345, filed Jan. 29, 2008, the contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 4, 2010, is named 7668204US_SeqList-.txt and is 5,582 bytes in size.

FIELD OF THE INVENTION

This invention relates to the field of therapeutic peptides, i.e. to new protracted peptide derivatives of Glucagon-Like Peptide-1 (GLP-1).

BACKGROUND OF THE INVENTION

A range of different approaches have been used for modifying the structure of GLP-1 compounds in order to provide a longer duration of action in vivo.

WO 2006/097535 discloses various peptide agonists of the glucagon family with secretin like activity and their therapeutic use. GLP-1(7-37) derivatives comprising a modified GLP-1(7-37) sequence are disclosed in Examples 3 and 5 thereof. These derivatives, however, do not have a Glu residue at position 22 and an Arg residue at position 26.

WO 01/04156 discloses peptides that lower blood glucose levels. Compounds 4, 5, 6, 7, 10, 11, 12, and 13 thereof are GLP-1 derivatives, however none of these compounds have a Glu residue at position 22 and an Arg residue at position 26.

EP 1364967 discloses glucagon-like insulinotropic peptides, compositions and methods. None of the five GLP-1 compositions of Example 1 thereof comprises a modified GLP-1 sequence having Glu at position 22 and Arg at position 26.

WO 98/08871 discloses protracted GLP-1 derivatives including liraglutide, which is a GLP-1 derivative for once daily administration developed by Novo Nordisk A/S. Liraglutide is expected to be marketed for the treatment of type 2 diabetes as of 2009. Liraglutide does not have Glu at position 22 and Arg at position 26. The derivative disclosed in Example 30 of this reference does, but is not derivatised in position 18, 20, 23, 30, 31, 34, 36, 37, or 39.

WO 2005/027978 discloses novel GLP-1 derivatives including three which comprise a modified GLP-1(7-37) sequence having a Glu at position 22 and an Arg at position 26. These derivatives, however, are not derivatised in position 18, 20, 23, 30, 31, 34, 36, 37, or 39.

Runge et al (Journal of Biological Chemistry, vol. 283, no. 17, pp. 11340-11347), which was published after the priority dates of the present invention, discloses the crystal structure of the extracellular domain of the ligand-bound GLP-1 receptor.

Many diabetes patients particularly in the type 2 diabetes segment are subject to so-called "needle-phobia", i.e. a substantial fear of injecting themselves. In the type 2 diabetes segment most patients are treated with oral hypoglycaemic agents, and since GLP-1 compounds are expected to be an injectable pharmaceutical product these patients will be administered, the fear of injections may become a serious obstacle for the widespread use of the clinically very promising compounds. Thus, there is a need to develop new compounds which can be administered less than once daily, e.g. once every second or third day preferably once weekly, while retaining an acceptable clinical profile or optionally via non invasive administration such as pulmonary, nasal, sublingual, bucal or oral administration.

One object of the present invention is to provide a chemically, physically and enzymatically stable GLP-1 derivative, preferably with a high alpha-helical content.

A further object of the invention is to provide a long acting, i.e. having an administration regimen as described above, GLP-1 derivative.

Another object of this invention is to provide a GLP-1 derivative with high potency (receptor affinity) in order to reduce the therapeutic dose used for example for once weekly s.c. dosing or alternatively for non-invasive delivery.

Another object of this invention is to provide a GLP-1 derivative with a high binding affinity to the extracellular domain of the GLP-1 receptor (GLP-1R).

Another object of this invention is to provide a GLP-1 derivative with high albumin binding affinity which protects the peptide for proteolytic degradation and reduce renal clearance of the peptide.

Potency, stability, half-life, binding affinity to albumin, and binding affinity to the extracellular domain of the GLP-1 receptor are properties of potential relevance for an overall object of achieving long-acting, stable and of course therapeutically active GLP-1 derivatives with a potential for once weekly administration.

SUMMARY OF THE INVENTION

In one aspect of the invention, a GLP-1 derivative is provided which comprises a modified GLP-1(7-37) sequence having: i) a total of 2-12 amino acid modifications as compared to GLP-1(7-37) (SEQ ID No: 1), including a) a Glu residue at a position equivalent to position 22 of GLP-1(7-37), and b) an Arg residue at a position equivalent to position 26 of GLP-1(7-37); and ii) which is derivatised with an albumin binding residue or pegylated in a position selected from a position equivalent to position 18, 20, 23, 30, 31, 34, 36, 37, or 39 of GLP-1(7-37).

In a further aspect, pharmaceutical compositions and methods and uses of the derivatives according to the invention, are provided.

DESCRIPTION OF THE INVENTION

Definitions and Preferred Embodiments

In the present specification, the following terms have the indicated meaning:

The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The 22 proteogenic amino acids are: Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus a non-proteogenic amino acid (which may also be designated a non-natural amino acid) is a moiety which can be incorporated into a peptide via peptide bonds but is not a proteogenic amino acid. Examples are γ-carboxyglutamate, ornithine, phosphoserine, the D-amino acids such as D-alanine and D-glutamine, Synthetic non-proteogenic amino acids comprising amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), 3-aminomethyl benzoic acid, anthranilic acid, des-amino-histidine (abbreviated DesaminoHis, alternative name imidazopropionic acid, abbreviated Impr), the beta analogs of amino acids such as β-alanine etc., D-histidine, 2-amino-histidine, β-hydroxy-histidine, homohistidine, $N^\alpha$-acetyl-histidine, α-fluoromethyl-histidine, α-methyl-histidine, α,α-dimethyl-glutamic acid, m-$CF_3$-phenylalanine (abbreviated m-$CF_3$-Phe), α,β-diaminopropionic acid (abbreviated Dap), 3-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid.

The term "analogue" as used herein referring to a polypeptide means a modified peptide wherein one or more amino acid residues of the peptide have been substituted by other amino acid residues and/or wherein one acid amino residue has been deleted from the peptide in the C-terminal of the peptide or wherein one amino acid residue has been added to the C-terminal of the peptide.

The term "modified peptide" as used herein refers to a modified peptide as defined above. For the present purposes this term is used interchangeably with the term "modified peptide sequence". Consistently herewith, the term "modification" when used herein in connection with peptide sequences refers to amino acid substitutions, additions, and/or deletions.

For the present purposes any amino acid substitution, deletion, and/or addition refers to the sequence of human GLP-1 (7-37) which is included herein as SEQ ID No: 1. However, the numbering of the amino acid residues in the sequence listing always starts with no. 1, whereas for the present purpose we want, following the established practice in the art, to start with amino acid residue no. 7 and assign number 7 to it. Therefore, generally, any reference herein to a position number of the GLP-1(7-37) sequence is to the sequence starting with His at position 7 and ending with Gly at position 37.

A simple system is often used to describe analogues: For example [$Arg^{34}$]GLP-1(7-37)Lys designates a GLP-1(7-37) analogue wherein the naturally occurring lysine at position 34 has been substituted with arginine and wherein a lysine has been added to the C-terminal amino acid residue, i.e. to the $Gly^{37}$. This GLP-1 analogue accordingly has two amino acid modifications as compared to GLP-1(7-37), viz. one substitution and one addition.

The expression "a position equivalent to" when used herein to characterize a modified GLP-1(7-37) sequence refers to the corresponding position in the natural GLP-1(7-37) sequence (having the sequence of SEQ ID No: 1). Corresponding positions are easily deduced, e.g. by simple handwriting and eyeballing. In the alternative, a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM50 and the default identity matrix may be used, and the penalty for the first residue in a gap may be set at −12 and the penalties for additional residues in a gap at −2.

As another example, the GLP-1 derivative of Example 1 herein comprises the following modified GLP-1(7-37) sequence: [desaminoHis7,Glu22,Arg26,Arg34,Lys37]GLP-1(7-37)amide, which has a total of 5 amino acid modifications (in this case all substitutions), including a Glu at a position equivalent to position 22 of GLP-1(7-37), and an Arg at a position equivalent to position 26 of GLP-1(7-37).

All amino acids for which the optical isomer is not stated is to be understood to mean the L-isomer.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like.

The GLP-1 derivatives of the invention are derivatised with an albumin binding residue or pegylated in a position selected from position 18, 20, 23, 30, 31, 34, 36, 37, or 39. The derivatisation refers to a covalent link as explained above.

For example a lysine residue or cysteine residue may be linked to an albumin binding residue via a chemical bond. Such a chemical bond can as an example be obtained by derivatisation of an epsilon amino group of lysine by acylation with an active ester of an albumin binding residue such as a long fatty acid.

An example of a GLP-1 derivative of the invention (a derivative of an analogue of GLP-1(7-37)) is N-epsilon37{2-[2-(2-{2-[2-((R)-3-carboxy-3-{[1-(19-carboxynonadecanoyl)piperidine-4-carbon yl]amino}propionylamino) ethoxy]ethoxy}acetylamino)ethoxy]ethoxy}acetyl [desaminoHis7,Glu22,Arg26,Arg34,Lys37]GLP-1(7-37) amide (the compound of Example 1 herein). In this compound, the naturally occurring Gly in position 37 has been substituted with lysine which has been derivatised at N-epsilon37 with the following albumin binding residue: {2-[2-(2-{2-[2-((R)-3-carboxy-3-{[1-(19-carboxynonadecanoyl)piperidine-4-carbon yl]amino}propionylamino) ethoxy]ethoxy}acetylamino)ethoxy]ethoxy}acetyl (structure 1)

Structure 1

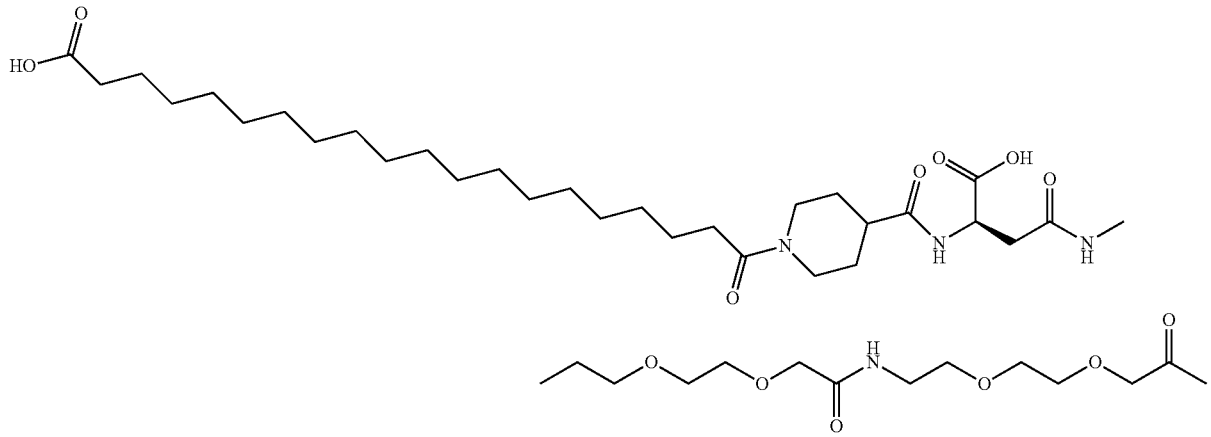

and wherein the naturally occurring histidine in position 7 has been substituted with desaminoHis and the naturally occuring glycine in pos 22 has been substituted with glutamate and lysine in position 26 and 34 has been substituted with arginine. In this derivative, the GLP-1(7-37) analogue of [desaminoHis7,Glu22,Arg26,Arg34,Lys37]GLP-1(7-37)amide has been derivatised (covalently modified with an amide bond) with an albumin binding residue in a position equivalent to position 37 of GLP-1(7-37), viz. at the epsilon amino group of Lys at position 37. Accordingly, a GLP-1 derivative is a compound with two constituents: A GLP-1 peptide part and a derivative part which are covalently linked to each other.

The amino acid residue which is derivatised may comprise an amino group. Examples of amino acid residues comprising an amino group is lysine, ornithine, Epsilon-N-alkylated lysine such as Epsilon-N methylLysine, O-aminoethylserine, O-aminopropylserine or longer O alkylated serines containing a primary or secondary amino group in the side chain. In a further aspect of the invention, the derivatised amino acid residue comprises a primary amino group in a side chain. Examples of amino acid residues comprising a primary amino group is lysine ornithine, O-aminoethylserine, O-aminopropylserine or longer O alkylated serines containing a primary amino group in the side chain. In yet a further aspect of the invention, the derivatised amino acid residue is lysine. In yet a further aspect of the invention, the derivative according to the invention is only derivatised in one position, e.g. only one amino acid residue is derivatised.

Other examples of connecting two chemical moieties as used in the present invention includes but is not limited to alkylation, ester formation, amide formation or maleimide coupling.

The term "GLP-1 peptide" as used herein means GLP-1(7-37) (SEQ ID No: 1) or a GLP-1(7-37) analogue thereof.

The term "GLP-1(7-37)" is intended to include GLP-1(7-37) (i.e. the peptide), as well as the corresponding amide(s), and the same applies to GLP-1(7-37) analogues.

In a particular embodiment, the GLP-1 derivative of the invention is an amide. In another particular embodiment it is a peptide, i.e. the GLP-1 peptide moiety of the derivative has a free carboxylic group at the C-terminus.

The terms "GLP-1(7-34)", "GLP-1(7-35)", "GLP-1(7-36)", "GLP-1(7-38)", "GLP-1(7-39)", "GLP-1(7-40)", "GLP-1(7-41)" or derivative thereof is now and then used herein to specify the exact length of the GLP-1 peptide moiety of a derivative of the invention. For example, "a GLP-1(7-34) derivative" refers to a GLP-1(7-37) derivative in which the last three C-terminal amino acid residues have been deleted. As another example, "a GLP-1(7-39) derivative" refers to a GLP-1(7-37) derivative in which two amino acid residues have been added to the C-terminus.

In a preferred embodiment, the GLP-1 derivative of the invention has the sequence of formula (I):

Formula (I)
(SEQ ID No: 2)
Xaa$_7$-Xaa$_8$-Xaa$_9$-Gly-Thr-Phe-Thr-Ser-Asp-Xaa$_{16}$-Ser- Xaa$_{18}$-Tyr-Xaa$_{20}$-Glu-Glu-Xaa$_{23}$-Xaa$_{24}$-Xaa$_{25}$-Arg-Xaa$_{27}$-

Xaa$_{28}$-Ile-Xaa$_{30}$-Xaa$_{31}$-Leu-Xaa$_{33}$-Xaa$_{34}$-Xaa$_{35}$-Xaa$_{36}$-

Xaa$_{37}$-Xaa$_{38}$-Xaa$_{39}$-Xaa$_{40}$-Xaa$_{41}$-R wherein
(Xaa$_7$-Xaa$_8$) is (L-histidine-Aib), (desamino-histidine-alanine), or (desamino-histidine-Aib);
Xaa$_9$ is Glu, or a Glu derivative;
Xaa$_{16}$ is Val, or Leu;
Xaa$_{18}$ is Ser, Lys, Cys, or Arg;
Xaa$_{20}$ is Leu, or Lys;
Xaa$_{23}$ is Gln, Glu, Lys, Cys, or Arg;
Xaa$_{24}$ is Ala, or Asn;
Xaa$_{25}$ is Ala, or Val;
Xaa$_{27}$ is Glu, Ala, or Leu;
Xaa$_{28}$ is Phe, or a Phe derivative;
Xaa$_{30}$ is Ala, Glu, Lys, or Arg;
Xaa$_{31}$ is Trp, Cys, or Lys;
Xaa$_{33}$ is Val, Cys, or Lys;
Xaa$_{34}$ is Lys, Cys, Glu, Asn, Dap, or Arg;
Xaa$_{35}$ is Gly, Arg, Lys, Aib, or absent;
Xaa$_{36}$ is Arg, Lys, or absent;
Xaa$_{37}$ is Gly, Aib, Cys, Lys, epsilon-amino-Lys, Pro, Arg, or absent;
Xaa$_{38}$ is Lys, Glu, Arg, or absent;
Xaa$_{39}$ is Lys, Arg, or absent;
Xaa$_{40}$ is Arg, or absent;
Xaa$_{41}$ is Arg, or absent; and
R is amide, or absent;
provided that if Xaa$_{37}$, Xaa$_{38}$, Xaa$_{39}$, or Xaa$_{40}$ is absent, then each amino acid residue downstream is also absent;

and which is derivatised with an albumin binding residue or pegylated in a position selected from a position equivalent to position 18, 20, 23, 30, 31, 34, 36, 37, or 39 of GLP-1(7-37) (SEQ ID No: 1).

A non-limiting example of a "Glu derivative" is alpha, alpha dimethyl-Glu.

A non-limiting example of "a Phe derivative" is $CF_3$-Phe, such as m-$CF_3$-Phe (see e.g. the compound of Example 3).

The term epsilon-amino-Lys (or epsilon-Lys) is intended to indicate that amino acid residue no. 38, lysine, is bound to the GLP-1(7-37) peptide via its epsilon amino group, not (as is usually the case) via its alpha amino group (see e.g. the compound of Example 28).

In another preferred embodiment, the GLP-1 derivative of the invention has the sequence of formula (II):

```
Formula (II)
                                            (SEQ ID No: 3)
Xaa7-Xaa8-Glu-Gly-Thr-Phe-Thr-Ser-Asp-Val-Ser- Xaa18-Tyr-Leu-Glu-Glu-Gln-Ala-Ala-Arg-Glu- Phe-Ile-Xaa30-Xaa31-Leu-Xaa33-Xaa34-Xaa35-Xaa36-

Xaa37-Xaa38-Xaa39-Xaa40-Xaa41-R
``` wherein
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine, or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{18}$ is Ser, Lys, or Arg;
$Xaa_{30}$ is Ala, Glu, Lys, or Arg;
$Xaa_{31}$ is Lys, or Trp;
$Xaa_{33}$ is Val, or Lys;
$Xaa_{34}$ is Lys, Glu, Dap, or Arg;
$Xaa_{35}$ is Gly, Arg, Lys, Aib, or absent;
$Xaa_{36}$ is Arg, Lys, or absent;
$Xaa_{37}$ is Gly, Aib, Lys, epsilon-amino-Lys, Pro, Arg, or absent;
$Xaa_{38}$ is Lys, Glu, Arg, or absent;
$Xaa_{39}$ is Lys, Arg, or absent;
$Xaa_{40}$ is Arg, or absent;
$Xaa_{41}$ is Arg, or absent; and
R is amide, or is absent;
provided that if $Xaa_{37}$, $Xaa_{38}$, $Xaa_{39}$, or $Xaa_{40}$ is absent, then each amino acid residue downstream is also absent;
and which is derivatised with an albumin binding residue or pegylated in a position selected from a position equivalent to position 18, 20, 23, 30, 31, 34, 36, 37, or 39 of GLP-1(7-37) (SEQ ID No: 1).

The term "linker" as used herein means a spacer (the two terms spacer and linker is used interchangeably in the present specification) that separates a peptide and an albumin binding residue or a polyethylene glycol polymer.

The term "pharmaceutically acceptable" as used herein means suited for normal pharmaceutical applications, i.e. giving rise to no serious adverse events in patients etc.

The term "excipient" as used herein means the chemical compounds which are normally added to pharmaceutical compositions, e.g. buffers, tonicity agents, preservatives and the like.

The term "effective amount" as used herein means a dosage which is sufficient to be effective for the treatment of the patient compared with no treatment.

The term "pharmaceutical composition" as used herein means a product comprising an active derivative according to the invention, or a pharmaceutically acceptable salt, amide, alkyl, ester, or the like thereof, together with pharmaceutical excipients such as buffer, preservative, and optionally a tonicity modifier and/or a stabilizer. Thus a pharmaceutical composition is also known in the art as a pharmaceutical formulation.

The term "treatment of a disease" as used herein means the management and care of a patient having developed the disease, condition or disorder. The purpose of treatment is to combat the disease, condition or disorder. Treatment includes the administration of the active derivative according to the invention to eliminate or control the disease, condition or disorder as well as to alleviate the symptoms or complications associated with the disease, condition or disorder.

In one aspect of the invention, the linker comprises one or more alkylene glycol units, such as 1 to 5 alkylene glycol units. The alkylene glycol units are in a further aspect ethylene glycol, propylene glycol or butylene glycol but can also be higher alkylene glycols.

In another aspect of the invention, the linker is a hydrophilic linker selected from
—$(CH_2)_l D[(CH_2)_n E]_m(CH_2)_p$-$Q_q$-, wherein
l, m and n independently are 1-20 and p is 0-10,
Q is —Z—$(CH_2)_l D[(CH_2)_n G]_m(CH_2)_p$—,
q is an integer in the range from 0 to 5,
each D, E, and G are independently selected from —O—, —$NR^3$—, —N($COR^4$)—, —$PR^5$(O)—, and —P($OR^6$)(O)—, wherein $R^3$, $R^4$, $R^5$, and $R^6$ independently represent hydrogen or $C_{1-6}$-alkyl,
Z is selected from —C(O)NH—, —C(O)NHCH$_2$—, —OC(O)NH—, —C(O)NHCH$_2$CH$_2$—, —C(O)CH$_2$—, —C(O)CH=CH—, —C(H$_2$)$_s$—, —C(O)—, —C(O)O— or —NHC(O)—, wherein s is 0 or 1.

In another aspect of the invention, the linker is a hydrophilic linker as defined above wherein l is 1 or 2, n and m are independently 1-10 and p is 0-10.

In another aspect of the invention, the linker is a hydrophilic linker as defined above wherein D is —O—.

In another aspect of the invention, the linker is a hydrophilic linker as defined above wherein E is —O—.

In yet another aspect of the invention, the hydrophilic linker is
—$CH_2O[(CH_2)_2O]_m(CH_2)_p Q_q$-, wherein m is 1-10, p is 1-3, and Q is —Z—$CH_2O[(CH_2)_2O]_m(CH_2)_p$— wherein Z is as defined above.

In another aspect of the invention, the linker is a hydrophilic linker as defined above wherein q is 1.

In another aspect of the invention, the linker is a hydrophilic linker as defined above wherein G is —O—.

In another aspect of the invention, the linker is a hydrophilic linker as defined above wherein Z is selected from the group consisting of —C(O)NH—, —C(O)NHCH$_2$—, and —OC(O)NH—.

In another aspect of the invention, the linker is a hydrophilic linker as defined above wherein q is 0.

In another aspect of the invention, the linker is a hydrophilic linker as defined above wherein l is 2.

In another aspect of the invention, the linker is a hydrophilic linker as defined above wherein n is 2.

In one aspect of this invention a "hydrophilic linker" is used that separates a peptide and an albumin binding residue with a chemical moiety.

In one aspect of this invention, the hydrophilic linker is
—C(O)—(CH$_2$)$_l$—O—[(CH$_2$CH$_2$—O]$_m$—(CH$_2$)$_p$—[NHC(O)—(CH$_2$)$_l$—O—[(CH$_2$)$_n$—O]$_m$—(CH$_2$)$_p$]$_q$—NH—,
wherein l, m, n, and p independently are 1-5, and q is 0-5.

In yet another aspect of this invention, the hydrophilic linker is
—C(O)—CH$_2$—O—CH$_2$CH$_2$—O—CH$_2$CH$_2$ [NHC(O)—CH$_2$—O—CH$_2$CH$_2$O—CH$_2$CH$_2$]$_q$—NH—,
wherein q is 0-5.

In yet another aspect of this invention, the hydrophilic linker is
—C(O)—CH$_2$—O—CH$_2$CH$_2$—O—CH$_2$CH$_2$—NHC(O)—CH$_2$—O—CH$_2$CH$_2$O—CH$_2$CH$_2$—NH—.

In yet another aspect of the invention, the hydrophilic linker is —[CH$_2$CH$_2$O]$_{m+1}$(CH$_2$)$_p$Q$_q$-
wherein m and p independently is 0-10, and
Q is —Z—(CH$_2$)$_l$D[(CH$_2$)$_n$G]$_m$(CH$_2$)$_p$— as defined above.

In yet another aspect of the invention, the hydrophilic linker is —(CH$_2$)$_l$—O—[(CH$_2$)$_n$—O]$_m$—(CH$_2$)$_p$—[C(O)NH—(CH$_2$)$_l$—O—[(CH$_2$)$_n$—O]$_m$—(CH$_2$)$_p$]$_q$—,
wherein l, m, n, and p independently are 1-5, and q is 0-5.

In a further aspect of the invention, the linker comprises an amino acid residue except Cys, or a dipeptide such as Gly-Lys. In the present text, the expression "a dipeptide such as Gly-Lys" is used to designate a dipeptide wherein the C-terminal amino acid residue is Lys, His or Trp, preferably Lys, and wherein the N-terminal amino acid residue is selected from the group comprising Ala, Arg, Asp, Asn, Gly, Glu, Gln, Ile, Leu, Val, Phe and Pro.]

Suitable PEG polymers are typically commercially available or may be made by techniques well-known to those skilled in the art.

In one aspect of the invention, the GLP-1 derivative has been pegylated.

In a particular embodiment, the PEG polymer has a molecular weight of greater than 700D, in a further embodiments a molecular weight greater than 5 kD, greater than 10 kD, and greater that 20 kD. The PEG polymer may be linear or branched. In cases where the PEG polymer is greater than 20 KDa, the PEG polymer is preferable having a branched structure, such as for example, a 43 kD branched PEG-peptide (Shearwater 2001 catalog #2D3XOT01, mPEG2-MAL).

The attachment of a PEG on an intact peptide can be accomplished by attaching the PEG on the opposite side of the peptide surface that interacts with the receptor.

There are several strategies for coupling PEG to peptides (see, e.g. Veronese, Biomaterials 22:405-417, 2001), all of which are incorporated herein by reference in their entirety. Those skilled in the art, will therefore be able to utilize well-known techniques for linking the PEG polymer to GLP-1 peptides described herein.

Briefly, cysteine PEGylation is one method for site-specific PEGylation, and can be accomplished by introducing a unique cysteine mutation at one of the specific positions on human amylin or the amylin analog and then reacting the resulting peptide with a cysteine-specific PEGylation reagent, such as PEG-maleimide. It may be necessary to mutate the peptide in order to allow for site-specific PEGylation. For example, if the peptide contains cysteine residues, these will need to be substituted with conservative amino acids in order to ensure site-specific PEGylation. In addition, rigid linkers, including but not limited to "GGS", "GGSGGS", and "PPPS" may be added to the C-terminus, but before the site of PEG attachment (i.e. a unique cysteine residue).

In another aspect, the GLP-1 derivative according to the invention has been derivatised with an albumin binding residue.

In one embodiment, the albumin binding residue is a lipophilic residue. In a further embodiment, the lipophilic residue is attached to a lysine residue optionally via a linker by conjugation chemistry such as by alkylation, acylation, ester formation, or amide formation or to a cysteine residue by maleimide coupling.

In a further embodiment of the invention, the albumin binding residue is negatively charged at physiological pH. In another aspect of the invention, the albumin binding residue comprises a group which can be negatively charged. One preferred group which can be negatively charged is a carboxylic acid group.

In yet another embodiment of the invention, the albumin binding residue is selected from the group consisting of a straight chain alkyl group, a branched alkyl group, a group which has an ω-carboxylic acid group, and a partially or completely hydrogenated cyclopentanophenanthrene skeleton.

In a further embodiment of the invention, the albumin binding residue is a cibacronyl residue.

In a further embodiment of the invention, the albumin binding residue has from 6 to 40 carbon atoms, from 8 to 26 carbon atoms or from 8 to 20 carbon atoms.

In a further embodiment of the invention, the albumin binding residue is an acyl group selected from the group comprising CH$_3$(CH$_2$)$_r$CO—, wherein r is an integer from 4 to 38, preferably an integer from 4 to 24, more preferred selected from the group comprising CH$_3$(CH$_2$)$_6$CO—, CH$_3$(CH$_2$)$_8$CO—, CH$_3$(CH$_2$)$_{10}$CO—, CH$_3$(CH$_2$)$_{12}$CO—, CH$_3$(CH$_2$)$_{14}$CO—, CH$_3$(CH$_2$)$_{16}$CO—, CH$_3$(CH$_2$)$_{18}$CO—, CH$_3$(CH$_2$)$_{20}$CO— and CH$_3$(CH$_2$)$_{22}$CO—.

In another embodiment of the invention, the albumin binding residue is an acyl group of a straight-chain or branched alkane α,ω-dicarboxylic acid.

In another particular embodiment, the GLP-1 derivative according to the invention comprises a hydrophilic spacer between the modified GLP-1 sequence and one or more albumin binding residue(s).

The hydrophilic spacer may bean unbranched oligo ethylene glycol moiety with appropriate functional groups at both terminals that forms a bridge between an amino group of the modified GLP-1 sequence and a functional group of the albumin binding residue.

Preferred embodiments of the GLP-1 derivatives of the invention, compositions including them, and methods of using them are listed in the sections headed "Embodiments according to the invention", "Additional embodiments according to the invention", and "Further particular embodiments according to the invention" close to the start of the experimental part of the present application.

Functional Properties

A number of GLP-1 derivatives of the invention have been synthesized and tested as described in the experimental part.

The GLP-1 derivatives of the invention have several advantageous and beneficial properties as explained in the following, by reference to the Examples.

In a first aspect, the GLP-1 derivative of the invention has a protracted profile of action, which makes it potentially suitable for less-frequently-than-once-daily administration, preferably with a potential for once-weekly, or even less frequent, administration. The profile of action can be evaluated in pharmacokinetic experiments with laboratory animals such as mice or pigs. Suitable experiments are found in Example 39 (minipigs) and Example 43 (mice) of the present application.

As described in minipig Example 39, (i) the GLP-1 derivative may be administered s.c. or i.v., preferably s.c.; (ii) the pigs are preferably Göttingen minipigs, preferably about 5 months old and weighing 8-10 kg; (iii) the animals are preferably fasting before administration, preferably as described; (iv) the injection is preferably given as indicated; (v) the number of animals tested is preferably as indicated; (vi) the dosage is preferably as indicated; and/or (vii) blood samples are also preferably taken, collected, and assayed as indicated in this Example.

Pharmacokinetic experiments like the one in Example 39 result in a plasma concentration profile of the compound in question versus time, on the basis of which the half-life, T½, may be determined, preferably as described in Example 39.

In a first particular embodiment, the half-life of the GLP-1 derivative of the invention, after s.c. administration in minipigs, is above 18 hours, preferably above 24 hours, more preferably above 28 hours, even more preferably above 30 hours, most preferably above 32 hours.

In a second particular embodiment, the half-life of the GLP-1 derivative of the invention, after s.c. administration in minipigs, is above 32 hours, preferably above 34 hours, more preferably above 36 hours, even more preferably above 38 hours, most preferably above 40 hours.

In a third particular embodiment, the half-life of the GLP-1 derivative of the invention, after s.c. administration in minipigs, is above 45 hours, preferably above 50 hours, more preferably above 55 hours, even more preferably above 60 hours, most preferably above 65 hours.

In a fourth particular embodiment, the half-life of the GLP-1 derivative of the invention, after s.c. administration in minipigs, is above 45 hours, preferably above 50 hours, more preferably above 55 hours, even more preferably above 60 hours, most preferably above 65 hours.

In a fifth particular embodiment, the half-life of the GLP-1 derivative of the invention, after s.c. administration in minipigs, is above 70 hours, preferably above 75 hours, more preferably above 80 hours, even more preferably above 85 hours, most preferably above 90 hours.

In a sixth particular embodiment, the half-life of the GLP-1 derivative of the invention, after s.c. administration in minipigs, is above 92 hours, preferably above 94 hours, more preferably above 96 hours, even more preferably above 98 hours, most preferably above 100 hours.

In a seventh particular embodiment, the GLP-1 derivative of the invention has an in vivo half-life of at least 50 hrs after s.c. administration to mini pigs, and preferably an in vivo half-life of at least 80 hrs after s.c. administration to mini pigs.

Accordingly, exemplary half-life intervals (time indicated in hours, h) of the GLP-1 derivative of the invention, determined in minipigs by s.c. administration, are: 20-100, 30-100, 40-100, 50-100, 60-100, 70-100, 80-100, or 90-100 (hours).

The half-life of the GLP-1 derivative of the invention may also be determined in a dose-response study in db/db mice, e.g. as described in Example 43. As described in this Example, (i) the mice are preferably from Taconic; (ii) of 10-12 weeks of age; (iii) have free access to standard feed such as Altromin 1324 and tap water; (iv) are kept at 24 dgC; (v) being acclimatised for 1 week; (vi) allocated into 7 groups (preferably n=6) based on matching mean blood glucose values; (vii) receive treatment as described in the example; (viii) being dosed as described; (ix) blood glucose is assessed according to a scheme as described, preferably assayed as described; and/or (x) the half-life determined based on the blood glucose vs. time determinations, preferably as described in the example.

In a first particular embodiment, the half-life of the GLP-1 derivative of the invention, after s.c. administration in db/db mice, is above 10 hours, preferably above 11 hours, more preferably above 12 hours, even more preferably above 13 hours, most preferably above 14 hours.

In a second particular embodiment, the half-life of the GLP-1 derivative of the invention, after s.c. administration in db/db mice, is above 15 hours, preferably above 16 hours, more preferably above 17 hours, even more preferably above 18 hours, most preferably above 19 hours.

In a third particular embodiment, the half-life of the GLP-1 derivative of the invention, after s.c. administration in db/db mice, is above 20 hours, preferably above 21 hours, more preferably above 22 hours, even more preferably above 23 hours, most preferably above 24 hours.

In a fourth particular embodiment, the half-life of the GLP-1 derivative of the invention, after s.c. administration in db/db mice, is above 25 hours, preferably above 26 hours, more preferably above 27 hours, even more preferably above 28 hours, most preferably above 29 hours.

Accordingly, exemplary half-life intervals (time indicated in hours, h) of the GLP-1 derivative of the invention, assayed in db/db mice by s.c. administration, are: 5-30, 10-30, 15-30, 20-30, or 25-30 (hours).

In a fifth particular embodiment, the present invention relates to a derivative of a GLP-1 peptide which has substantially improved terminal half-life in rodent and in a non-rodent model relative to liraglutide. The terminal half-life in rodent or in a non-rodent model is preferably improved at least 3 fold relative to liraglutide. Alternatively, the terminal half-life in a non-rodent model is improved at least 6 fold relative to liraglutide, or the GLP-1 derivative of the invention has an in vivo half-life of at least 10 hrs after i.v. administration to rats.

In a second aspect, the GLP-1 derivative of the invention has an improved stability. In particular, it has a secondary structure with a significant alpha-helical stretch. Secondary structures with significant alpha-helical stretch are expected to confer chemical, physical and/or enzymatical stability to the molecule in question.

The alpha-helix content may be determined using circular dichroism (CD) spectroscopy, e.g. as described in Example 44. In particular embodiments, (i) far-UV CD spectra are recorded on 5 uM solutions of the compound in question, preferably in 10 mM Tris/ClO$_4$ pH 8.0; (ii) buffer background is subtracted; (iii) the data are normalised to molar elipticity $M^{-1}$ $cm^{-1}$ based on the concentration of peptide bonds; (iv) the intensity value (delta epsilon) at 222 nm is extracted; (v) the alpha-helical content is calculated based on the intensity value of (iv), assuming proportionality and using for conversion the fact that an intensity value of $-1$ $M^{-1}$ $cm^{-1}$ corresponds to 10% alpha-helical structure.

In a first particular embodiment, the GLP-1 derivative of the invention has an alpha-helix content of above 20%, preferably above 25%, more preferably above 30%, even more preferably above 35%, and most preferably above 36%.

In a second particular embodiment, the GLP-1 derivative of the invention has an alpha-helix content of above 40%, preferably above 45%, more preferably above 50%, even more preferably above 55%, and most preferably above 58%.

Accordingly, exemplary ranges of alpha-helix content of GLP-1 derivatives of the invention are 20-60, 30-60, 40-60, and 50-60(%).

In a third particular embodiment the GLP-1 derivative of the invention is stable against the chemical degradation normally seen with exendin-4—especially oxidation and deamidation.

In a fourth particular embodiment, the GLP-1 derivative of the invention is chemically and physically stable at neutral pH, most preferably in the range 6-8.

In a fifth particular embodiment, the GLP-1 derivative of the invention has little or no tendency to aggregate. The aggregation tendency is preferably significantly improved relatively to the aggregation tendency of liraglutide when tested in a thioflavin assay.

In a third aspect, the GLP-1 derivative of the invention has an acceptable, preferably a high potency (at the receptor). The potency of an insulinotropic agent such as the GLP-1 derivative of the invention may be determined by calculating the $EC_{50}$ value from the dose-response curve as described in Example 40.

The term "insulinotropic agent" as used herein means a derivative which is an agonist of the human GLP-1 receptor, i.e. a derivative which stimulates the formation of cAMP in a suitable medium containing the human GLP-1 receptor (one such medium disclosed below).

In particular embodiments, (i) baby hamster kidney (BHK) cells expressing the cloned human GLP-1 receptor are used, preferably BHK-467-12A, more preferably BHK-467-12A (tk-ts13); (ii) the cells are grown in DMEM media with the addition of 100 IU/mL penicillin, 100 pg/mL streptomycin (1% Pen/Strep), 5% fetal calf serum (FCS) and 0.5 mg/mL Geneticin G-418 (Life Technologies), preferably at 5% $CO_2$; (iii) the cells, preferably at approximately 80% confluence, are washed twice in phosphate buffered saline (PBS); (iv) the cells are harvested with an aqueous solution of the tetrasodium salt of ethylenediaminetetraacetic acid, such as Versene; (v) plasma membranes are prepared from the cells by homogenisation, preferably in buffer 1; (vi) the homogenate is centrifuged, e.g. at 48,000×g for 15 min at 4° C.; and/or (vii) the pellet is suspended by homogenization in buffer 2; Steps (vi) and (viii) are preferably repeated, e.g. one or two times more.

The functional receptor assay may be carried out as described in Example 40 by measuring cyclic AMP (cAMP) as a response to stimulation by the insulinotropic agent. cAMP formed is preferably quantified by the AlphaScreen™ cAMP Kit (Perkin Elmer Life Sciences). Incubations may be carried out in half-area 96-well microtiter plates in a total volume of 50 µL buffer 3 (50 mM Tris-HCl, 5 mM HEPES, 10 mM $MgCl_2$, pH 7.4) and with the following additions: 1 mM ATP, 1 µM GTP, 0.5 mM 3-isobutyl-1-methylxanthine (IBMX), 0.01% Tween-20, 0.1% BSA, 6 µg membrane preparation, 15 µg/mL acceptor beads, 20 µg/mL donor beads preincubated with 6 nM biotinyl-cAMP. Derivatives to be tested for agonist activity are preferably dissolved and diluted in buffer 3. GTP is freshly prepared for each experiment. The plate is incubated in the dark with slow agitation for three hours at room temperature followed by counting in the Fusion™ instrument (Perkin Elmer Life Sciences). Concentration-response curves are plotted for the individual derivatives and $EC_{50}$ values estimated using a four-parameter logistic model with Prism, preferably in version 4.0, or 5.0, (GraphPad, Carlsbad, Calif.).

In a first particular embodiment, the GLP-1 derivative of the invention has a potency ($EC_{50}$ in nM), as determined using the cAMP assay, below 4.00, preferably below 3.50, more preferably below 3.00, even more preferably below 2.50, and most preferably below 2.00 (nM).

In a second particular embodiment, the GLP-1 derivative of the invention has a potency ($EC_{50}$ in nM), as determined using the cAMP assay, below 1.80, preferably below 1.60, more preferably below 1.40, even more preferably below 1.20, and most preferably below 1.00 (nM).

In a third particular embodiment, the GLP-1 derivative of the invention has a potency ($EC_{50}$ in nM), as determined using the cAMP assay, below 0.80, preferably below 0.60, more preferably below 0.40, even more preferably below 0.20, and most preferably below 0.10 (nM).

In a fourth particular embodiment, the GLP-1 derivative of the invention has a potency ($EC_{50}$ in nM), as determined using the cAMP assay, below 0.090, preferably below 0.080, more preferably below 0.070, even more preferably below 0.060, and most preferably below 0.050 (nM).

In a fifth particular embodiment, the GLP-1 derivative of the invention has a potency ($EC_{50}$ in nM), as determined using the cAMP assay, below 0.040, preferably below 0.030, more preferably below 0.020, and most preferably below 0.010 (nM).

Accordingly, exemplary ranges of potency ($EC_{50}$ in nM, as determined using the cAMP assay) of GLP-1 derivatives of the invention are 0.010-2.00, 0.010-1.80, 0.010-1.60, 0.010-1.40, 0.010-1.20, 0.010-1.00, 0.010-0.80, 0.010-0.60, 0.010-0.40, 0.010-0.30, 0.010-0.20, 0.010-0.10, and 0.010-0.90 (nM), preferably 0.010-0.40, 0.010-0.30, 0.010-0.20, 0.010-0.10, and 0.010-0.90 (nM).

In a sixth particular embodiment, for very strong albumin binding analogues with albumin binding affinity below 100 nM, the GLP-1 potency is better than 3 micro molar and preferable the potency is better than 1 micromolar in the cAMP assay. For strong albumin binding derivatives with albumin binding affinity below 500 nM, the GLP-1 potency is better than 1 micro molar and preferable the potency is better than 0.2 micromolar in the cAMP assay.

In a seventh particular embodiment, the GLP-1 derivative of the invention can bind to albumin and the GLP-1 receptor simultaneously. For example, the GLP-1 derivative of the invention may bind to the GLP-1 receptor with an affinity below 100 nM, preferable below 30 nM in the presence of 2% albumin.

The GLP-1 derivative of the invention may also have an affinity to the GLP-1 receptor which is only partly decreased when comparing the affinity in the presence of very low concentration (e.g. 0.005% to 0.2%) of human albumin to the affinity in the presence of 2% human albumin. The shift in binding affinity under these conditions is preferably less than 50 fold, more preferably below 30 fold and most preferably below 10 fold.

In a fourth aspect, the GLP-1 derivative of the invention has a high albumin binding affinity. The albumin refers to human serum albumin (HSA), and the affinity may be determined as described in Example 41.

The affinities of the GLP-1 derivatives for human serum albumin (HSA) may be measured by a competition scintillation proximity assay (SPA), preferably by (i) incubating streptavidin-SPA beads (such as GE Healthcare RPNQ0009) with biotinylated HSA, e.g. for 5 hours; (ii) washing the beads with buffer; (iii) mixing the beads mixed with an $^{125}$I-labeled acylated GLP-1 analogue, such as N-epsilon26-[2-(2-{2-[2-(2-{2-[(S)-4-Carboxy-4-(17-carboxyheptadecanoylamino) butyrylamino]ethoxy}ethoxy)acetylamino]ethoxy}ethoxy) acetyl][Aib8,$^{125}$I-Tyr19,Arg34]GLP-1(7-37) or N-epsilon37-[2-(2-[2-(((S)-4-((S)-4-(12-[4-(16-(1H-tetrazol-5-yl)hexadecanoylsulfamoyl)butyrylamino]dodecanoy-lamino)-4-carboxybutyrylamino)-4-carboxybutyrylamino) ethoxy]ethoxy)acetyl][Aib8,$^{125}$I-Tyr19,Glu22,Arg26,34, Lys37] GLP-1(7-37)-NH$_2$, preferably in a buffer containing 100 mM Hepes, 100 mM NaCl, 10 mM MgSO$_4$, 0.025% Tween-20, pH 7.4; (iv) transferring the mixture into the wells of a scintillation counter such as Perkin Elmer Optiplate-96 6005290 (100 µl per well), using suitable volumes such as 100 µl of a suitable dilution series of the GLP-1 derivative to be measured, preferably in the same buffer; (v) centrifuging the plates after a suitable incubation time such as 20 hours, preferably with gentle rocking, more preferably at room temperature; (vi) counting the plates, e.g. on a TopCounter; and/or (vii) plotting bound cpm as a function of GLP-1 derivative concentration. The EC$_{50}$ value of the competition curve is preferably used as a measure of the affinity of the derivative for HSA. The HSA binding affinity may also be expressed as K$_d$ apparent (K$_d$ for Dissociation Equilibrium Constant).

In a first particular embodiment, the albumin binding affinity (i.e. the EC$_{50}$ value (in nM) of the competition curve, as measured using the assay of Example 41), is below 2000, preferably below 1500, more preferably below 1000, even more preferably below 800, and most preferably below 600 (nM).

In a second particular embodiment, the albumin binding affinity (i.e. the EC$_{50}$ value (in nM) of the competition curve, as measured using the assay of Example 41), is below 500, preferably below 400, more preferably below 300, even more preferably below 200, and most preferably below 100 (nM).

In a third particular embodiment, the albumin binding affinity of the GLP-1 derivative of the invention is below 1 micromolar, preferably below 500 nM, and even more preferably below 200 nM, or even below 100 nM.

Accordingly, exemplary ranges of albumin binding affinity (EC50 in nM) of the GLP-1 derivative of the invention are: 1-2000, 100-2000, 200-2000, 400-1500, 600-1500, and 800-1500 (nM).

In a fifth aspect, the GLP-1 derivative of the invention has a high affinity binding to the isolated N-terminal extracellular domain of the GLP-1 receptor (nGLP-1R). The affinity may be measured as the ability to displace $^{125}$I-Exendin-4(9-39) from binding to nGLP-1R, e.g. as described in Example 42.

The protein nGLP-1R may be prepared as described by Runge et al 2007 (In Biochemistry, vol. 46, pp. 5830-5840). The protein is then biotinylated and immobilized, preferably on streptavidin-coated SPA beads. The nGLP1R in a suitable buffer such as 0.1M NaHCO$_3$ may be biotinylated using 75 µg BNHS (Sigma H1759) to 1 mg protein. The biotinylated nGLP1R is subsequently preferably dialyzed against PBS. All reagents and derivatives are preferably diluted in PBS, preferably with 0.05% v/v Tween 20. The binding assay may e.g. be carried out in 96 well OptiPlates (PerkinElmer 6005290) in a final volume of 200 µl. Each well may contain 2 mg streptavidin coated SPA beads (such as PerkinElmer RPNQ007), 0.1 pmol biotinylated nGLP1R, 50 pCi $^{125}$I-Exendin (9-39) and test peptide in suitable final concentrations, e.g. ranging from 1000 nM to 0.064 nM. The plates are incubated on a shaker, preferably at RT (room temperature), or at 20° C., and for a suitable period of time, e.g. 3 hours. The SPA particles may be spun down by centrifugation, e.g. for 10 min at 1500 rpm, and the plates are counted, e.g. in a TopCount-NXT (PerkinElmer).

The affinity may be expressed by way of an IC$_{50}$ value, which is read from the curve as the concentration of the GLP-1 derivative which displaces 50% of $^{125}$I-Exendin-4(9-39) from binding to nGLP-1R.

In a first particular embodiment, the GLP-1 derivative of the invention has an affinity to the extracellular domain of the GLP-1 receptor (nGLP-1R), measured as IC$_{50}$/nM in the assay of Example 42, of below 1500, preferably below 1000, even more preferably below 500, and most preferably below 400 (nM).

In a second particular embodiment, the GLP-1 derivative of the invention has an affinity to the extracellular domain of the GLP-1 receptor (nGLP-1R), measured as IC$_{50}$/nM in the assay of Example 42, of below 300, preferably below 200, even more preferably below 150, and most preferably below 100 (nM).

In a third particular embodiment, the GLP-1 derivative of the invention has an affinity to the extracellular domain of the GLP-1 receptor (nGLP-1R), measured as IC$_{50}$/nM in the assay of Example 42, of below 80, preferably below 60, even more preferably below 40, and most preferably below 20 (nM).

In a fourth particular embodiment, the GLP-1 derivative of the invention has an affinity to the extracellular domain of the GLP-1 receptor (nGLP-1R), measured as IC$_{50}$/nM in the assay of Example 42, of below 15, preferably below 10, even more preferably below 8, and most preferably below 6 (nM).

In a fifth particular embodiment, the GLP-1 derivative of the invention has an affinity to the extracellular domain of the GLP-1 receptor (nGLP-1R), measured as IC$_{50}$/nM in the assay of Example 42, of below 5.0, preferably below 4.0, even more preferably below 3.0, and most preferably below 2.0 (nM).

Accordingly, exemplary ranges of affinity to nGLP-1R (IC$_{50}$ in nM) of the GLP-1 derivative of the invention are: 2-1500, 2-1000, 2-500, 2-300, 5-500, 10-500, and 2-10 (nM).

In this assay Exendin-4 binds nGLP-1R with an IC$_{50}$ value of 5 nM, GLP-1(7-37) binds nGLP-1R with an IC$_{50}$ value of 1120 nM and liraglutide binds nGLP-1R with an IC$_{50}$ value of 1500 nM.

In a sixth particular embodiment, the GLP-1 derivative of the invention binds nGLP-1R with an IC$_{50}$ value lower than that of liraglutide, more preferably with an IC$_{50}$ value lower than 100 nM, and even more preferably below 10 nM, or even below 5 nM.

In a sixth aspect, The term "DPP-IV protected" as used herein referring to a polypeptide means a polypeptide which has been chemically modified in order to render said derivative resistant to the plasma peptidase dipeptidyl aminopeptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to DPP-IV mediated hydrolysis in order to reduce the rate of degradation by DPP-IV.

In one embodiment a derivative according to the invention is a DPP-IV protected derivative which is more resistant to DPP-IV than liraglutide.

Resistance of a peptide to degradation by dipeptidyl aminopeptidase IV is determined by the following degradation assay: Aliquots of the peptide (5 nmol) are incubated at 37° C. with 1 µL of purified dipeptidyl aminopeptidase IV corresponding to an enzymatic activity of 5 mU for 10-180 minutes in 100 µL of 0.1 M triethylamine-HCl buffer, pH 7.4. Enzymatic reactions are terminated by the addition of 5 µL of 10% trifluoroacetic acid, and the peptide degradation products are separated and quantified using HPLC analysis. One method for performing this analysis is: The mixtures are applied onto a Vydac C18 widepore (30 nm pores, 5 µm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J.

Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed.

Alternatively, the resistance of a peptide to degradation by dipeptidyl aminopeptidase IV is determined by the following degradation assay: Aliquots of the peptide (4 nmol) are incubated at 37° C. with 10.9 mU of purified dipeptidyl aminopeptidase IV for 22 hours in 40 µL of 0.085 M Tris-HCl buffer, pH 8.0, in presence or absence of 1.6% human serum albumin. After 0, 4, and 22 hours samples of 10 µl are taken and enzymatic reactions are terminated by mixing with 100 µl of 1% trifluoroacetic acid. The peptide degradation products are separated and quantified using HPLC analysis. One method for performing this analysis is: The mixtures are applied onto an Agilent Zorbax 300SB-C18 (5 µm particles) 150×2.1 mm column and eluted at a flow rate of 0.5 ml/min with a linear gradient from 0.1% trifluoroacetic acid to 100% acetonitrile with 0.07% TFA in 30 minutes. Peptides and their degradation products are monitored by their absorbance at 214 nm, and are quantified by integration of their peak areas. The stability of a peptide against dipeptidyl aminopeptidase IV is determined as the peak area of the intact peptide relative to the sum of the peak areas of the intact peptide and the degradation product lacking the two aminoterminal amino acids after cleavage.

In a seventh aspect, the present invention relates to a derivative of a GLP-1 peptide which can be formulated into particles suitable for pulmonary administration (delivery). This may be with regard to physical or chemical aspects which are useful for a pulmonal formulation. Alternatively, the derivatives are stable against degradation by enzymes in the airways and lungs.

In embodiments of the invention a combination of one or more of the above features is achieved.

Albumin Binding

The term "albumin binding moiety" as used herein means a residue which binds non-covalently to human serum albumin. The albumin binding residue attached to the therapeutic polypeptide typically has an albumin binding affinity that is below 1 micromolar, preferable below 500 nM and even more preferable below 200 nM or even below 100 nM.

A range of albumin binding residues are known among linear and branched lipohophillic moieties containing 4-40 carbon atoms having a distal acidic group.

The term "hydrophilic linker" as used herein means a spacer that separates a peptide and an albumin binding residue with a chemical moiety which comprises at least 5 non-hydrogen atoms where 30-50% of these are either N or O.

In the formulas below the terminal bonds from the attached groups are to be regarded as attachment bonds and not ending in methylene groups unless stated.

Another object of the present invention is to provide a pharmaceutical formulation comprising a derivative according to the present invention which is present in a concentration from 0.1 mg/ml to 25 mg/ml, and wherein said formulation has a pH from 3.0 to 9.0. The formulation may further comprise a buffer system, preservative(s), tonicity agent(s), chelating agent(s), stabilizers and surfactants.

Formulation

In one embodiment of the invention, the pharmaceutical formulation is an aqueous formulation, i.e. formulation comprising water. Such formulation is typically a solution or a suspension.

In a further embodiment of the invention, the pharmaceutical formulation is an aqueous solution.

The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the invention relates to a pharmaceutical formulation comprising an aqueous solution of a derivative according to the present invention, and a buffer, wherein said derivative is present in a concentration from 0.1 mg/ml or above, and wherein said formulation has a pH from about 3.0 to about 9.0.

In another embodiment of the invention, the pH of the formulation is from about 7.0 to about 9.5. In another embodiment of the invention, the pH of the formulation is from about 3.0 to about 7.0. In another embodiment of the invention, the pH of the formulation is from about 5.0 to about 7.5. In another embodiment of the invention, the pH of the formulation is from about 7.5 to about 9.0. In another embodiment of the invention, the pH of the formulation is from about 7.5 to about 8.5. In another embodiment of the invention, the pH of the formulation is from about 6.0 to about 7.5. In another embodiment of the invention, the pH of the formulation is from about 6.0 to about 7.0. In another embodiment, the pharmaceutical formulation is from 8.0 to 8.5.

In an embodiment of the invention, each administered dose contains from 0.01 mg-10 mg of active derivative. In an embodiment, the dose administered contains more than 0.05 mg active derivative. In an embodiment, the dose administered contains more than 0.1 mg active derivative. In an embodiment, the dose administered contains up to 10 mg active derivative. In an embodiment, the dose administered contains up to 9 mg active derivative. In an embodiment, the dose administered contains up to 8 mg active derivative. In an embodiment, the dose administered contains up to 7 mg active derivative. In an embodiment, the dose administered contains up to 6 mg active derivative. In an embodiment, the dose administered contains up to 5 mg active derivative. In an embodiment, the dose administered contains from 0.2 mg to 5 mg active derivative.

In a further embodiment of the invention, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention, the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In an embodiment, the preservative is phenol or m-cresol. In a further embodiment of the invention, the preservative is present in a concentration from 0.1 mg/ml to 20 mg/ml. In a further embodiment of the invention, the preservative is present in a concentration from 0.1 mg/ml to 5 mg/ml. In a further embodiment of the invention, the preservative is present in a concentration from 5 mg/ml to 10 mg/ml. In a further embodiment of the invention, the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19$^{th}$ edition, 1995.

In a further embodiment of the invention, the formulation further comprises an isotonic agent. In a further embodiment of the invention, the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. In an embodiment, the isotoncity agent is propyleneglycol. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention, the isotonic agent is present in a concentration from 1 mg/ml to 50 mg/ml. In a further embodiment of the invention, the isotonic agent is present in a concentration from 1 mg/ml to 7 mg/ml. In an embodiment of the invention, the isotonic agent is present in a concentration from 5 mg/ml to 7 mg/ml. In a further embodiment of the invention, the isotonic agent is present in a concentration from 8 mg/ml to 24 mg/ml. In a further embodiment of the invention, the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: The Science and Practice of Pharmacy, 19$^{th}$ edition, 1995.

In a further embodiment of the invention, the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: The Science and Practice of Pharmacy, 19$^{th}$ edition, 1995.

In a further embodiment of the invention, the formulation further comprises a stabilizer. The use of a stabilizer in pharmaceutical compositions is well-known to the skilled person. For convenience reference is made to Remington: The Science and Practice of Pharmacy, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations.

By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) 3. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention, methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention, the formulation further comprises a stabilizer selected from the group of high molecular weight polymers or low molecular compounds.

In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein.

Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention, the formulation further comprises a surfactant. In another embodiment of the invention, the pharmaceutical composition comprises two different surfactants. The term "Surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general.

Anionic surfactants may be selected from the group of: Chenodeoxycholic acid, Chenodeoxycholic acid sodium salt, Cholic acid, Dehydrocholic acid, Deoxycholic acid, Deoxycholic acid methyl ester, Digitonin, Digitoxigenin, N,N-Dimethyldodecylamine N-oxide, Docusate sodium, Glycochenodeoxycholic acid sodium, Glycocholic acid hydrate, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine sodium salt, N-Lauroylsarcosine, N-Lauroylsarcosine, Lithium dodecyl sulfate, Lugol, 1-Octanesulfonic acid sodium salt, 1-Octanesulfonic acid sodium salt, Sodium 1-butanesulfonate, Sodium 1-decanesulfonate, Sodium 1-dodecanesulfonate, Sodium 1-heptanesulfonate, Sodium 1-heptanesulfonate, Sodium 1-nonanesulfonate, Sodium 1-propanesulfonate monohydrate, Sodium 2-bromoethanesulfonate, Sodium cholate hydrate, ox or sheep bile, Sodium cholate hydrate, Sodium choleate, Sodium deoxycholate, Sodium dodecyl sulfate, Sodium dodecyl sulfate, Sodium hexanesulfonate, Sodium octyl sulfate, Sodium pentanesulfonate, Sodium taurocholate, Taurochenodeoxycholic acid sodium salt, Taurodeoxycholic acid sodium salt monohydrate, Taurolithocholic acid 3-sulfate disodium salt, Tauroursodeoxycholic acid sodium salt, Trizma® dodecyl sulfate, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), Dodecylphosphocholine (FOS-Choline-12), Decylphosphocholine (FOS-Choline-10), Nonylphosphocholine (FOS-Choline-9), dipalmitoyl phosphatidic acid, sodium caprylate, and/or Ursodeoxycholic acid.

Cationic surfactants may be selected from the group of: Alkyltrimethylammonium bromide Benzalkonium chloride, Benzalkonium chloride, Benzyldimethylhexadecylammonium chloride, Benzyldimethyltetradecylammonium chloride, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Hexadecyltrimethylammonium bromide, Hexadecyltrimethylammonium bromide, Polyoxyethylene(10)-N-tallow-1,3-diaminopropane, Thonzonium bromide, and/or Trimethyl(tetradecyl)ammonium bromide.

Nonionic surfactants may be selected from the group of: BigCHAP, Bis(polyethylene glycol bis[imidazoyl carbonyl]), block copolymers as polyethyleneoxide/polypropyleneoxide block copolymers such as poloxamers, poloxamer 188 and poloxamer 407, Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Dodecanoyl-N-methylglucamide, alkyl-polyglucosides, ethoxylated castor oil, Heptaethylene glycol monodecyl ether, Heptaethylene glycol monododecyl ether, Heptaethylene glycol monotetradecyl ether, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-beta-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-f3-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tetradecyl-β-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165 solution, Triton® X-305 solution, Triton® X-405, Triton X-45, Triton® X-705-70, TWEEN® 20, TWEEN® 40, TWEEN® 60, TWEEN® 6, TWEEN® 65, TWEEN® 80, TWEEN® 81, TWEEN® 85, Tyloxapol, sphingophospholipids (sphingomyelin), and sphingoglycolipids (ceramides, gangliosides), phospholipids, and/or n-Undecyl β-D-glucopyranoside.

Zwitterionic surfactants may be selected from the group of: CHAPS, CHAPSO, 3-(Decyldimethylammonio)propanesulfonate inner salt, 3-(Dodecyldimethylammonio)-propanesulfonate inner salt, 3-(Dodecyldimethylammonio)propanesulfonate inner salt, 3-(N,N-Dimethylmyristylammonio) propanesulfonate, 3-(N,N-Dimethyloctadecylammonio)-propanesulfonate, 3-(N,N-Dimethyloctylammonio) propanesulfonate inner salt, 3-(N,N-Dimethylpalmitylammonio)propanesulfonate, N-alkyl-N,N-dimethylammonio-1-propanesulfonates, 3-cholamido-1-propyldimethylammonio-1-propanesulfonate, Dodecylphosphocholine, myristoyl lysophosphatidylcholine, Zwittergent 3-12 (N-dodecyl-N,N-dimethyl-3-ammonio-1-propanesulfonate), Zwittergent 3-10 (3-(Decyldimethyl-ammonio)propanesulfonate inner salt), Zwittergent 3-08 (3-(Octyldimethylammonio)propanesulfonate), glycerophospholipids (lecithins, kephalins, phosphatidyl serine), glyceroglycolipids (galactopyranoside), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, lysophosphatidylserine and lysophosphatidylthreonine, acylcarnitines and derivatives, $N^{beta}$-acylated derivatives of lysine, arginine or histidine, or side-chain acylated derivatives of lysine or arginine, $N^{beta}$-acylated derivatives of dipeptides comprising any combination of lysine, arginine or histidine and a neutral or acidic amino acid, $N^{beta}$-acylated derivative of a tripeptide comprising any combination of a neutral amino acid and two charged amino acids, or the surfactant may be selected from the group of imidazoline derivatives, long-chain fatty acids and salts thereof$_6$-$C_{12}$ (eg. oleic acid and caprylic acid), N-Hexadecyl-N,N-dimethyl-3-ammonio-1-propane-sulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), or mixtures thereof.

The term "alkyl-polyglucosides" as used herein in relates to an straight or branched $C_{5-20}$-alkyl, -alkenyl or -alkynyl chain which is substituted by one or more glucoside moieties such as maltoside, saccharide etc. Embodiments of these alkyl-polyglucosides include $C_{6-18}$-alkyl-polyglucosides. Specific embodiments of these alkyl-polyglucosides includes the even numbered carbon-chains such as $C_6$, $C_8$, $C_{10}$, $C_{12}$, $C_{14}$, $C_{16}$, $C_{18}$ and $C_{20}$ alkyl chain. Specific embodiments of the glucoside moieties include pyranoside, glucopyranoside, maltoside, maltotrioside and sucrose. In embodiments of the invention, less than 6 glucosid moieties are attached to the alkyl group. In embodiments of the invention, less than 5 glucosid moieties are attached to the alkyl group. In embodiments of the invention, less than 4 glucosid moieties are attached to the alkyl group. In embodiments of the invention, less than 3 glucosid moieties are attached to the alkyl group. In embodiments of the invention, less than 2 glucosid moieties are attached to the alkyl group. Specific embodiments of alkyl-polyglucosides are alkyl glucosides such n-decyl β-D-glucopyranoside, decyl β-D-maltopyranoside, dodecyl β-D-glucopyranoside, n-dodecyl β-D-maltoside, n-dodecyl β-D-maltoside, n-dodecyl β-D-maltoside, tetradecyl β-D-glucopyranoside, decyl β-D-maltoside, hexadecyl β-D-maltoside, decyl β-D-maltotrioside, dodecyl β-D-maltotrioside, tetradecyl β-D-maltotrioside, hexadecyl β-D-maltotrioside, n-dodecyl-sucrose, n-decyl-sucrose, sucrose monocaprate, sucrose monolaurate, sucrose monomyristate, and sucrose monopalmitate.

The use of a surfactant in pharmaceutical compositions is well-known to the skilled person. For convenience reference is made to Remington: *The Science and Practice of Pharmacy*, 19$^{th}$ edition, 1995.

In a further embodiment of the invention, the formulation further comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a derivative according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, chewing gum, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants. Compositions of the invention may further be compounded in, or attached to, for example through covalent, hydrophobic and electrostatic interactions, a drug carrier, drug delivery system and advanced drug delivery system in order to further enhance stability of the derivative of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions thereof, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of derivatives of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension or a powder for the administration of the derivative of the present invention in the form of a nasal or pulmonal liquid or powder spray. As a still further option, the pharmaceutical compositions containing the derivative of the invention can also be adapted to transdermal administration, e.g. by needle-free injection or from a patch, optionally an iontophoretic patch, or transmucosal, e.g. buccal, administration.

The derivatives of the present invention can be administered via the pulmonary route in a vehicle, as a solution, suspension or dry powder using any of known types of devices suitable for pulmonary drug delivery. Examples of these comprise, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used interchangeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. 3 Appl Physiol 84(2) (1998) 379-385). MMAD is normally calculated from the measurement made with impactors, an instrument that measures the particle inertial behaviour in air. In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. 3 Appl Physiol 84(2) (1998) 379-385).

Deep lung deposition of the pulmonal formulations comprising the derivative of the present invention may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention, the pharmaceutical formulation comprising the derivative of the present invention is stable for more than 6 weeks of usage and for more than 3 years of storage.

In another embodiment of the invention, the pharmaceutical formulation comprising the derivative of the present invention is stable for more than 4 weeks of usage and for more than 3 years of storage.

In a further embodiment of the invention, the pharmaceutical formulation comprising the derivative of the present invention is stable for more than 4 weeks of usage and for more than two years of storage.

In an even further embodiment of the invention, the pharmaceutical formulation comprising the derivative of the present invention is stable for more than 2 weeks of usage and for more than two years of storage.

In another aspect, the present invention relates to the use of a derivative according to the invention for the preparation of a medicament.

In one embodiment, a derivative according to the invention is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, stroke, coronary heart disease and other cardiovascular disorders, inflammatory bowel syndrome, dyspepsia and gastric ulcers.

In another embodiment, a derivative according to the invention is used for the preparation of a medicament for delaying or preventing disease progression in type 2 diabetes.

In another embodiment a derivative according to the invention is used for the preparation of a medicament for decreasing food intake, decreasing β-cell apoptosis, increasing β-cell function and β-cell mass, and/or for restoring glucose sensitivity to β-cells.

The treatment with a derivative according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with surgery—a surgery that influence the glucose levels and/or lipid homeostasis such as gastric banding or gastric bypass.

It should be understood that any suitable combination of the derivatives according to the invention with one or more of the above-mentioned compounds and optionally one or more further pharmacologically active substances are considered to be within the scope of the present invention.

Method of Manufacturing

Depending on the sequence the analogues of this invention can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the therapeutic polypeptide may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, EF and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well-known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein. The procedures used to ligate the DNA sequences coding for the present peptide, the promoter and optionally the terminator and/or secretory signal sequence, respectively, and to insert them into suitable vectors containing the information necessary for replication, are well-known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well-known and used in the art are, without limitation, *E. coli*, *Saccharomyces cerevisiae*, or mammalian BHK or CHO cell lines.

Embodiments According to the Invention

1. A GLP-1 derivative which comprises a modified GLP-1 sequence 7-37 (SEQ ID No 1) having:
   i) a total of 2, 3, 4, 5 or 6 amino acid substitutions compared to the sequence 7-37 of SEQ ID No 1, including
      a) a Glu residue at a position equivalent to position 22 of SEQ ID No 1 and
      b) an Arg residue at a position equivalent to position 26 of SEQ ID No 1,
   ii) optionally a C terminal extension of 1 amino acid residue,
   iii) optionally the amino acid at a position equivalent to position 37 of SEQ ID No 1 can be absent, and
   iv) optionally a C-terminal amide group,
   and which is derivatised with an albumin binding residue or pegylated in a position selected from a position equivalent to position 18, 20, 23, 30, 31, 34, 36 or 37 of SEQ ID No 1, preferably at position 18, 23, 31, 34, 36 or 37 of SEQ ID No 1.

2. The GLP-1 derivative according to embodiment 1 which comprises a modified GLP-1 sequence 7-37 (SEQ ID NO 1) having:
   i) a total of 2, 3, 4, 5 or 6 amino acid substitutions compared to the sequence 7-37 of SEQ ID NO 1, including
      a) a Glu residue at a position equivalent to position 22 of SEQ ID No 1 and
      b) an Arg residue at a position equivalent to position 26 of SEQ ID No 1, and which is derivatised with an albumin binding residue or pegylated in a position selected from a position equivalent to position 18, 20, 23, 30, 31, 34, 36 or 37 of SEQ ID No 1, preferably at position 18, 23, 31, 34, 36 or 37 of SEQ ID No 1.

3. The GLP-1 derivative according to embodiment 1, wherein the amino acid at a position equivalent to position 37 of SEQ ID No 1 is absent, and which is derivatised with an albumin binding residue or pegylated in a position selected from at position equivalent to position 18, 23, 31, 34 or 36 of SEQ ID NO 1,
   and wherein the total length of the GLP-1 analogue is 30 amino acids.

4. The GLP-1 derivative according to embodiment 1 having a C terminal extension of 1 amino acid residue in length and wherein the total length of the GLP-1 analogue is 32 amino acids.

5. The GLP-1 derivative according to any one of the embodiments 1-4 having a C-terminal amide group.

6. The GLP-1 derivative according to any one of the embodiments 1-5 having the sequence of formula (I)

```
Formula (I)
                                            (SEQ ID No: 2)
Xaa7-Xaa8-Xaa9-Gly-Thr-Phe-Thr-Ser-Asp-Xaa16-

Ser-Xaa18-Tyr-Xaa20-Glu-Glu-Xaa23-Xaa24-Xaa25-
```

```
                    -continued
Arg-Xaa27-Phe-Ile-Xaa30-Xaa31-Leu-Xaa33-Xaa34-

Xaa35-Xaa36-Xaa37-Xaa38-R,
``` preferably having the sequence of formula (I') which is identical to formula (I) except for having Leu at position 20,
wherein
Xaa$_7$-Xaa$_8$ is L-histidine-Aib, desamino-histidine-alanine or desamino-histidine-Aib
Xaa$_9$ is Glu or a Glu derivative such as alpha, alpha dimethyl-Glu
Xaa$_{16}$ is Val or Leu;
Xaa$_{18}$ is Ser, Lys, Cys or Arg;
Xaa$_{20}$ is Leu or Lys
Xaa$_{23}$ is Gln, Glu, Lys, Cys or Arg;
Xaa$_{24}$ is Ala or Asn
Xaa$_{25}$ is Ala or Val;
Xaa$_{27}$ is Glu, Ala or Leu;
Xaa$_{30}$ is Ala, Glu, Lys or Arg, preferably Ala, Glu or Arg;
Xaa$_{31}$ is Trp, Cys or Lys;
Xaa$_{33}$ is Val, Cys or Lys;
Xaa$_{34}$ is Lys, Cys, Glu, Asn or Arg;
Xaa$_{35}$ is Gly or Aib;
Xaa$_{36}$ is Arg or Lys,
Xaa$_{37}$ is Gly, Aib, Cys, Lys or absent
Xaa$_{38}$ is Lys, Glu or absent;
R is amide or absent
provided that if Xaa$_{37}$ is absent, then Xaa$_{38}$ is also absent,
and which is derivatised with an albumin binding residue or pegylated in a position selected from a position equivalent to position 18, 20, 23, 30, 31, 34, 36 or 37 of SEQ ID No 1, preferably at position 18, 23, 31, 34, 36 or 37 of SEQ ID No 1.

7. The GLP-1 derivative according to any one of the embodiments 1-5 having the sequence of formula (II)

```
Formula (II)
                                            (SEQ ID No: 3)
Xaa7-Xaa8-Glu-Gly-Thr-Phe-Thr-Ser-Asp-Val-Ser- Xaa18-Tyr-Leu-Glu-Glu-Gln-Ala-Ala-Arg-Glu-Phe- Ile-Xaa30-Trp-Leu-Xaa33-Xaa34-Xaa35-Xaa36-Xaa37-

Xaa38-R
``` wherein
Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;
Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{18}$ is Ser, Lys or Arg;
Xaa$_{30}$ is Ala, Glu or Arg;
Xaa$_{33}$ is Val or Lys;
Xaa$_{34}$ is Lys, Glu or Arg;
Xaa$_{35}$ is Gly or Aib;
Xaa$_{36}$ is Arg or Lys,
Xaa$_{37}$ is Gly, Aib, Lys or absent,
Xaa$_{38}$ is Lys, Glu or absent,
R is amide or is absent and which is derivatised with an albumin binding residue or pegylated in a position selected from a position equivalent to position 18, 20, 23, 30, 31, 34, 36 or 37 of SEQ ID No 1, preferably at position 18, 23, 31, 34, 36 or 37 of SEQ ID No 1.

8. The GLP-1 derivative according to any one of the embodiments 1-7, wherein at least one amino acid residue is derivatised with A-B-C-D- wherein A- is selected from the group consisting of

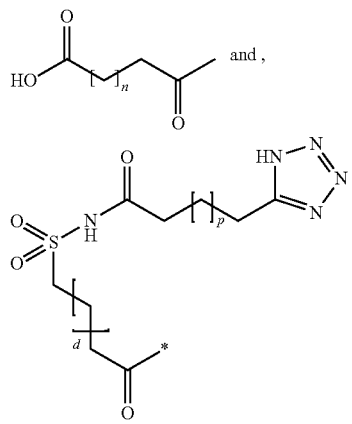

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, —B— is selected from the group consisting of

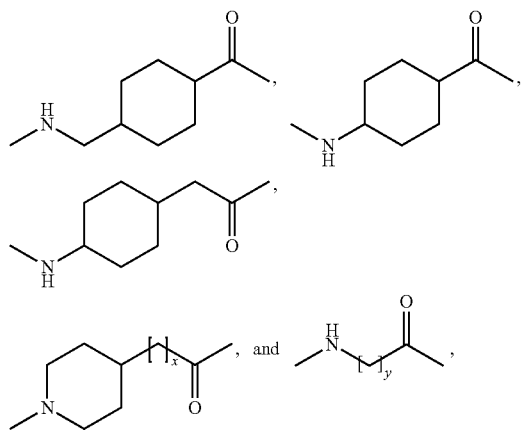

wherein x is selected from the group consisting of 0, 1, 2, 3 and 4, and y is selected from the group consisting of 1, 2, 3, 4, 5, 6, 7, 8, 9, 10, 11 and 12, —C— is selected from the group consisting of

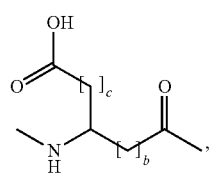

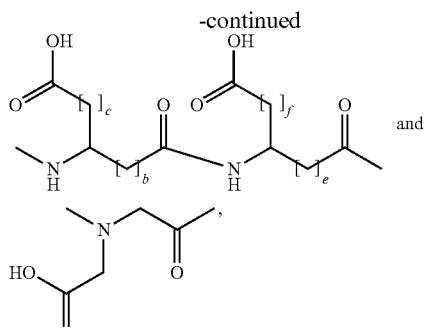

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker.

9. The GLP-1 derivative according to any one of embodiments 52-55, wherein the derivatised amino acid residue is lysine.

10. A pharmaceutical composition comprising a derivative according to any one of embodiments 1-9, and a pharmaceutically acceptable excipient.

11. A derivative according to any one of the embodiments 1-9 for use in the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers.

The amino acid sequence of human GLP-1(7-37) is included in the Sequence Listing as SEQ ID No: 1, and SEQ ID Nos: 2 and 3 are derivatives thereof according to the invention. In the Sequence Listing, the numbering starts with amino acid residue no. 1. Accordingly, e.g., position 1 of SEQ ID No 1 is equivalent to position 7 of GLP-1(7-37) (His), position 16 of SEQ ID No 1 is equivalent to position 22 of GLP-1(7-37) (Gly), and position 20 of SEQ ID No 1 is equivalent to position 26 of GLP-1(7-37) (Lys)- and vice versa for the other positions and the other sequences.

Accordingly, the invention also provides, in claim 1 of the priority applications, a GLP-1 derivative which comprises a modified GLP-1(7-37) sequence having:

i) a total of 2, 3, 4, 5 or 6 amino acid substitutions compared to the sequence of SEQ ID No 1, including
  a) a Glu residue at a position equivalent to position 22 of GLP-1(7-37) (position 16 of SEQ ID No 1) and
  b) an Arg residue at a position equivalent to position 26 of GLP-1(7-37) (position 20 of SEQ ID No 1),
ii) optionally a C terminal extension of 1 amino acid residue,
iii) optionally the amino acid at a position equivalent to position 37 of GLP-1(7-37) (position 31 of SEQ ID No 1) can be absent, and
iv) optionally a C-terminal amide group, and which is derivatised with an albumin binding residue or pegylated in a position selected from a position equivalent to position 18, 20, 23, 30, 31, 34, 36 or 37 of GLP-1(7-37) (position 12, 14, 17, 24, 25, 28, 30 or 31, respectively, of SEQ ID No 1); The invention furthermore provides GLP-1 derivatives, methods and uses thereof, and pharmaceutical compositions with a content thereof corresponding to any of the claims and particular embodiments according to the invention, in which corresponding position numbering amendments have been made as explained above, and shown above for the GLP-1 derivative of claim 1 of the priority applications.

Additional Embodiments According to the Invention

1. A GLP-1 derivative which comprises a modified GLP-1 sequence 7-37 (SEQ ID No 1) having:
    i) a total of 2, 3, 4, 5 or 6 amino acid substitutions compared to the sequence 7-37 of SEQ ID No 1, including
        a) a Glu residue at a position equivalent to position 22 of SEQ ID No 1 and
        b) an Arg residue at a position equivalent to position 26 of SEQ ID No 1,
    ii) optionally a C terminal extension of 1 amino acid residue,
    iii) optionally the amino acid at a position equivalent to position 37 of SEQ ID No 1 can be absent, and
    iv) optionally a C-terminal amide group,
    and which is derivatised with an albumin binding residue or pegylated in a position selected from a position equivalent to position 18, 20, 23, 30, 31, 34, 36 or 37 of SEQ ID No 1, preferably 18, 23, 31, 34, 36 or 37 of SEQ ID No 1.

In embodiments of the invention a maximum of 6 amino acids have been modified. In embodiments of the invention a maximum of 5 amino acids have been modified. In embodiments of the invention a maximum of 4 amino acids have been modified. In embodiments of the invention a maximum of 3 amino acids have been modified. In embodiments of the invention a maximum of 2 amino acids have been modified. In embodiments of the invention 1 amino acid has been modified. In embodiments of the invention one amino acid has been added in the C-terminal. In embodiments of the invention one amino acid has been deleted in the C-terminal. In embodiments of the invention, there is a C-terminal amide group.

2. The GLP-1 derivative according to embodiment 1 which comprises a modified GLP-1 sequence 7-37 (SEQ ID NO 1) having:
    i) a total of 2, 3, 4, 5 or 6 amino acid substitutions compared to the sequence 7-37 of SEQ ID NO 1, including
        a) a Glu residue at a position equivalent to position 22 of SEQ ID No 1 and
        b) an Arg residue at a position equivalent to position 26 of SEQ ID No 1, and which is derivatised with an albumin binding residue or pegylated in a position selected from a position equivalent to position 18, 20, 23, 30, 31, 34, 36 or 37 of SEQ ID No 1, preferably 18, 23, 31, 34, 36 or 37 of SEQ ID No 1.

3. The GLP-1 derivative according to embodiment 1, wherein the amino acid at a position equivalent to position 37 of SEQ ID No 1 is absent, and which is derivatised with an albumin binding residue or pegylated in a position selected from at position equivalent to position 18, 23, 31, 34 or 36 of SEQ ID NO 1, and wherein the total length of the GLP-1 analogue is 30 amino acids.

4. The GLP-1 derivative according to embodiment 1 having a C terminal extension of 1 amino acid residue in length and wherein the total length of the GLP-1 analogue is 32 amino acids.

5. The GLP-1 derivative according to any one of the embodiments 1-4 having a C-terminal amide group.

6. The GLP-1 derivative according to any one of the embodiments 1-5 having 3 amino acid substitutions compared to the sequence 7-37 of SEQ ID NO 1 including the substitutions in position 22 and 26.

7. The GLP-1 derivative according to any one of the embodiments 1-6, which has a substitution selected at a position from the group of positions 7, 8, 18, 20, 23, 24, 25, 27, 30, 31, 33, 34 and 37 compared to the sequence 7-37 of SEQ ID NO 1.

8. The GLP-1 derivative according to embodiment 7, which has a substitution selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34, Asn34, Cys37 and Lys37.

9. The GLP-1 derivative according to any one of the embodiments 7-8, which has a substitution selected from the group consisting of desaminoHis7, Aib8, Lys18, Lys20, Lys23, Glu30, Lys31, Lys33, Lys 34 and Lys 37.

10. The GLP-1 derivative according to any one of the embodiments 7-9, which has a substitution selected from the group consisting of desaminoHis7 and Aib8.

11. The GLP-1 derivative according to any one of the embodiments 1-5 having 4 amino acid substitutions compared to the sequence 7-37 of SEQ ID NO 1 including the substitutions in position 22 and 26.

12. The GLP-1 derivative according to any one of the embodiments 1-5 and 11, which has two substitutions at a position selected from the group of positions 7, 8, 18, 20, 23, 24, 25, 27, 30, 31, 33, 34 and 37 compared to the sequence 7-37 of SEQ ID NO 1.

13. The GLP-1 derivative according to any one of the embodiments 11-12, which has two substitutions selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34, Asn34, Cys37 and Lys37.

14. The GLP-1 derivative according to any one of the embodiments 11-13 having an amino acid substitution selected from the group consisting of desaminoHis7 and Aib8 and an amino acid substitution selected from the group consisting Lys18, Lys20, Lys23, Glu30, Lys31, Lys33, Lys 34 and Lys 37.

15. The GLP-1 derivative according to any one of the embodiments 11-14 having an amino acid substitution selected from the group consisting desaminoHis7 and Aib8, and an amino acid substitution selected from the group consisting Lys18, Lys20, Lys23, Glu30, Lys31, Lys33, Lys 34 and Lys 37.

16. The GLP-1 derivative according to any one of the embodiments 1-5 having 5 amino acid substitutions compared to the sequence 7-37 of SEQ ID NO 1 including the substitutions in position 22 and 26.

17. The GLP-1 derivative according to any one of the embodiments 1-5 and 16, which has three amino acid substitutions at a position selected from the group of positions 7, 8, 18, 20, 23, 24, 25, 27, 30, 31, 33, 34 and 37 compared to the sequence 7-37 of SEQ ID NO 1.

18. The GLP-1 derivative according to any one of the embodiments 16-17, which has three amino acid substitutions selected from the group of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34, Asn34, Cys37 and Lys37.

19. The GLP-1 derivative according to any one of the embodiments 16-18 having an amino acid substitution selected from the group consisting of desaminoHis7 and Aib8, and two amino acid substitutions selected from the group consisting of Lys18, Lys20, Lys23, Glu30, Lys31, Lys33, Lys 34 and Lys 37.

20. The GLP-1 derivative according to any one of the embodiments 16-19 having an amino acid substitution selected from the group consisting of desaminoHis7 and Aib8, and two amino acid substitutions selected from the group consisting of Lys18, Lys20, Lys23, Glu30, Lys31, Lys33, Lys 34 and Lys 37.
21. The GLP-1 derivative according to any one of the embodiments 1-5 having 6 amino acid substitutions compared to the sequence 7-37 of SEQ ID NO 1 including the substitutions in position 22 and 26.
22. The GLP-1 derivative according to any one of the embodiments 1-5 and 21, which has four amino acid substitutions at a position selected from the group of positions 7, 8, 18, 20, 23, 24, 25, 27, 30, 31, 33, 34 and 37.
23. The GLP-1 derivative according to any one of the embodiments 21-22, which has four amino acid substitutions selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34, Asn34, Cys37 and Lys37.
24. The GLP-1 derivative according to any one of the embodiments 21-23 having an amino acid substitution selected from the group consisting of desaminoHis7 and Aib8 and three amino acid substitutions selected from the group consisting of Lys18, Lys20, Lys23, Glu30, Lys31, Lys33, Lys34 and Lys37.
25. The GLP-1 derivative according to any one of the embodiments 21-24 having an amino acid substitution selected from the group consisting of desaminoHis7 and Aib8 and three amino acid substitutions selected from the group consisting of Lys18, Lys20, Lys23, Glu30, Lys31, Lys33, Lys34 and Lys37.
26. The GLP-1 derivative according to any one of the embodiments 1-25, which has been pegylated or derivatised with an albumin binding residue in position 18.
27. The GLP-1 derivative according to any one of the embodiments 1-26, which has been pegylated or derivatised with an albumin binding residue in position 23.
28. The GLP-1 derivative according to any one of the embodiments 1-26, which has been pegylated or derivatised with an albumin binding residue in position 31.
29. The GLP-1 derivative according to any one of the embodiments 1-26, which has been pegylated or derivatised with an albumin binding residue in position 34.
30. The GLP-1 derivative according to any one of the embodiments 1-26, which has been pegylated or derivatised with an albumin binding residue in position 36.
31. The GLP-1 derivative according to any one of the embodiments 1-26, which has been pegylated or derivatised with an albumin binding residue in position 37.
32. The GLP-1 derivative according to any one of the embodiments 1-31, which has been pegylated.
33. The GLP-1 derivative according to any one of the embodiments 1-32, wherein the amino acid at a position equivalent to position 37 of SEQ ID No 1 has been substituted with Lys, and which Lys residue is pegylated or derivatised with an albumin binding residue.
34. The GLP-1 derivative according to any one of the embodiments 1-33, which has been derivatised with an albumin binding residue.
35. The GLP-1 derivative according to any one of the embodiments 1-34 having the sequence of formula (I)

$Xaa_7-Xaa_8-Xaa_9-Gly-Thr-Phe-Thr-Ser-Asp-Xaa_{16}-Ser-$ $Xaa_{18}-Tyr-Xaa_{20}-Glu-Glu-Xaa_{23}-Xaa_{24}-Xaa_{25}-Arg-Xaa_{27}-$ $Phe-Ile-Xaa_{30}-Xaa_{31}-Leu-Xaa_{33}-Xaa_{34}-Xaa_{35}-Xaa_{36}-$ $Xaa_{37}-Xaa_{38}-R$

Formula (I) (SEQ ID No: 2), preferably Formula (I') which is identical to Formula (I) except for having a Leu at position 20,
Wherein
$Xaa_7-Xaa_8$ is L-histidine-Aib, desamino-histidine-alanine or desamino-histidine-Aib
$Xaa_9$ is Glu or a Glu derivative such as alpha, alpha dimethyl-Glu
$Xaa_{16}$ is Val or Leu;
$Xaa_{18}$ is Ser, Lys, Cys or Arg;
$Xaa_{20}$ is Leu or Lys
$Xaa_{23}$ is Gln, Glu, Lys, Cys or Arg;
$Xaa_{24}$ is Ala or Asn
$Xaa_{25}$ is Ala or Val;
$Xaa_{27}$ is Glu, Ala or Leu;
$Xaa_{30}$ is Ala, Glu, Lys or Arg, preferably Ala, Glu or Arg;
$Xaa_{31}$ is Trp, Cys or Lys;
$Xaa_{33}$ is Val, Cys or Lys;
$Xaa_{34}$ is Lys, Cys, Glu, Asn or Arg;
$Xaa_{35}$ is Gly or Aib;
$Xaa_{36}$ is Arg or Lys,
$Xaa_{37}$ is Gly, Aib, Cys, Lys or absent
$Xaa_{38}$ is Lys, Glu or absent;
R is amide or absent
provided that if $Xaa_{37}$ is absent, then $Xaa_{38}$ is also absent, and which is derivatised with an albumin binding residue or pegylated in a position selected from a position equivalent to position 18, 20, 23, 30, 31, 34, 36 or 37 of SEQ ID No 1, preferably 18, 23, 31, 34, 36 or 37 of SEQ ID No 1.
36. The GLP-1 derivative according to any one of the embodiments 1-35 having the sequence of formula (II)

```
Formula (II)
                                            (SEQ ID No: 3)
Xaa₇-Xaa₈-Glu-Gly-Thr-Phe-Thr-Ser-Asp-Val-Ser- Xaa₁₈-Tyr-Leu-Glu-Glu-Gln-Ala-Ala-Arg-Glu- Phe-Ile-Xaa₃₀-Trp-Leu-Xaa₃₃-Xaa₃₄-Xaa₃₅-Xaa₃₆-

Xaa₃₇-Xaa₃₈-R
``` wherein
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{18}$ is Ser, Lys or Arg;
$Xaa_{30}$ is Ala, Glu or Arg;
$Xaa_{33}$ is Val or Lys;
$Xaa_{34}$ is Lys, Glu or Arg;
$Xaa_{35}$ is Gly or Aib;
$Xaa_{36}$ is Arg or Lys,
$Xaa_{37}$ is Gly, Aib, Lys or absent
$Xaa_{38}$ is Lys, Glu or absent;
R is amide or is absent
and which is derivatised with an albumin binding residue or pegylated in a position selected from a position equivalent to position 18, 20, 23, 30, 31, 34, 36 or 37 of SEQ ID No 1, preferably at position 18, 23, 31, 34, 36 or 37 of SEQ ID No 1.
37. The GLP-1 derivative according to any one of the embodiments 35-36, wherein $Xaa_{38}$ is absent.

38. The GLP-1 derivative according to any one of the embodiments 35-37, wherein Xaa$_{37}$ and Xaa$_{38}$ are both absent.
39. The GLP-1 derivative according to any one of the embodiments 35-38, wherein Xaa$_{37}$ and Xaa$_{38}$ are both absent, and Xaa$_{36}$ is Xaa$_{36}$-amide.
40. The GLP-1 derivative according to any one of the embodiments 35-39, wherein 3 amino acids are substituted compared to the sequence 7-37 of SEQ ID NO 1 and where Xaa$_7$ is desamino-histidine.
41. The GLP-1 derivative according to any one of the embodiments 35-39, wherein 4 amino acids are substituted compared to the sequence 7-37 of SEQ ID NO 1 and where Xaa$_7$ is desamino-histidine.
42. The GLP-1 derivative according to any one of the embodiments 35-39, wherein 5 amino acids are substituted compared to the sequence 7-37 of SEQ ID NO 1 and where Xaa$_7$ is desamino-histidine.
43. The GLP-1 derivative according to any one of the embodiments 35-39, wherein 6 amino acids are substituted compared to the sequence 7-37 of SEQ ID NO 1 and where Xaa$_7$ is desamino-histidine.
44. The GLP-1 derivative according to any one of the embodiments 35-39, wherein 3 amino acids are substituted compared to the sequence 7-37 of SEQ ID NO 1 and where Xaa$_8$ is Aib.
45. The GLP-1 derivative according to any one of the embodiments 35-39, wherein 4 amino acids are substituted compared to the sequence 7-37 of SEQ ID NO 1 and where Xaa$_8$ is Aib.
46. The GLP-1 derivative according to any one of the embodiments 35-39, wherein 5 amino acids are substituted compared to the sequence 7-37 of SEQ ID NO 1 and where Xaa$_8$ is Aib.
47. The GLP-1 derivative according to any one of the embodiments 35-39, wherein 6 amino acids are substituted compared to the sequence 7-37 of SEQ ID NO 1 and where Xaa$_8$ is Aib.
48. The GLP-1 derivative according to any one of the embodiments 35-47, wherein Xaa$_7$ is desamino-histidine.
49. The GLP-1 derivative according to any one of the embodiments 1-48, which comprises a hydrophilic spacer between the modified GLP-1 sequence and one or more albumin binding residue(s).
50. The GLP-1 derivative according to embodiment 49, wherein the hydrophilic spacer is an unbranched oligo ethylene glycol moiety with appropriate functional groups at both terminals that forms a bridge between an amino group of the modified GLP-1 sequence and a functional group of the albumin binding residue.
51. The GLP-1 derivative according to any one of the embodiments 1-59, which has been derivatised with an albumin binding residue.
52. The GLP-1 derivative according to any one of the embodiments 1-51, wherein at least one amino acid residue is derivatised with A-B-C-D-
    wherein A- is selected from the group consisting of

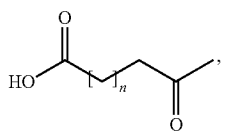

-continued

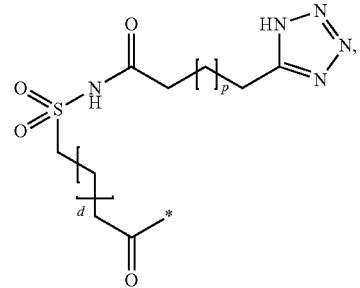

and tetrazole without sulphonamide,
wherein n is selected from the group consisting of 14, 15, 16 17, 18 and 19, p is selected from the group consisting of 10, 11, 12, 13 and 14, and d is selected from the group consisting of 0, 1, 2, 3, 4 and 5,
—B— is selected from the group consisting of

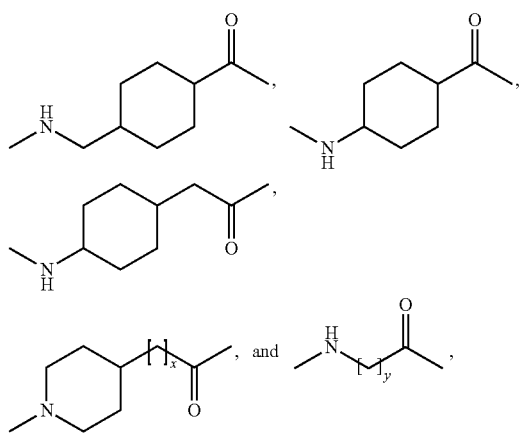

wherein x is selected from the group consisting of 0, 1, 2, 3 and 4, and y is selected from the group consisting of 1, 2, 3, 4, 5, 6, 7, 8, 9, 10, 11 and 12,
—C— is selected from the group consisting of

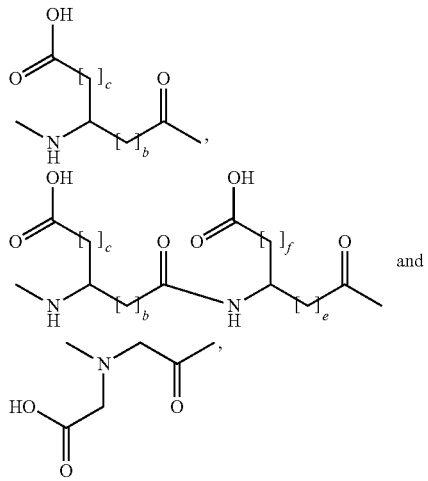

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and
-D- is attached to said amino acid residue and is a linker.

53. The GLP-1 derivative according to embodiment 52, wherein one amino acid residue is derivatised with A-B-C-D-.
54. The GLP-1 derivative according to any one of embodiments 52-53, wherein the derivatised amino acid residue comprises an amino group.
55. The GLP-1 derivative according to any one of embodiments 52-54, wherein the derivatised amino acid residue comprises a primary amino group in a side chain.
56. The GLP-1 derivative according to any one of embodiments 52-55, wherein the derivatised amino acid residue is lysine.
57. The GLP-1 derivative according to any one of embodiments 52-56, wherein only one amino acid residue is derivatised.
58. The GLP-1 derivative according to any one of embodiments 52-57, wherein A- is

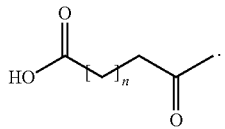

59. The GLP-1 derivative according to any of the embodiments 52-58, wherein n is selected from the group consisting of 15 and 17, and more is preferred 17.
60. The GLP-1 derivative according to any one of the embodiments 52-57, wherein A- is

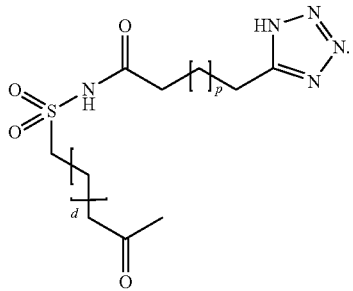

61. The GLP-1 derivative according to any of the embodiments 52-57 and 60, wherein p is selected from the group consisting of 12, 13, and 14 and more preferred is 13.
62. The GLP-1 derivative according to any of the embodiments 52-57 and 60-61, wherein d is selected from the group consisting of 0, 1, 2, 3 and 4, more preferred 0, 1 and 2 and most preferred 1.
63. The GLP-1 derivative according to any of the embodiments 52-57 and 52-62, wherein d is selected from the group consisting of 0, 1 and 2 and p is selected from the group consisting of 12, 13 or 14, more preferred d is selected from the group consisting of 1 and 2 and p is selected from the group consisting of 13 and 14, and most preferred d is 1 and p is 13.
64. The GLP-1 derivative according to any of the embodiments 52-63, wherein —B— is

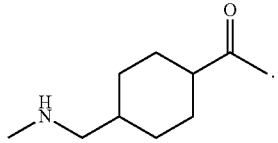

65. The GLP-1 derivative according to any of the embodiments 52-63, wherein —B— is

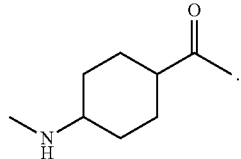

66. The GLP-1 derivative according to any of the embodiments 52-63, wherein —B— is

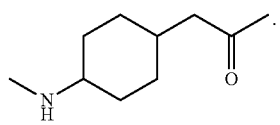

67. The GLP-1 derivative according to any of the embodiments 52-63, wherein —B— is

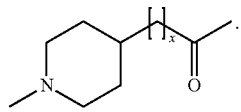

68. The GLP-1 derivative according to embodiment 67, wherein x is selected from the group consisting of 0, 1 and 2, more preferred x is selected from the group consisting of 0 and 1 and most preferred x is 0, or 1, preferably 0.
69. The GLP-1 derivative according to any of the embodiments 52-63, wherein —B— is

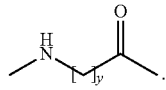

70. The GLP-1 derivative according to embodiment 69, wherein y is selected from the group consisting of 2, 3, 4, 5, 6, 7, 8, 9 and 10 and more preferred y is selected from the group consisting of 2, 3, 4, 5, 6, 7, and 8.
71. The GLP-1 derivative according to any of the embodiments 52-70, wherein —C— is

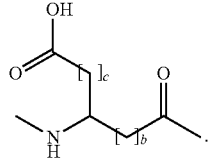

72. The GLP-1 derivative according to embodiment 71, wherein c is selected from the group consisting of 0 and 1 and b is selected from the group consisting of 1 and 2, more preferred b is 1, or 2, preferably 2; and c is 0.

73. The GLP-1 derivative according to any of the embodiments 52-70, wherein —C— is

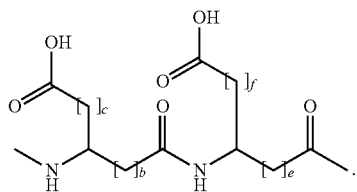

74. The GLP-1 derivative according to embodiment 73, wherein f is selected from the group consisting of 0 and 1 and e is selected from the group consisting of 1 and 2, more preferred e is 1 and f is 0.
75. The GLP-1 derivative according to any of the embodiments 52-70, wherein —C— is

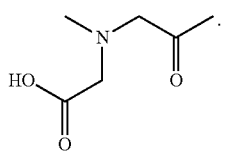

76. The GLP-1 derivative according to any of the embodiments 52-70, wherein D is selected from the group consisting of

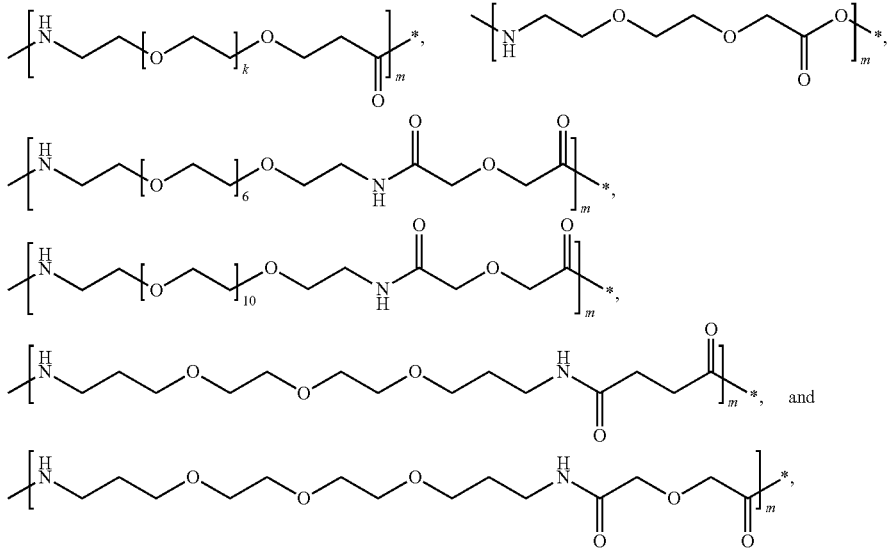

and wherein k is selected from the group consisting of 0, 1, 2, 3, 4, 5, 11 and 27, and m is selected from the group consisting of 0, 1, 2, 3, 4, 5 and 6.
77. The GLP-1 derivative according to any of the embodiments 52-76, wherein -D- is

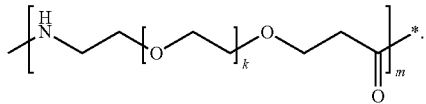

78. The GLP-1 derivative according to embodiment 77, wherein k is selected from the group consisting of 1, 2, 3, 11 and 27 and more preferred k is 1.
79. The GLP-1 derivative according to any of the embodiments 77-78, wherein m is selected from the group consisting of 0, 1, 2, 3, and 4 and more preferred m is selected from the group consisting of 0, 1 and 2.

80. The GLP-1 derivative according to any of the embodiments 52-76, wherein -D- is

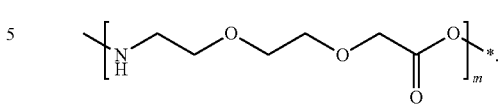

81. The GLP-1 derivative according to embodiment 80, wherein m is selected from the group consisting of 0, 1, 2, 3, and 4 and more preferred m is selected from the group consisting of 0, 1 and 2.
82. The GLP-1 derivative according to any of the embodiments 52-76, wherein -D- is

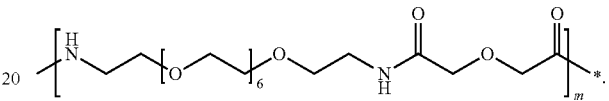

83. The GLP-1 derivative according to embodiment 82, wherein m is selected from the group consisting of 0, 1, 2, 3, and 4 and more preferred m is selected from the group consisting of 0, 1 and 2.
84. The GLP-1 derivative according to any of the embodiments 52-76, wherein -D- is

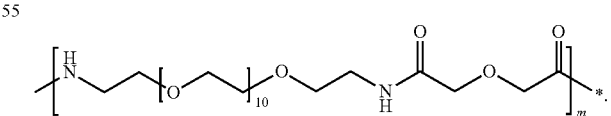

85. The GLP-1 derivative according to embodiment 84, wherein m is selected from the group consisting of 0, 1, 2, 3, and 4 and more preferred m is selected from the group consisting of 0, 1 and 2.
86. The GLP-1 derivative according to any of the embodiments 52-76, wherein -D- is

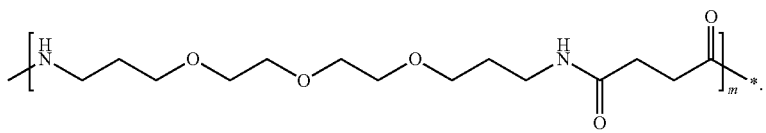

87. The GLP-1 derivative according to embodiment 86, wherein m is selected from the group consisting of 0, 1, 2, 3, and 4 and more preferred m is selected from the group consisting of 0, 1 and 2.
88. The GLP-1 derivative according to any of the embodiments 52-76, wherein -D- is

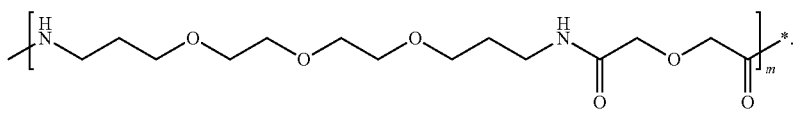

89. The GLP-1 derivative according to embodiment 88, wherein m is selected from the group consisting of 0, 1, 2, 3, and 4 and more preferred m is selected from the group consisting of 0, 1 and 2.
90. The GLP-1 derivative according to any of the embodiments 52-76, wherein A-B-C-D- is selected and combined from

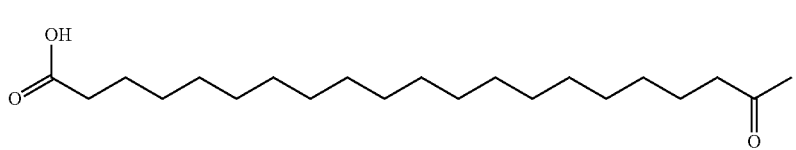

A

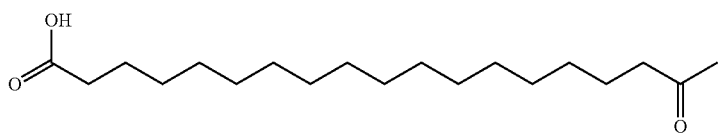

B

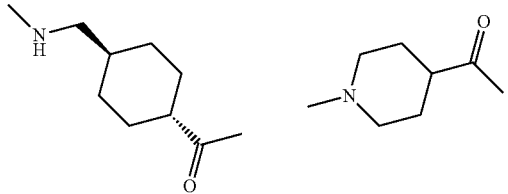

C

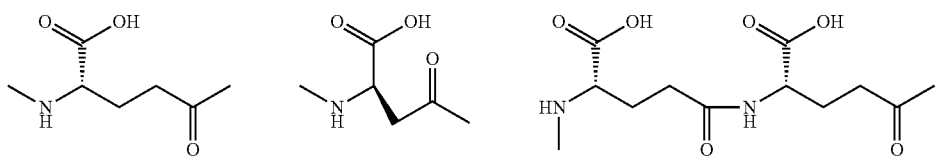

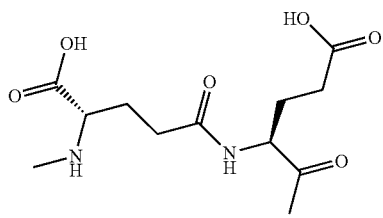

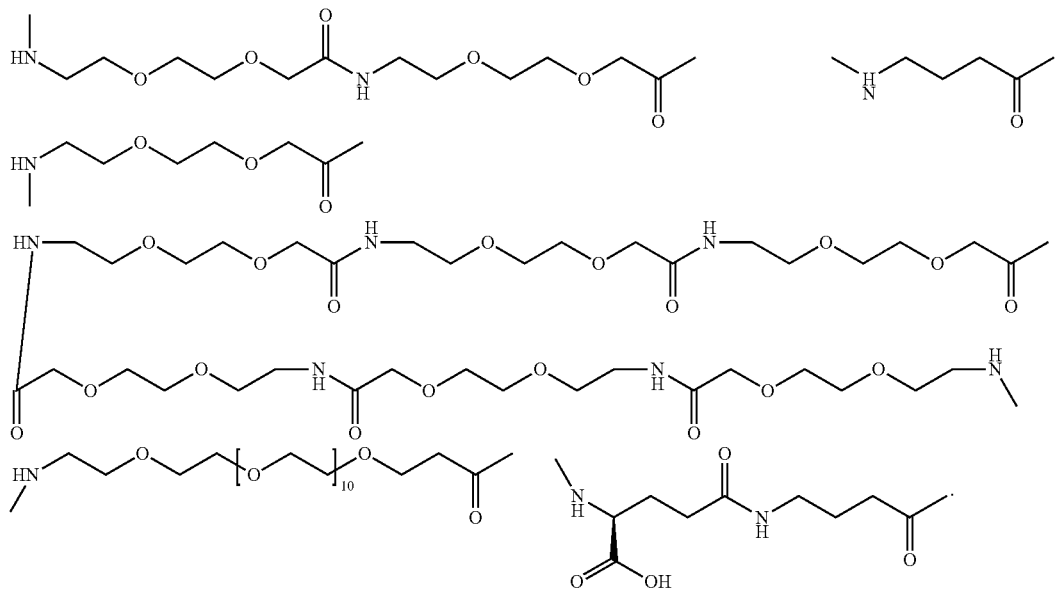
91. The GLP-1 derivative according to any of the embodiments 52-76, wherein A-B-C-D- is selected and combined from
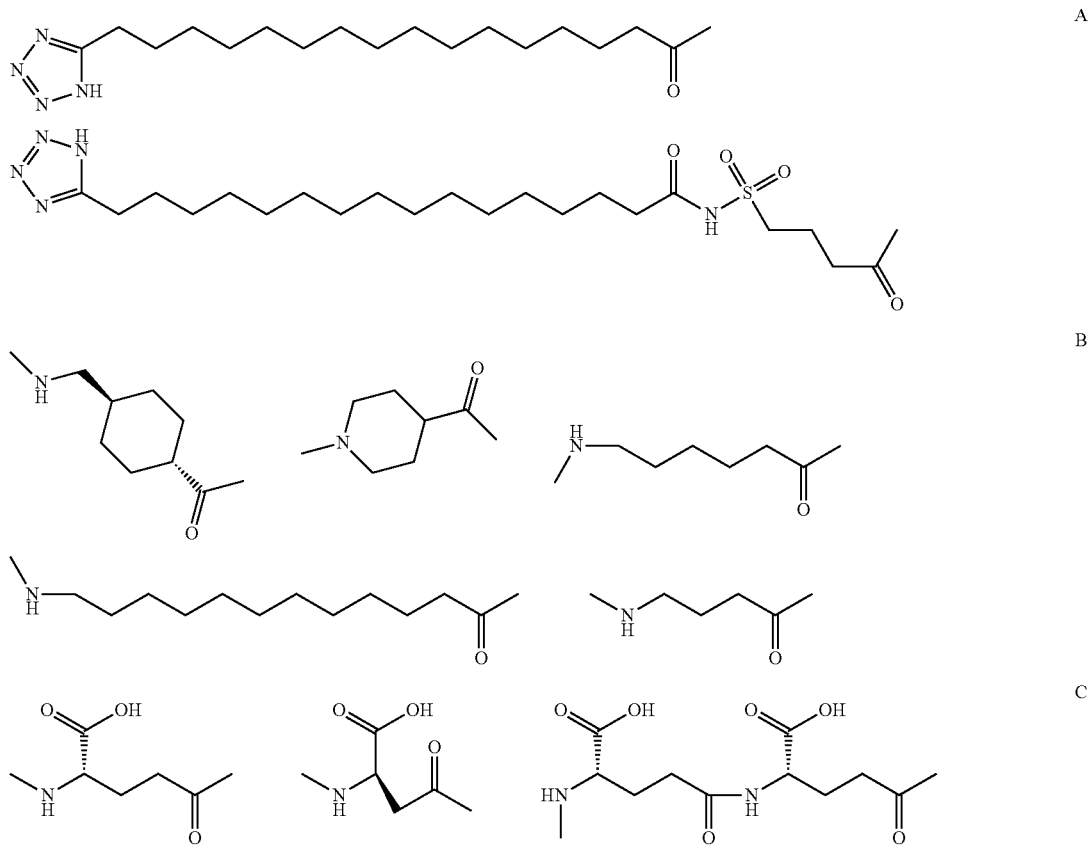

-continued
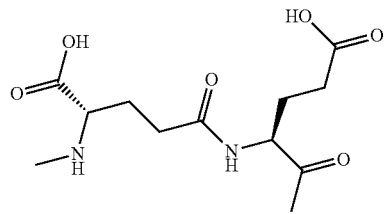
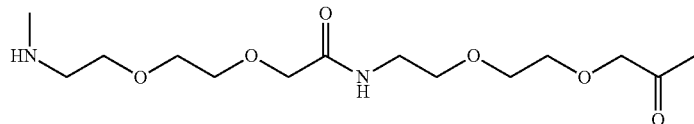
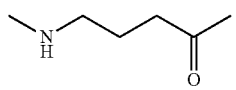
D
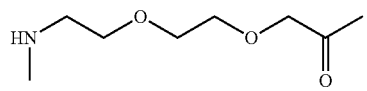
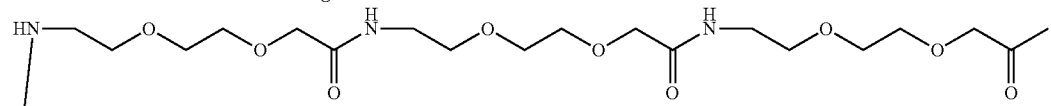
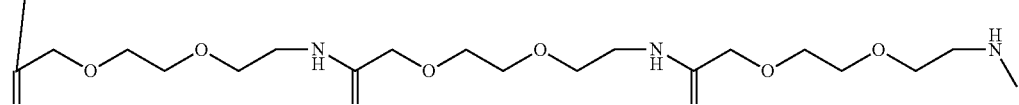
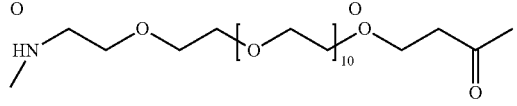
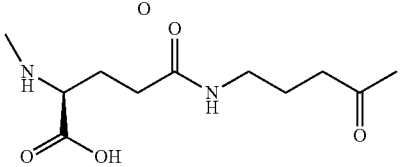
92. The GLP-1 derivative according to any of the embodiments 52-76, wherein A-B-C-D- is selected from the group consisting of
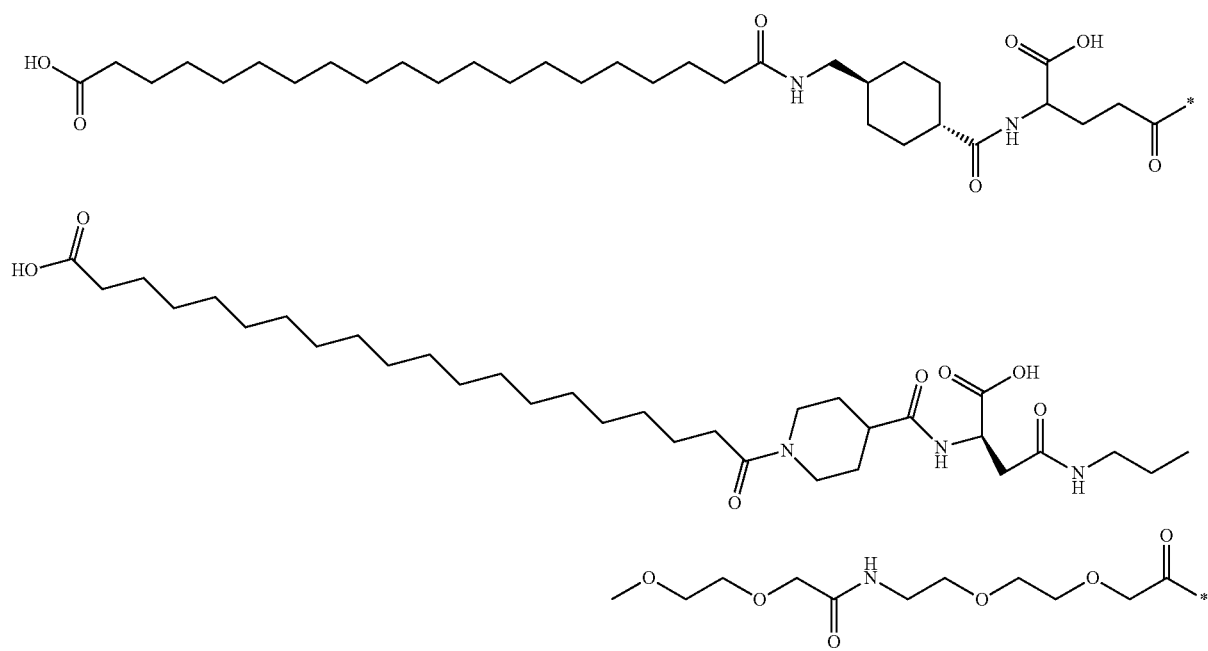

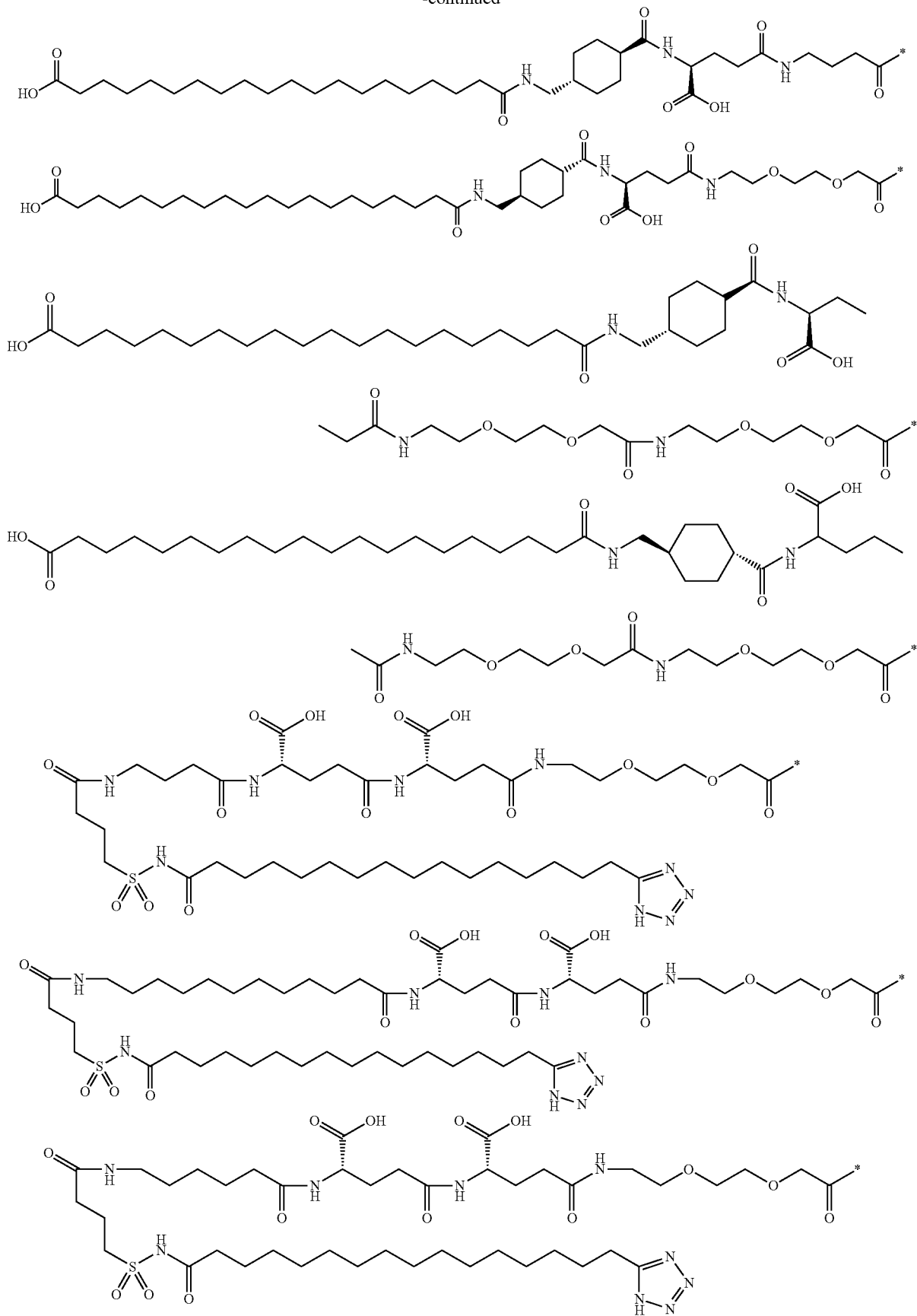

53 54
-continued
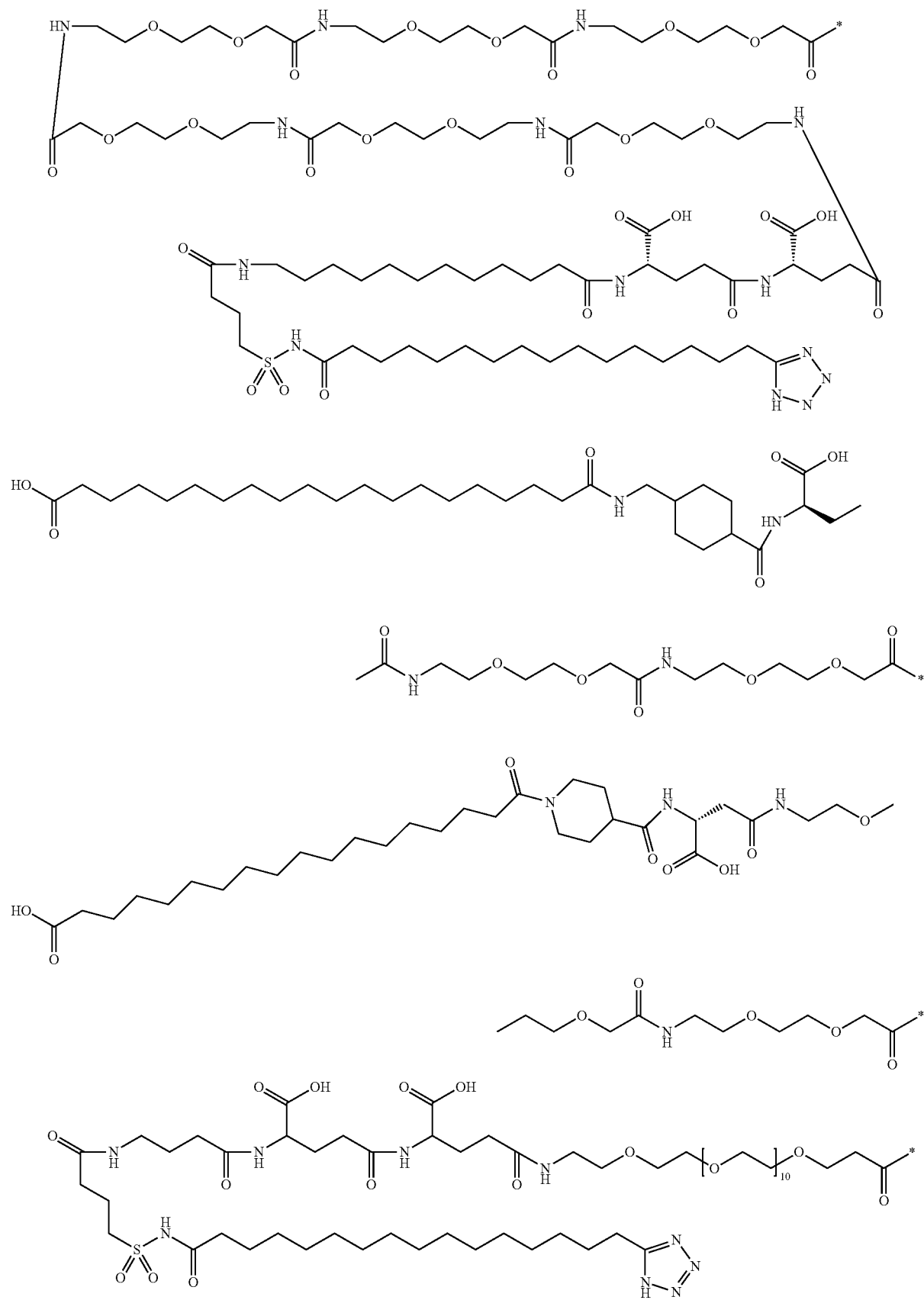

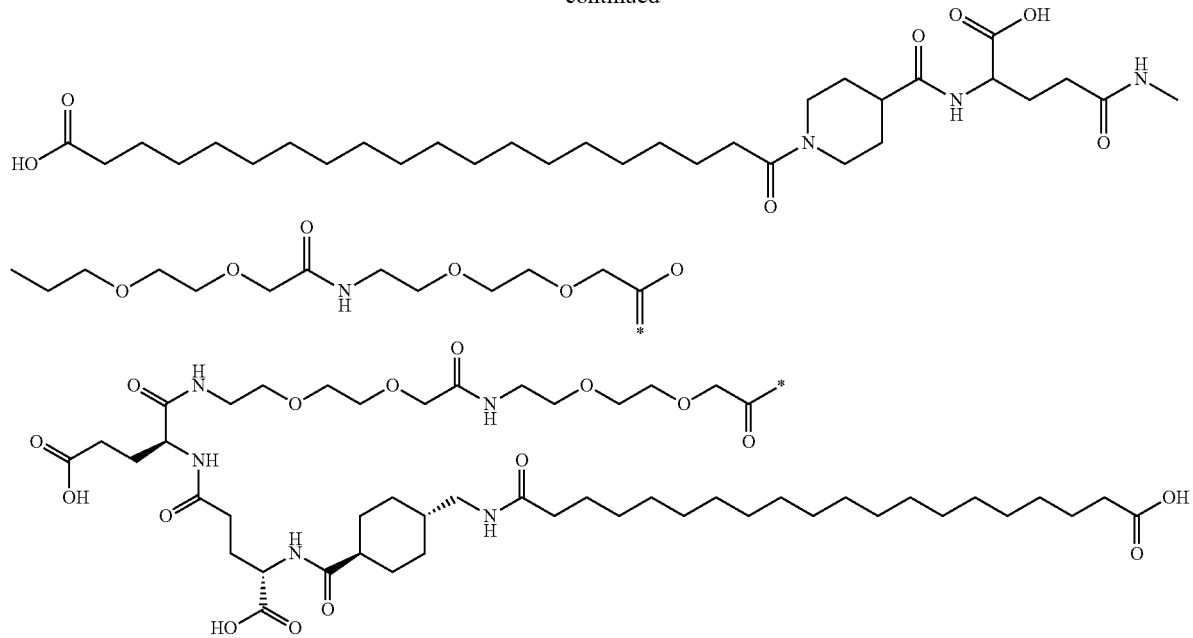

93. The derivative according to any of the above embodiments, which is selected from the group consisting of
N-epsilon37{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis7,Glu22,Arg26,Arg34,Lys37]GLP-1(7-37)amide,
N-epsilon37{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Arg34,Lys37]GLP-1-(7-37)amide,
N-epsilon37-[2-(2-[2-(2-[2-(2-((R)-3-[1-(17-Carboxyheptadecanoyl)piperidin-4-ylcarbonylamino]3-carboxypropionylamino)ethoxy)ethoxy]acetylamino)ethoxy]ethoxy)acetyl][,DesaminoHis7, Glu22 Arg26, Arg 34, Phe(m-CF3)28]GLP-1-(7-37)amide,
N-epsilon30{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Lys30]GLP-1-(7-37),
N-epsilon31{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8, Glu22, Arg26,Lys 31]GLP-1-(7-37),
N-epsilon31-(2-{2-[2-(2-{2-[2-((S)-3-Carboxy-3-{[1-(19-carboxy-nonadecanoyl)piperidine-4-carbonyl]amino}propionylamino)ethoxy]ethoxy}acetylamino)ethoxy]ethoxy}acetyl)[Aib8,Glu22,Arg26,Lys31,Arg34]GLP-1-(7-37),
N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl] [Aib8,Glu22,Arg26,Arg34,Lys37]GLP-1-(7-37)amide,
N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl] [DesaminoHis7,Glu22,Arg26,Arg34,Lys37]GLP-1-(7-37)amide,
N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl] [DesaminoHis7,Glu22,Arg26,Arg34,Lys37]GLP-1-(7-37),
N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl] [DesaminoHis7,Glu22,Arg26,Glu30,Arg34,Lys37]GLP-1-(7-37),
N-epsilon20-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys20,Glu22,Arg26,Glu30,Pro37]GLP-1-(7-37)amide,
N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Glu22,Arg26,Arg34,Lys37]GLP-1-(7-37)amide,
N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Glu22,Arg26,Arg34,Lys37]GLP-1-(7-37)amide,
[Aib8,Glu22,Arg26,Glu30,Pro37]GLP-1-(7-37)Lys [2-(2-{2-[4-Carboxy-4-(4-carboxy-4-{4-[4-(16-1H-tetrazol-5-yl-hexadecanoylsulfamoyl)butyrylamino]butyrylamino}butyrylamino)butyrylamino]ethoxy}ethoxy)acetyl],
N-epsilon37 (Polyethyleneglyco12000)[DesaminoHis7, Glu22,Arg26,Arg34,Lys37]GLP-1 (7-37) amide, N-epsilon37 (3-((2-(2-(2-(2-(2-Hexadecyloxyethoxy)ethoxy) ethoxy)ethoxy)ethoxy))propionyl)[Desamino-His7,Glu22,Arg26,Arg34,Lys37]GLP-1(7-37)-amide, N-epsilon37-{2-(2-(2-(2-[2-(2-(4-(hexadecanoylamino)-4-carboxybutyrylamino)ethoxy)ethoxy]acetyl)ethoxy) ethoxy)acetyl)}-[desaminoHis7,Glu22,Arg26, Glu30, Arg34,Lys37] (GLP-1-(7-37)amide, N-epsilon37-{2-(2-(2-(2-[2-(2-(4-(hexadecanoylamino)-4-carboxybutyrylamino)ethoxy)ethoxy]acetyl)ethoxy) ethoxy)acetyl)}-[desaminoHis7,Glu22, Arg26,Arg34,Lys 37] (GLP-1-(7-37)amide, N-epsilon37-(2-(2-(2-(2-(2-(2-(2-(2-(2-(Octadecanoylamino)ethoxy)ethoxy)acetylamino)ethoxy)ethoxy)acetylamino)ethoxy) ethoxy)acetyl][desaminoHis7,Glu22, Arg26,Arg34,Lys37] GLP-1 (7-37)amide, N-epsilon36-(2-(2-(2-((2-[2-(2-(17-carboxyheptadecanoylamino)ethoxy)ethoxy]acetylamino)ethoxy)ethoxy) acetyl) [Aib8,Glu22,Arg26,Glu30,Lys36] GLP-1-(7-37) Glu-amide, N-epsilon37-[4-(16-(1H-Tetrazol-5-yl)hexadecanoylsulfamoyl)butyryl][DesaminoHis7,Glu22,Arg26,Arg34, Lys37]GLP-1-(7-37)amide, N-epsilon37-[2-(2-{2-[2-(2-{2-[(S)-4-Carboxy-4-(19-carboxynonadecanoylamino)butyrylamino]ethoxy}ethoxy) acetylamino]ethoxy}ethox y)acetyl][DesaminoHis7, Glu22,Arg26,Arg34,Lys37]GLP-1-(7-37), and N-epsilon31-[2-(2-{2-[2-(2-{2-[4-Carboxy-4-(17-carboxyheptadecanoylamino)butyrylamino]ethoxy}ethoxy) acetylamino]ethoxy}ethoxy)acetyl][Aib8,Glu22,Arg26, Lys31]GLP-1-(7-37).

94. A method for increasing the time of action in a patient of a GLP-1 analogue, characterised in that a modified GLP-1 sequence 7-37 (SEQ ID No 1) is derivatised or pegylated as disclosed in any of the preceding embodiments.

95. A method for increasing the time of action in a patient of a GLP-1 derivative to more than about 40 hours, characterised in that a modified GLP-1 sequence 7-37 (SEQ ID No 1) is derivatised or pegylated as disclosed in any of the preceding embodiments.

96. A pharmaceutical composition comprising a derivative according to any one of embodiments 1-93, and a pharmaceutically acceptable excipient.

97. The pharmaceutical composition according to embodiment 96, which is suited for parenteral administration.

98. Use of a derivative according to any one of the embodiments 1-93 for the preparation of a medicament.

99. Use of a derivative according to any one of the embodiments 1-93 for the preparation of a medicament for the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers.

100. Use of a derivative according to any one of the embodiments 1-93 for the preparation of a medicament for delaying or preventing disease progression in type 2 diabetes.

101. Use of a derivative according to any one of the embodiments 1-93 for the preparation of a medicament for decreasing food intake, decreasing β-cell apoptosis, increasing β-cell function and β-cell mass, and/or for restoring glucose sensitivity to β-cells.

102. A derivative according to any one of the embodiments 1-93 for use in the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers.

Further Particular Embodiments According to the Invention

1. A GLP-1 derivative which comprises a modified GLP-1(7-37) sequence having:
   i) a total of 2-12 amino acid modifications as compared to GLP-1(7-37) (SEQ ID No: 1), including
      a) a Glu residue at a position equivalent to position 22 of GLP-1(7-37), and
      b) an Arg residue at a position equivalent to position 26 of GLP-1(7-37); and
   ii) which is derivatised with an albumin binding residue or pegylated in a position selected from a position equivalent to position 18, 20, 23, 30, 31, 34, 36, 37, or 39 of GLP-1(7-37).

2. The GLP-1 derivative according to embodiment 1 which comprises 2, 3, 4, 5, 6, 7, 8, 9, 10, 11, or 12 amino acid modifications; preferably 4-12, such as 4, 5, 6, 7, 8, 9, 10, 11, or 12 amino acid modifications; or such as 4, 5, 6, 7, 8, 9, or 12 amino acid modifications; more preferably 5-11 amino acid modifications; even more preferably 6-10 amino acid modifications; most preferably 7-9 amino acid modifications.

3. The GLP-1 derivative according to any one of embodiments 1-2 which comprises 2-8, preferably 2, 3, 4, 5, 6, 7, or 8, amino acid substitutions as compared to GLP-1(7-37) (SEQ ID No: 1).

4. The GLP-1 derivative according to embodiment 3 which comprises 3-8, preferably 4-8, more preferably 5-8, even more preferably 6-8, and most preferably 7-8 amino acid substitutions.

5. The GLP-1 derivative according to embodiment 3 which comprises i) 4, ii) 5, iii) 6, iv) 7, or v) 8 amino acid substitutions.

6. The GLP-1 derivative according to any one of embodiments 3-5 which is substituted at one or more of positions 7, 8, 20, 25, 28, 30, 31, 34, 35, 36, or 37, preferably at position 7 and/or 8.

7. The GLP-1 derivative according to any one of embodiments 1-6 which comprises a non-natural amino acid at position 7 or 8.

8. The GLP-1 derivative according to embodiment 7, which comprises 7-Desamino-histidine or 8-Aib.

9. The GLP-1 derivative according to any one of embodiments 1-7, which comprises one or more of 7-Desamino-histidine, 8-Aib, 20K, 25V, 28F(m-CF$_3$), 30E, 30K, 31K, 34-Dap, 34R, 35-Aib, 35K, 35R, 36K, 37K, 37K-epsilon, 37P, and/or 37R.

10. The GLP-1 derivative according to any one of embodiments 1-9 which comprises 1-3, preferably 1, 2, or 3, amino acid deletions as compared to GLP-1(7-37) (SEQ ID No: 1).

11. The GLP-1 derivative according to embodiment 10 wherein the deletion is C-terminal.

12. The GLP-1 derivative according to embodiment 11 which is a GLP-1(7-36), a GLP-1(7-35), or a GLP-1(7-34) derivative.

13. The GLP-1 derivative according to any one of embodiments 1-9 which comprises 1-4, preferably 1, 2, 3, or 4, amino acid additions as compared to GLP-1(7-37) (SEQ ID No: 1).

14. The GLP-1 derivative according to embodiment 13 wherein the addition is C-terminal.

15. The GLP-1 derivative according to embodiment 14 which is a GLP-1(7-38), a GLP-1(7-39), a GLP-1(7-40), or a GLP-1(7-41) derivative.

16. The GLP-1 derivative according to any one of the embodiments 1-15 which has (i) a C-terminal amide group; or (ii) a C-terminal carboxylic acid group, preferably a free carboxylic acid group (—COOH), or a salt thereof.

17. A GLP-1 derivative, preferably according to any one of the embodiments 1-16, having the sequence of formula (I)

```
Formula (I)
                                            (SEQ ID No: 2)
Xaa7-Xaa8-Xaa9-Gly-Thr-Phe-Thr-Ser-Asp-Xaa16-Ser- Xaa18-Tyr-Xaa20-Glu-Glu-Xaa23-Xaa24-Xaa25-Arg-Xaa27-

Xaa28-Ile-Xaa30-Xaa31-Leu-Xaa33-Xaa34-Xaa35-Xaa36-

Xaa37-Xaa38-Xaa39-Xaa40-Xaa41-R
``` wherein
($Xaa_7$-$Xaa_8$) is (L-histidine-Aib), (desamino-histidine-alanine), or (desamino-histidine-Aib);
$Xaa_9$ is Glu, or a Glu derivative such as alpha, alpha dimethyl-Glu;
$Xaa_{16}$ is Val, or Leu;
$Xaa_{18}$ is Ser, Lys, Cys, or Arg;
$Xaa_{20}$ is Leu, or Lys;
$Xaa_{23}$ is Gln, Glu, Lys, Cys, or Arg;
$Xaa_{24}$ is Ala, or Asn;
$Xaa_{25}$ is Ala, or Val;
$Xaa_{27}$ is Glu, Ala, or Leu;
$Xaa_{28}$ is Phe, or a Phe derivative such as m-$CF_3$-Phe;
$Xaa_{30}$ is Ala, Glu, Lys, or Arg;
$Xaa_{31}$ is Trp, Cys, or Lys;
$Xaa_{33}$ is Val, Cys, or Lys;
$Xaa_{34}$ is Lys, Cys, Glu, Asn, Dap, or Arg;
$Xaa_{35}$ is Gly, Arg, Lys, Aib, or absent;
$Xaa_{36}$ is Arg, Lys, or absent;
$Xaa_{37}$ is Gly, Aib, Cys, Lys, epsilon-amino-Lys, Pro, Arg, or absent;
$Xaa_{38}$ is Lys, Glu, Arg, or absent;
$Xaa_{39}$ is Lys, Arg, or absent;
$Xaa_{40}$ is Arg, or absent;
$Xaa_{41}$ is Arg, or absent; and
R is amide, or absent;
provided that if $Xaa_{37}$, $Xaa_{38}$, $Xaa_{39}$, or $Xaa_{40}$ is absent, then each amino acid residue downstream is also absent;
and which is derivatised with an albumin binding residue or pegylated in a position selected from a position equivalent to position 18, 20, 23, 30, 31, 34, 36, 37, 38, or 39 of GLP-1(7-37) (SEQ ID No: 1).

18. The GLP-1 derivative according to embodiment 17, wherein
($Xaa_7$-$Xaa_8$) is (L-histidine-Aib), or (desamino-histidine-alanine);
$Xaa_9$ is Glu;
$Xaa_{16}$ is Val;
$Xaa_{18}$ is Ser;
$Xaa_{20}$ is Leu, or Lys;
$Xaa_{23}$ is Gln;
$Xaa_{24}$ is Ala;
$Xaa_{25}$ is Ala, or Val;
$Xaa_{27}$ is Glu;
$Xaa_{28}$ is Phe, or a Phe derivative such as m-$CF_3$-Phe;
$Xaa_{30}$ is Ala, Glu, or Lys;
$Xaa_{31}$ is Trp, or Lys;
$Xaa_{33}$ is Val;
$Xaa_{34}$ is Lys, Dap, or Arg;
$Xaa_{35}$ is Gly, Arg, Lys, Aib, or absent;
$Xaa_{36}$ is Arg, Lys, or absent;
$Xaa_{37}$ is Gly, Lys, epsilon-amino-Lys, Pro, Arg, or absent;
$Xaa_{38}$ is Lys, Glu, Arg, or absent;
$Xaa_{39}$ is Lys, Arg, or absent;
$Xaa_{40}$ is Arg, or absent;
$Xaa_{41}$ is Arg, or absent; and
R is amide, or absent;
provided that if $Xaa_{37}$, $Xaa_{38}$, $Xaa_{39}$, or $Xaa_{40}$ is absent, then each amino acid residue downstream is also absent;
and which is derivatised with an albumin binding residue or pegylated in a position selected from a position equivalent to position 18, 20, 23, 30, 31, 34, 36, 37, 38, or 39 of GLP-1(7-37) (SEQ ID No: 1).

19. A GLP-1 derivative, preferably according to any one of embodiments 1-18, having the sequence of formula (II)

```
Formula (II)
                                            (SEQ ID No: 3)
Xaa7-Xaa8-Glu-Gly-Thr-Phe-Thr-Ser-Asp-Val-Ser- Xaa18-Tyr-Leu-Glu-Glu-Gln-Ala-Ala-Arg-Glu- Phe-Ile-Xaa30-Xaa31-Leu-Xaa33-Xaa34-Xaa35-Xaa36-

Xaa37-Xaa38-Xaa39-Xaa40-Xaa41-R
``` wherein
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine, or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{18}$ is Ser, Lys, or Arg;
$Xaa_{30}$ is Ala, Glu, Lys, or Arg;
$Xaa_{31}$ is Lys, or Trp;
$Xaa_{33}$ is Val or Lys;
$Xaa_{34}$ is Lys, Glu, Dap, or Arg;
$Xaa_{35}$ is Gly, Arg, Lys Aib, or absent;
$Xaa_{36}$ is Arg, Lys, or absent;
$Xaa_{37}$ is Gly, Aib, Lys, epsilon-amino-Lys, Pro, Arg, or absent;
$Xaa_{38}$ is Lys, Glu, Arg, or absent;
$Xaa_{39}$ is Lys, Arg, or absent;
$Xaa_{40}$ is Arg, or absent;
$Xaa_{41}$ is Arg, or absent; and
R is amide, or is absent;
provided that if $Xaa_{37}$, $Xaa_{38}$, $Xaa_{39}$, or $Xaa_{40}$ is absent, then each amino acid residue downstream is also absent;
and which is derivatised with an albumin binding residue or pegylated in a position selected from a position equivalent to position 18, 20, 23, 30, 31, 34, 36, 37, 38, or 39 of GLP-1(7-37) (SEQ ID No: 1).

20. The GLP-1 derivative according to embodiment 19, wherein
$Xaa_7$ is L-histidine, or desamino-histidine;
$Xaa_8$ is Ala, or Aib;
$Xaa_{18}$ is Ser;
$Xaa_{30}$ is Ala, Glu, or Lys;
$Xaa_{31}$ is Lys, or Trp;
$Xaa_{33}$ is Val;
$Xaa_{34}$ is Lys, Dap, or Arg;
$Xaa_{35}$ is Gly, Arg, Lys Aib, or absent;
$Xaa_{36}$ is Arg, Lys, or absent;
$Xaa_{37}$ is Gly, Lys, epsilon-amino-Lys, Pro, Arg, or absent;
$Xaa_{38}$ is Lys, Glu, Arg, or absent;
$Xaa_{39}$ is Lys, Arg, or absent;
$Xaa_{40}$ is Arg, or absent;
$Xaa_{41}$ is Arg, or absent; and
R is amide, or is absent;

provided that if Xaa_{37}, Xaa_{38}, Xaa_{39}, or Xaa_{40} is absent, then each amino acid residue downstream is also absent;
and which is derivatised with an albumin binding residue or pegylated in a position selected from a position equivalent to position 18, 20, 23, 30, 31, 34, 36, 37, 38, or 39 of GLP-1(7-37) (SEQ ID No: 1).

21. The GLP-1 derivative according to any one of embodiments 1-20 which is derivatised in one position.

22. The GLP-1 derivative according to any one of embodiments 1-20 which is derivatised in one or more positions, preferably in two position, in three positions, or in four positions.

23. The GLP-1 derivative according to any one of embodiments 1-22 which is derivatised in i) position 18, ii) position 20, iii) position 23, iv) position 30, v) position 31, vi) position 34, vii) position 36, viii) position 37, ix) position 38, and/or x) position 39.

24. The GLP-1 derivative according to any one of embodiments 1-23 which is derivatised in i) position 20, ii) position 30, iii) position 31, iv) position 36, v) position 37, vi) position 38, or vii) position 39.

25. The GLP-1 derivative according to any one of embodiments 1-24 which is PEGylated.

26. The GLP-1 derivative according to any one of embodiments 1-24 wherein the albumin binding residue is selected from i) straight chain alkyl, preferably C15 alkyl; ii) acyl of the formula $CH_3(CH_2)_rCO—$, wherein preferably r is 14 or 16.

27. The GLP-1 derivative according to any one of embodiments 1-24 and 26 which includes a linker between the albumin binding residue and GLP-1 moiety, wherein the linker comprises, preferably is,
i) one or more alkylene glycol units such as 1-10, preferably 5-8, more preferably 6;
ii) a compound C of formula X wherein c is 0 and b is 2;
iii) a compound of formula XVI wherein q is 1 or 2; or
iv) any combination of i)-iii), such as a combination of ii) and iii).

28. A GLP-1 derivative, preferably according to any one of the embodiments 1-27, wherein at least one amino acid residue is derivatised with A-B-C-D-
wherein A- is selected from the group consisting of

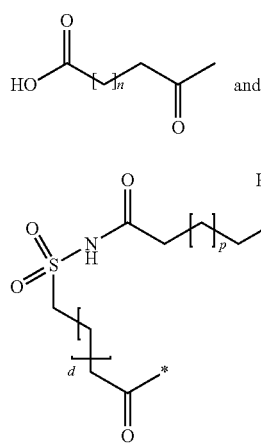

wherein the tetrazole ring is optionally N-substituted, and wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, —B— is selected from the group consisting of

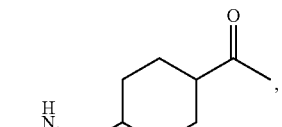

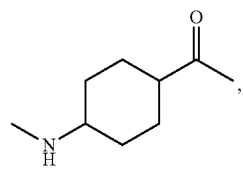

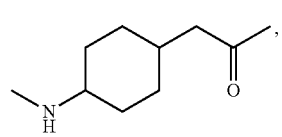

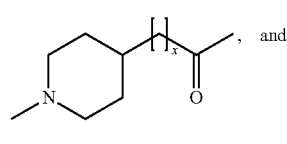

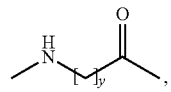

wherein x is selected from the group consisting of 0, 1, 2, 3 and 4, and y is selected from the group consisting of 1, 2, 3, 4, 5, 6, 7, 8, 9, 10, 11 and 12, —C— is selected from the group consisting of

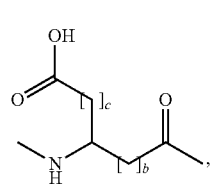

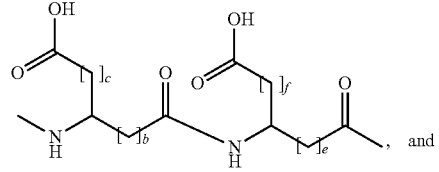

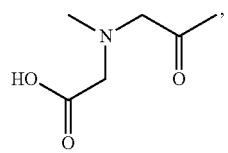

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker.

29. The GLP-1 derivative according to any one of embodiments 1-28, wherein the derivatised amino acid residue is lysine, which is preferably derivatised via the epsilon amino group.

30. A GLP-derivative, preferably according to any one of embodiments 1-29, which is selected from the following:

N-epsilon37{2-[2-(2-{2-[2-((R)-3-carboxy-3-{[1-(19-carboxynonadecanoyl)piperidine-4-carbon yl]amino}propionylamino)ethoxy]ethoxy}acetylamino) ethoxy]ethoxy}acetyl [desaminoHis7,Glu22,Arg26, Arg34,Lys37]GLP-1(7-37)amide;

N-epsilon37{2-[2-(2-{2-[2-((S)-3-carboxy-3-{[1-(19-carboxynonadecanoyl)piperidine-4-carbonyl] amino}propionylamino)ethoxy]ethoxy}acetylamino) ethoxy]ethoxy}acetyl [Aib8,Glu22,Arg26,Arg34,Lys37] GLP-1-(7-37)amide;

N-epsilon37-[2-(2-[2-(2-[2-(2-((R)-3-[1-(17-Carboxyheptadecanoyl)piperidin-4-ylcarbonylamino]3-carboxypropionylamino)ethoxy)ethoxy]acetylamino)ethoxy]ethoxy) acetyl][DesaminoHis 7,Glu22,Arg26,Arg34,Phe(m-CF3) 28]GLP-1-(7-37)amide;

N-epsilon30{2-[2-(2-{2-[2-((S)-3-carboxy-3-{[1-(19-carboxynonadecanoyl)piperidine-4-carbonyl] amino}propionylamino)ethoxy]ethoxy}acetylamino) ethoxy]ethoxy}acetyl [Aib8,Glu22,Arg26,Lys30]GLP-1-(7-37);

N-epsilon31{2-[2-(2-{2-[2-((S)-3-carboxy-3-{[1-(19-carboxynonadecanoyl)piperidine-4-carbonyl] amino}propionylamino)ethoxy]ethoxy}acetylamino) ethoxy]ethoxy}acetyl [Aib8,Glu22,Arg26,Lys31]GLP-1-(7-37);

N-epsilon31-(2-{2-[2-(2-{2-[2-((S)-3-Carboxy-3-{[1-(19-carboxy-nonadecanoyl)piperidine-4-carbonyl] amino}propionylamino)ethoxy]ethoxy}acetylamino) ethoxy]ethoxy}acetyl)[Aib8,Glu22,Arg26,Lys31,Arg34] GLP-1-(7-37);

N-epsilon37-[2-(2-{2-[2-(2-{2-[(S)-4-Carboxy-4-({trans-4-[(19-carboxy-nonadecanoylamino)methyl] cyclohexanecarbonyl}amino)butyrylamino] ethoxy}ethoxy)acetylamino]ethoxy}ethoxy)acetyl] [Aib8,Glu22,Arg26,Arg34,Lys37]GLP-1-(7-37)amide;

N-epsilon37-[2-(2-{2-[2-(2-{2-[(S)-4-Carboxy-4-({trans-4-[(19-carboxy-nonadecanoylamino)methyl] cyclohexanecarbonyl}amino)butyrylamino] ethoxy}ethoxy)acetylamino]ethoxy}ethoxy)acetyl] [DesaminoHis7,Glu22,Arg26,Arg34,Lys37]GLP-1-(7-37)amide;

N-epsilon37-[2-(2-{2-[2-(2-{2-[(S)-4-Carboxy-4-({trans-4-[(19-carboxy-nonadecanoylamino)methyl] cyclohexanecarbonyl}amino)butyrylamino] ethoxy}ethoxy)acetylamino]ethoxy}ethoxy)acetyl] [DesaminoHis7,Glu22,Arg26,Arg34,Lys37]GLP-1-(7-37);

N-epsilon37-[2-(2-{2-[2-(2-{2-[(S)-4-Carboxy-4-({trans-4-[(19-carboxy-nonadecanoylamino)methyl] cyclohexanecarbonyl}amino)butyrylamino] ethoxy}ethoxy)acetylamino]ethoxy}ethoxy)acetyl] [DesaminoHis7,Glu22,Arg26,Glu30,Arg34,Lys37]GLP-1-(7-37);

N-epsilon20-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Lys20,Glu22,Arg26, Glu30,Pro37]GLP-1-(7-37)amide);

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Glu22,Arg26,Arg34, Lys37]GLP-1-(7-37)amide;

N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Glu22, Arg26,Arg34,Lys37]GLP-1-(7-37)amide;

[Aib8,Glu22,Arg26,Glu30,Pro37]GLP-1-(7-37)Lys [2-(2-{2-[4-Carboxy-4-(4-carboxy-4-{4-[4-(16-1H-tetrazol-5-yl-hexadecanoylsulfamoyl)butyrylamino] butyrylamino}butyrylamino)butyrylamino] ethoxy}ethoxy)acetyl];

N-epsilon37 (Polyethyleneglycol2000)[DesaminoHis7, Glu22,Arg26,Arg34,Lys37]GLP-1 (7-37) amide;

N-epsilon37 (3-((2-(2-(2-(2-(2-Hexadecyloxyethoxy) ethoxy) ethoxy)ethoxy)ethoxy))propionyl)[DesaminoHis7,Glu22,Arg26,Arg34,Lys37]GLP-1(7-37)-amide;

N-epsilon37-{2-(2-(2-(2-[2-(2-(4-(hexadecanoylamino)-4-carboxybutyrylamino)ethoxy)ethoxy]acetyl)ethoxy) ethoxy)acetyl)}-[desaminoHis7,Glu22,Arg26, Glu30, Arg34,Lys37] (GLP-1-(7-37)amide N-epsilon37-{2-(2-(2-(2-[2-(2-(4-(hexadecanoylamino)-4-carboxybutyrylamino)ethoxy)ethoxy]acetyl)ethoxy) ethoxy)acetyl)}-[desaminoHis7,Glu22, Arg26,Arg34,Lys 37] (GLP-1-(7-37)amide;

N-epsilon37-(2-(2-(2-(2-(2-(2-(2-(2-(2-(Octadecanoylamino)ethoxy)ethoxy)acetylamino)ethoxy)ethoxy)acetylamino)ethoxy)eth oxy)acetyl)[desaminoHis7,Glu22, Arg26,Arg34,Lys37] GLP-1 (7-37)amide N-epsilon36-(2-(2-(2-((2-[2-(2-(17-carboxyheptadecanoylamino)ethoxy)ethoxy]acetylamino)ethoxy)ethoxy) acetyl) [Aib8,Glu22,Arg26,Glu30,Lys36] GLP-1-(7-37) Glu-amide;

N-epsilon37-[4-(16-(1H-Tetrazol-5-yl)hexadecanoylsulfamoyl)butyryl][DesaminoHis7,Glu22,Arg26,Arg34, Lys37]GLP-1-(7-37)amide;

N-epsilon37-[2-(2-{2-[2-(2-{2-[(S)-4-Carboxy-4-(19-carboxynonadecanoylamino)butyrylamino]ethoxy}ethoxy) acetylamino]ethoxy}ethoxy)acetyl][DesaminoHis7, Glu22,Arg26,Arg34,Lys37]GLP-1-(7-37);

N-epsilon31-[2-(2-{2-[2-(2-{2-[4-Carboxy-4-(17-carboxyheptadecanoylamino)butyrylamino]ethoxy}ethoxy) acetylamino]ethoxy}ethoxy)acetyl][Aib8,Glu22,Arg26, Lys31]GLP-1-(7-37);

N-epsilon20-(2-{2-[2-(2-{2-[2-((S)-4-Carboxy-4-hexadecanoylamino-butyrylamino)ethoxy]ethoxy}acetylamino) ethoxy]ethoxy}-acetyl)[Aib8,Lys20,Glu22,Arg26,Glu30, Pro37]GLP-1-(7-37)amide;

N-epsilon37-(2-{2-[2-((S)-4-Carboxy-4-{(S)-4-carboxy-4-[(S)-4-carboxy-4-(19-carboxy-nonadecanoylamino)butyrylamino]butyrylamino}butyrylamino)ethoxy] ethoxy}acetyl)[DesaminoHis7,Glu22,Arg26,Arg34, Lys37]GLP-1-(7-37);

N-epsilon37-{2-[2-(2-{(S)-4-[(S)-4-(12-{4-[16-(2-tert-Butyl-2H-tetrazol-5-yl)-hexadecanoylsulfamoyl] butyrylamino}dodecanoylamino)-4-carboxybutyrylamino]-4-carboxybutyrylamino}ethoxy)ethoxy]acetyl} [DesaminoHis7,Glu22,Arg26,Arg34,Lys37] GLP-1 (7-37);

N-epsilon37-[2-(2-{2-[2-(2-{2-[(S)-4-Carboxy-4-(17-carboxyheptadecanoylamino)-butyrylamino]-ethoxy}-ethoxy)-acetylamino]-ethoxy}-acetyl] [Aib8, Glu22,Arg26,Arg34,Lys37]GLP-1-(7-37).

N-alpha37-[2-(2-{2-[2-(2-{2-[(S)-4-Carboxy-4-(17-carboxy-heptadecanoylamino)-butyrylamino]-ethoxy}- ethoxy)-acetylamino]-ethoxy}-ethoxy)-acetyl] [Aib8, Glu22,Arg26,Arg34,epsilon-Lys37]GLP-1-(7-37) peptide;

N-epsilon37-[2-(2-{2-[2-(2-{2-[(S)-4-Carboxy-4-(17-car-boxy-heptadecanoylamino)-butyrylamino]-ethoxy}-ethoxy)-acetylamino]-ethoxy}-ethoxy)-acetyl] [desaminoHis7,Glu22,Arg26,Arg34,Lys37] GLP-1-(7-37);

N-epsilon36-[2-(2-{2-[2-(2-{2-[(S)-4-carboxy-4-(15-car-boxy-pentadecanoylamino)-butyrylamino]-ethoxy}-ethoxy)-acetylamino]-ethoxy}-ethoxy)-acetyl] [desaminoHis7, Glu22,Arg26,Glu30,Arg34,Lys36]GLP-1-(7-37)-Glu-Lys peptide;

[desaminoHis7,Glu22,Arg26,Glu30,Arg34]GLP-1-(7-37)-Glu-Lys(2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl)peptide;

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl] [Aib8,Glu22,Arg26,Arg34,Lys37]GLP-1-(7-37);

N-epsilon37-[2-(2-{2-[2-(2-{2-[(S)-4-carboxy-4-(17-car-boxy-heptadecanoylamino)-butyrylamino]-ethoxy}-ethoxy)-acetylamino]-ethoxy}-ethoxy)-acetylHAib8, Glu22, Arg26,Arg34,Aib35,Lys37]GLP-1-(7-37);

N-epsilon31-[2-(2-{2-[2-(2-{2-[(S)-4-Carboxy-4-(17-car-boxyheptadecanoylamino)butyrylamino]ethoxy}ethoxy)acetylamino]ethoxy}ethoxy)acetyl][Aib8,Glu22,Val25,Arg26,Lys31,Arg34,Arg35,Arg37]GLP-1-(7-37);

N-epsilon31{2-(2-{2-[2-(2-{2-[4-Carboxy-4-(17-carboxy-heptadecanoylamino)butyrylamino]ethoxy}ethoxy)acetylamino]ethoxy}ethoxy)acetyl}-[Aib8,Glu22,Val25,Arg26,Lys31,Arg34,Arg35,Arg37)]GLP-1(7-37)yl [Arg39,Arg40,Arg41];

N-epsilon31-[2-(2-{2-[2-(2-{2-[(S)-4-Carboxy-4-(17-car-boxyheptadecanoylamino)butyrylamino]ethoxy}ethoxy)acetylamino]ethoxy}ethoxy)acetyl][Aib8,Glu22,Val25,Arg26,Lys31,Lys35,Lys36]GLP-1-(7-36) amide;

N-epsilon31-{2-(2-{2-[2-(2-{2-[4-Carboxy-4-(17-carboxy-heptadecanoylamino)butyrylamino]ethoxy}ethoxy)acetyl-amino]ethoxy}ethoxy)acetyl}-N-beta34-(2-(bis-car-boxymethylamino)acetyl)[Aib8,Glu22,Val25,Arg26, Lys31,Dap34] GLP-1(7-34) amide; and N-epsilon-37-[(S)-4-carboxy-4-(2-{2-[2-(2-{2-[2-(17-car-boxyheptadecanoylamino) ethoxy]ethoxy}acetylamino) ethoxy]ethoxy}acetylamino) butyryl] [Aib8,Glu22, Arg26,34,Lys37] GLP-1 (7-37).

31. A pharmaceutical composition comprising a derivative according to any one of embodiments 1-30 or a pharmaceutically acceptable salt, amide, alkyl, or ester or the like thereof, and a pharmaceutically acceptable excipient.

32. A derivative according to any one of embodiments 1-30, or a pharmaceutical composition according to embodiment 31, for use as a medicament.

33. A derivative according to any one of embodiments 1-30, or a pharmaceutical composition according to embodiment 31, for use in the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

34. The derivative or pharmaceutical composition according to embodiment 33, for use in the treatment or prevention of type 2 diabetes.

35. Use of a derivative according to any one of embodiments 1-30, or a pharmaceutical composition according to embodiment 31, in the manufacture of a medicament for use in the treatment or prevention of hyperglycemia, type 2 diabetes, impaired glucose tolerance, type 1 diabetes, obesity, hypertension, syndrome X, dyslipidemia, cognitive disorders, atheroesclerosis, myocardial infarction, coronary heart disease and other cardiovascular disorders, stroke, inflammatory bowel syndrome, dyspepsia and gastric ulcers.

36. The use according to embodiment 35 for the treatment or prevention of type 2 diabetes.

37. A method of treating or preventing hyperglycemia, type 2 diabetes, impaired glucose tolerance, type 1 diabetes, obesity, hypertension, syndrome X, dyslipidemia, cognitive disorders, atheroesclerosis, myocardial infarction, coronary heart disease and other cardiovascular disorders, stroke, inflammatory bowel syndrome, dyspepsia and gastric ulcers by administering a pharmaceutically active amount of a derivative according to any one of embodiments 1-30, or a pharmaceutical composition according to embodiment 31.

38. The method according to embodiment 37 for treating or preventing type 2 diabetes.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a formulation described herein as comprising a particular element should be understood as also describing a formulation consisting of that element, unless otherwise stated or clearly contradicted by context).

This invention includes all modifications and equivalents of the subject matter recited in the embodiments, aspects or claims presented herein to the maximum extent permitted by applicable law.

The present invention is further illustrated in the following representative methods and examples which are, however, not intended to limit the scope of the invention in any way.

The features disclosed in the foregoing description and in the following examples may, both separately and in any combination thereof, be material for realising the invention in diverse forms thereof.

EXAMPLES

Abbreviations used:
r.t: Room temperature
DIPEA: diisopropylethylamine
$H_2O$: water
$CH_3CN$: acetonitrile
DMF: NN dimethylformamide
HBTU: 2-(1H-Benzotriazol-1-yl-)-1,1,3,3 tetramethyluronium hexafluorophosphate
Fmoc: 9H-fluoren-9-ylmethoxycarbonyl
Boc: tert butyloxycarbonyl
OtBu: tert butyl ester
tBu: tert butyl
Trt: triphenylmethyl
Pmc: 2,2,5,7,8-Pentamethyl-chroman-6-sulfonyl
Dde: 1-(4,4-Dimethyl-2,6-dioxocyclohexylidene)ethyl
ivDde: 1-(4,4-Dimethyl-2,6-dioxocyclohexylidene)-3-methylbutyl
Mtt: 4-methyltrityl
Mmt: 4-methoxytrityl
DCM: dichloromethane
TIS: triisopropylsilane)
TFA: trifluoroacetic acid
$Et_2O$: diethylether
NMP: 1-Methyl-pyrrolidin-2-one
DIPEA: Diisopropylethylamine
HOAt: 1-Hydroxy-7-azabenzotriazole
HOBt: 1-Hydroxybenzotriazole
DIC: Diisopropylcarbodiimide
MW: Molecular weight
A: Synthesis of Resin Bound Peptide
SPPS Method A.

The protected peptidyl resin was synthesized according to the Fmoc strategy on an Applied Biosystems 433 peptide synthesizer in 0.25 mmol or 1.0 mmol scale using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP (N-methyl pyrrolidone), and UV monitoring of the deprotection of the Fmoc protection group. The starting resin used for the synthesis of the peptide amides was Rink-Amide resin and either Wang or chlorotrityl resin was used for peptides with a carboxy C-terminal. The protected amino acid derivatives used were standard Fmoc-amino acids (supplied from e.g. Anaspec, or Novabiochem) supplied in preweighed cartridges suitable for the ABI433A synthesizer with the exception of unnatural aminoacids such as Fmoc-Aib-OH (Fmoc-aminoisobutyric acid). The N terminal amino acid was Boc protected at the alpha amino group (e.g. Boc-His(Boc)OH was used for peptides with His at the N-terminal). The epsilon amino group of lysine in position 26 was either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2002/2003 or newer version, or W.R. Sampson (1999), 3. Pep. Sci. 5, 403.

SPPS Method B:

One alternative method (method B) of peptide synthesis was by Fmoc chemistry on a microwave-based Liberty peptide synthesizer (CEM Corp., North Carolina). The resin was Tentagel S RAM with a loading of 0.24 mmol/g. The coupling chemistry was DIC/HOAt in NMP using amino acid solutions of 0.3 M in NMP and a molar excess of 8-10 fold. Coupling conditions was 5 minutes at up to 70° C. Deprotection was with 5% piperidine in NMP at up to 70° C. When a chemical modification of a lysine side chain was desired, the lysine was incorporated as Lys(Mtt). The Mtt group was removed by suspending the resin in neat hexafluoroisopropanol for 20 minutes followed by washing with DCM and NMP. The chemical modification of the lysine was performed either by manual synthesis or by one or more automated steps on the Liberty followed by a manual coupling. Another method of peptide synthesis was by Fmoc chemistry on an ABI 433 with HBTU coupling. After synthesis the resin was washed with DCM and dried, and the peptide was cleaved from the resin by a 2 hour treatment with TFA/TIS/water (92.5/5/2.5) followed by precipitation with diethylether. the peptide was redissolved in 30% acetic acid or similar solvent and purified by standard RP-HPLC on a C18 column using acetonitrile/TFA. The identity of the peptide was confirmed by MALDI-MS.

SPPS Method C

The protected peptidyl resin was synthesized according to the Fmoc strategy on an Advanced ChemTech Synthesiser (APEX 348) 0.25 mmol scale using the manufacturer supplied protocols which employ DIC (dicyclohexylcarbodiimide) and HOBt (1-Hydroxybenzotriazole) mediated couplings in NMP (N-methyl pyrrolidone. The starting resin used for the synthesis of the peptide amides was Rink-Amide resin and either Wang or chlorotrityl resin was used for peptides with a carboxy C-terminal. The protected amino acid derivatives used were standard Fmoc-amino acids (supplied from e.g. Anaspec, or Novabiochem. The N terminal amino acid was Boc protected at the alpha amino group (e.g. Boc-His(Boc)OH was used for peptides with His at the N-terminal). The epsilon amino group of lysine in position 26 was either protected with Mtt, Mmt, Dde, ivDde, or Boc, depending on the route for attachment of the albumin binding moiety and spacer. The synthesis of the peptides may in some cases be improved by the use of dipeptides, e.g., pseudoprolines from Novabiochem, Fmoc-Ser(tbu)-ΨSer(Me,Me)-OH, see e.g. catalogue from Novobiochem 2002/2003 or newer version, or W.R. Sampson (1999), 3. Pep. Sci. 5, 403

Procedure for Removal of ivDde or Dde-Protection.

The resin (0.25 mmol) was placed in a manual shaker/filtration apparatus and treated with 2% hydrazine in N-methyl pyrrolidone (20 ml, 2×12 min) to remove the Dde or ivDde group and wash with N-methyl pyrrolidone (4×20 ml).

Procedure for Removal of Mtt or Mmt-Protection.

The resin (0.25 mmol) was placed in a manual shaker/filtration apparatus and treated with 2% TFA and 2-3% TIS in DCM (20 ml, 5-10 min repeated 6-12 times) to remove the Mtt or Mmt group and wash with DCM (2×20 ml), 10% MeOH and 5% DIPEA in DCM (2×20 ml) and N-methyl pyrrolidone (4×20 ml).

Alternative Procedure for Removal of Mtt-Protection:

The resin was placed in a syringe and treated with hexafluroisopropanol for 2×10 min to remove the Mtt group. The resin was then washed with DCM and NMP as described above.

Procedure for Attachment of Sidechains to Lysine Residue.

The albumin binding residue (B-U-sidechain of formula I) can be attached to the peptide either by acylation to resin bound peptide or acylation in solution to the unprotected peptide using standard acylating reagent such as but not limited to DIC, HOBt/DIC, HOAt/DIC, or HBTU.

Attachment to Resin Bound Peptide:

Route I

Activated (active ester or symmetric anhydride) albumin binding residue (A-B)-sidechain of formula I) such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, dichloromethane, 2-propanol, methanol and diethyl ether.

Route II

The albumin binding residue (A-(B)-sidechain of formula I) was dissolved in N-methyl pyrrolidone/methylene chloride (1:1, 10 ml). The activating reagent such as hydroxybenzotriazole (HOBt) (4 molar equivalents relative to resin) and diisopropylcarbodiimide (4 molar equivalents relative to resin) was added and the solution was stirred for 15 min. The solution was added to the resin and diisopropyethylamine (4 molar equivalents relative to resin) was added. The resin was shaken 2 to 24 hours at room temperature. The resin was washed with N-methyl pyrrolidone (2×20 ml), N-methyl pyrrolidone/Methylene chloride (1:1) (2×20 ml) and methylene chloride (2×20 ml).

Route III

Activated (active ester or symmetric anhydride) albumin binding residue (A-B-sidechain of formula I) such as octadecanedioic acid mono-(2,5-dioxo-pyrrolidin-1-yl) ester (Ebashi et al. EP511600, 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the albumin binding residue such as tert.-butyl, the reaction mixture was lyophilized O/N and the isolated crude peptide deprotected afterwards—in case of a tert-butyl group the peptide was dissolved in a mixture of trifluoroacetic acid, water and triisopropylsilane (90:5:5). After for 30 min the mixture was, evaporated in vacuo and the finale petide purified by preparative HPLC.

Procedure for Removal of Fmoc-Protection:

The resin (0.25 mmol) was placed in a filter flask in a manual shaking apparatus and treated with N-methyl pyrrolidone/methylene chloride (1:1) (2×20 ml) and with N-methyl pyrrolidone (1×20 ml), a solution of 20% piperidine in N-methyl pyrrolidone (3×20 ml, 10 min each). The resin was washed with N-methyl pyrrolidone (2×20 ml), N-methyl pyrrolidone/Methylene chloride (1:1) (2×20 ml) and methylene chloride (2×20 ml).

Procedure for Cleaving the Peptide Off the Resin:

The peptide was cleaved from the resin by stirring for 180 min at room temperature with a mixture of trifluoroacetic acid, water and triisopropylsilane (95:2.5:2.5 to 92:4:4). The cleavage mixture was filtered and the filtrate was concentrated to an oil by a stream of nitrogen. The crude peptide was precipitated from this oil with 45 ml diethyl ether and washed 1 to 3 times with 45 ml diethyl ether.

Purification:

The crude peptide was purified by semipreparative HPLC on a 20 mm×250 mm column packed with either 5µ or 7µ C-18 silica. Depending on the peptide one or two purification systems were used.

TFA: After drying the crude peptide was dissolved in 5 ml 50% acetic acid $H_2O$ and diluted to 20 ml with $H_2O$ and injected on the column which then was eluted with a gradient of 40-60% $CH_3CN$ in 0.1% TFA 10 ml/min during 50 min at 40° C. The peptide containing fractions were collected. The purified peptide was lyophilized after dilution of the eluate with water.

Ammonium sulphate: The column was equilibrated with 40% $CH_3CN$ in 0.05M $(NH_4)_2SO_4$, which was adjusted to pH 2.5 with concentrated $H_2SO_4$. After drying the crude peptide was dissolved in 5 ml 50% acetic acid $H_2O$ and diluted to 20 ml with $H_2O$ and injected on the column which then was eluted with a gradient of 40%-60% $CH_3CN$ in 0.05M $(NH_4)_2SO_4$, pH 2.5 at 10 ml/min during 50 min at 40° C. The peptide containing fractions were collected and diluted with 3 volumes of $H_2O$ and passed through a Sep-Pak® C18 cartridge (Waters part. #:51910) which has been equilibrated with 0.1% TFA. It was then eluted with 70% $CH_3CN$ containing 0.1% TFA and the purified peptide was isolated by lyophilisation after dilution of the eluate with water.

The final product obtained was characterised by analytical RP-HPLC (retention time) and by LCMS The RP-HPLC analysis may be performed using UV detection at 214 nm and e.g. a Vydac 218TP54 4.6 mm×250 mm 5µ C-18 silica column (The Separations Group, Hesperia, USA) and eluted at e.g. 1 ml/min at 42° C. Most often one of following specific conditions were used:

Method 03_A1_1

HPLC (Method 03_A1_1): The RP-analysis was performed using a Waters 2690 systems fitted with a Waters 996 diode array detector. UV detections were collected at 214, 254, 276, and 301 nm on a 218TP54 4.6 mm×250 mm 5µ C-18 silica column (The Seperations Group, Hesperia), which was eluted at 1 ml/min at 42° C. The column was equilibrated with 10% of a 0.5 M ammonium sulfate, which was adjusted to pH 2.5 with 4M sulfuric acid. After injection, the sample was eluted by a gradient of 0% to 60% acetonitrile in the same aqueous buffer during 50 min.

Method 03_B1_2

HPLC (Method 03_B1_2): The RP-analysis was performed using a Waters 2690 systems fitted with a Waters 996 diode array detector. UV detections were collected at 214, 254, 276, and 301 nm on a Zorbax 300SB C-18 (4.5×150 mm, 50, which was eluted at 0.5 ml/min at 42° C. The column was equilibrated with an aqueous solution of TFA in water (0.1%). After injection, the sample was eluted by a gradient of 0% to 60% acetonitrile (+0.1% TFA) in an aqueous solution of TFA in water (0.1%) during 50 min.

Method 02_B1_1

HPLC (Method 02_B1_1): The RP-analyses was performed using a Alliance Waters 2695 system fitted with a Waters 2487 dualband detector. UV detections at 214 nm and 254 nm were collected using a Vydac 218TP53, C18, 300 Å, 5 um, 3.2 mm×250 mm column, 42° C. Eluted with a linear gradient of 0-60% acetonitrile, 95-35% water and 5% trifluoroacetic acid (1.0%) in water over 50 minutes at a flow-rate of 0.50 ml/min.

Method 01_B4_2

HPLC (Method 01_B4_2): RP-analyses was performed using a Waters 600S system fitted with a Waters 996 diode array detector. UV detections at 214 nm and 254 nm were collected using a Symmetry300 C18, 5 um, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 min/min.

Method 02_B4_4

HPLC (Method 02_B4_4): The RP-analyses was performed using a Alliance Waters 2695 system fitted with a Waters 2487 dualband detector. UV detections at 214 nm and 254 nm were collected using a Symmetry300 C18, 5 um, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 min/min.

Method 02_B6_1

HPLC (Method 02_B6_1): The RP-analyses was performed using a Alliance Waters 2695 system fitted with a Waters 2487 dualband detector. UV detections at 214 nm and 254 nm were collected using a Vydac 218TP53, C18, 300 Å, 5 um, 3.2 mm×250 mm column, 42° C. Eluted with a linear gradient of 0-90% acetonitrile, 95-5% water, and 5% trifluoroacetic acid (1.0%) in water over 50 minutes at a flow-rate of 0.50 ml/min.

Method 03_B6_1

HPLC (Method 03_B1_1): The RP-analysis was performed using a Waters 2690 systems fitted with a Waters 996 diode array detector. UV detections were collected at 214, 254, 276, and 301 nm on a 218TP54 4.6 mm×250 mm 5µ C-18 silica column (The Seperations Group, Hesperia), which was eluted at 1 ml/min at 42° C. The column was equilibrated with 5% acetonitrile (+0.1% TFA) in an aqueous solution of TFA in water (0.1%). After injection, the sample was eluted by a gradient of 0% to 90% acetonitrile (+0.1% TFA) in an aqueous solution of TFA in water (0.1%) during 50 min.

Alternatively a preparative gradient elution can be performed as indicated above and the percentage of acetonitrile where the compound elutes is noted. Identity is confirmed by MALDI.

The following instrumentation was used:

LCMS was performed on a setup consisting of Sciex API 100 Single quadropole mass spectrometer, Perkin Elmer Series 200 Quard pump, Perkin Elmer Series 200 autosampler, Applied Biosystems 785A UV detector, Sedex 75 evaporative light scattering detector The instrument control and data acquisition were done by the Sciex Sample control software running on a Windows 2000 computer.

The HPLC pump is connected to two eluent reservoirs containing:
A: 0.05% Trifluoro acetic acid in water
B: 0.05% Trifluoro acetic acid in acetonitrile The analysis is performed at room temperature by injecting an appropriate volume of the sample (preferably 20 µl) onto the column which is eluted with a gradient of acetonitrile.

The HPLC conditions, detector settings and mass spectrometer settings used are giving in the following table.
Column: Waters Xterra MS C-18×3 mm id 5 µm
Gradient: 5%-90% acetonitrile linear during 7.5 min at 1.5 ml/min Detection: 210 nm (analogue output from DAD)
ELS (analogue output from ELS), 40° C.
MS ionisation mode API-ES Alternatively LCMS was performed on a setup consisting of Hewlett Packard series 1100 G1312A Bin Pump, Hewlett Packard series 1100 Column compartment, Hewlett Packard series 1100 G1315A DAD diode array detector, Hewlett Packard series 1100 MSD and Sedere 75 Evaporative Light Scattering detectorcontrolled by HP Chemstation software. The HPLC pump is connected to two eluent reservoirs containing:
A: 10 mM NH$_4$OH in water
B: 10 mM NH$_4$OH in 90% acetonitrile The analysis was performed at 23° C. by injecting an appropriate volume of the sample (preferably 20 µl) onto the column which is eluted with a gradient of A and B.

The HPLC conditions, detector settings and mass spectrometer settings used are giving in the following table.
Column Waters Xterra MS C-18×3 mm id 5 µm
Gradient 5%-100% acetonitrile linear during 6.5 min at 1.5 ml/min
Detection 210 nm (analogue output from DAD)
ELS (analogue output from ELS)
MS ionisation mode API-ES. Scan 100-1000 amu step 0.1 amu

MALDI-MS:

Molecular weights of the peptides were determined using matrix-assisted laser desorption time of flight mass spectroscopy (MALDI-MS), recorded on a Microflex (Bruker). A matrix of α-cyano-4-hydroxy cinnamic acid was used.

Analytical HPLC Conditions (Method I):

Equilibration of the column (Xterra™ MS C18, 5 um, 4.6×150 mm Columm, P7N 186 000490) with 0.1% TFA/H$_2$O and elution by a gradient of 0% CH$_3$CN/0.1% TFA/H$_2$O to 60% CH$_3$CN/0.1% TFA/H$_2$O during 25 min followed by a gradient from 60% to 100% over 5 min.

In the examples of this invention the nomenclature and structurally graphics is meant as:

One letter symbols for the natural amino acids ares used, e.g. H is L-histidine, A is L-alanine ect. Three letter abbreviations for amino acids may also be used, e.g. His is L-histidine, Ala is L-alanine etc. For non natural amino acids three letter abbreviations are used, such as Aib for aminoisobutyric acid. The position of the amino acids may either be indicated with a number in superscript after the amino acid symbols such as Lys[37], or as Lys37. The N-terminal amino group may be symbolized either as NH$_2$ or as H. The C-terminal carboxylic group may be symbolized either as —OH or as —COOH. The C-terminal amide group is symbolized as —NH$_2$ The sub-structures

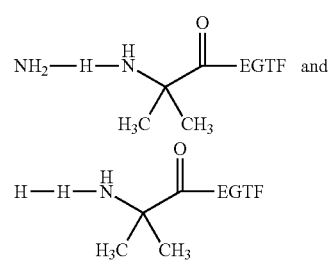

both mean His-Aib-Glu-Gly-Thr-Phe.

The epsilon amino group of Lysine may be described either as the greek symbol ε or spelled "epsilon".

The structures in the examples below are in several cases a combination of one letter symbols for the naturally amino acids combined with the three letter abbreviation Aib for aminoisobutyric acid. In several cases some of the amino acids are shown in expanded full structure. Thus lysine that has been derivatised may be shown as the expanded full structures in example 1 where the lysine in position 37 is expanded. The nitrogen (with indicated H) between arginine in position 36 and the expanded lysine in position 37 is thus the nitrogen of the peptide bond connecting the two amino acids in example 1.

According to the procedure above, the following derivatives were prepared as non-limiting examples of the invention:

Example 1

N-epsilon37{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis7,Glu22,Arg26,Arg34,Lys37]GLP-1(7-37) amide

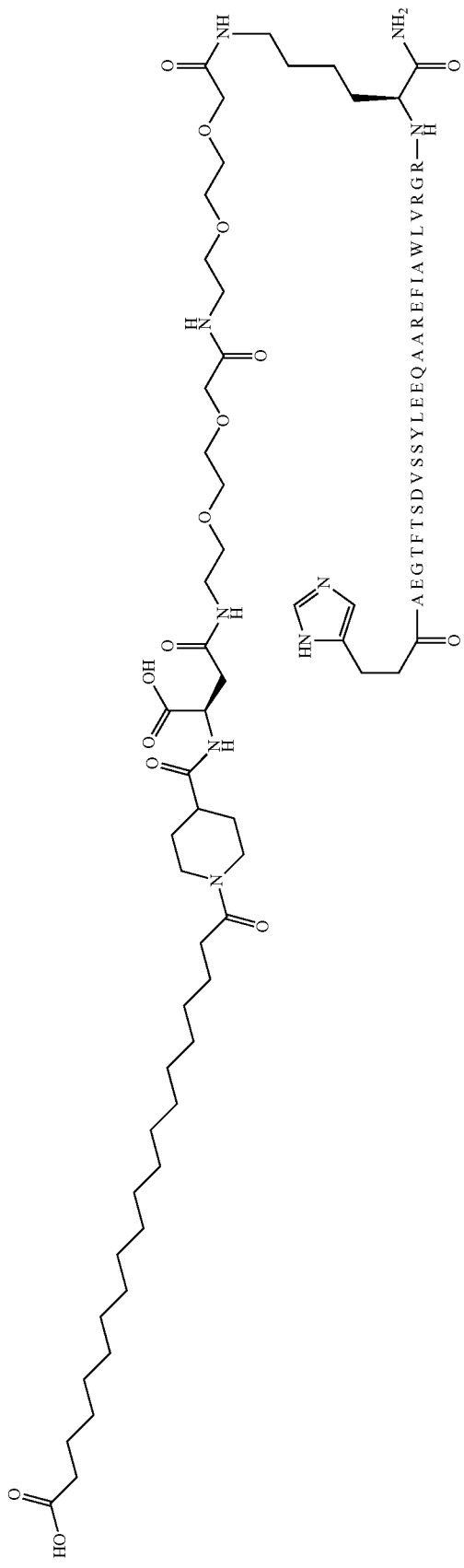

Preparation method: A
HPLC method 66:
RT=35.49 min
LCMS: m/z=1096.2 $(M+3H)^{3+}$
Calculated MW=4380.0

Example 2

N-epsilon37{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Arg34,Lys37]GLP-1-(7-37)amide

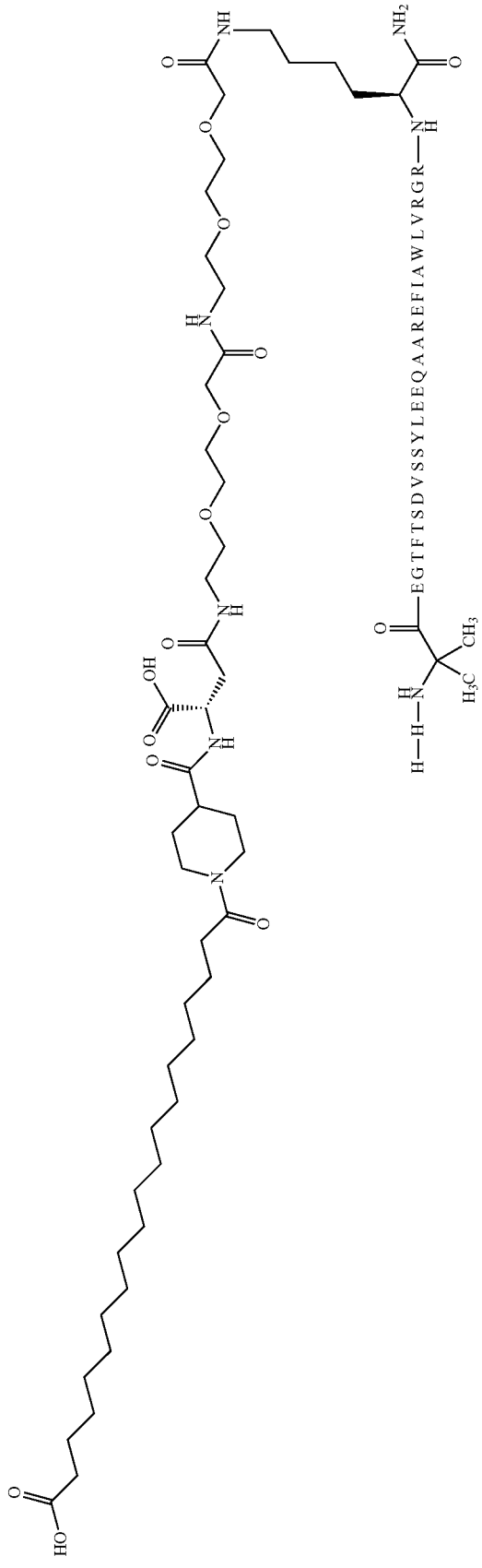

Preparation method: B
The peptide was eluted at 66% acetontrile.
Structure confirmed by MALDI-MS
Calculated MW=4409.1

Example 3

N-epsilon37-[2-(2-[2-(2-[2-(2-((R)-3-[1-(17-Carboxyheptadecanoyl)piperidin-4-ylcarbonylamino]3-carboxypropionylamino)ethoxy)ethoxy]acetylamino)ethoxy]ethoxy)acetyl][DesaminoHis 7,Glu22,Arg26,Arg34,Phe(m-CF3)28]GLP-1-(7-37)amide

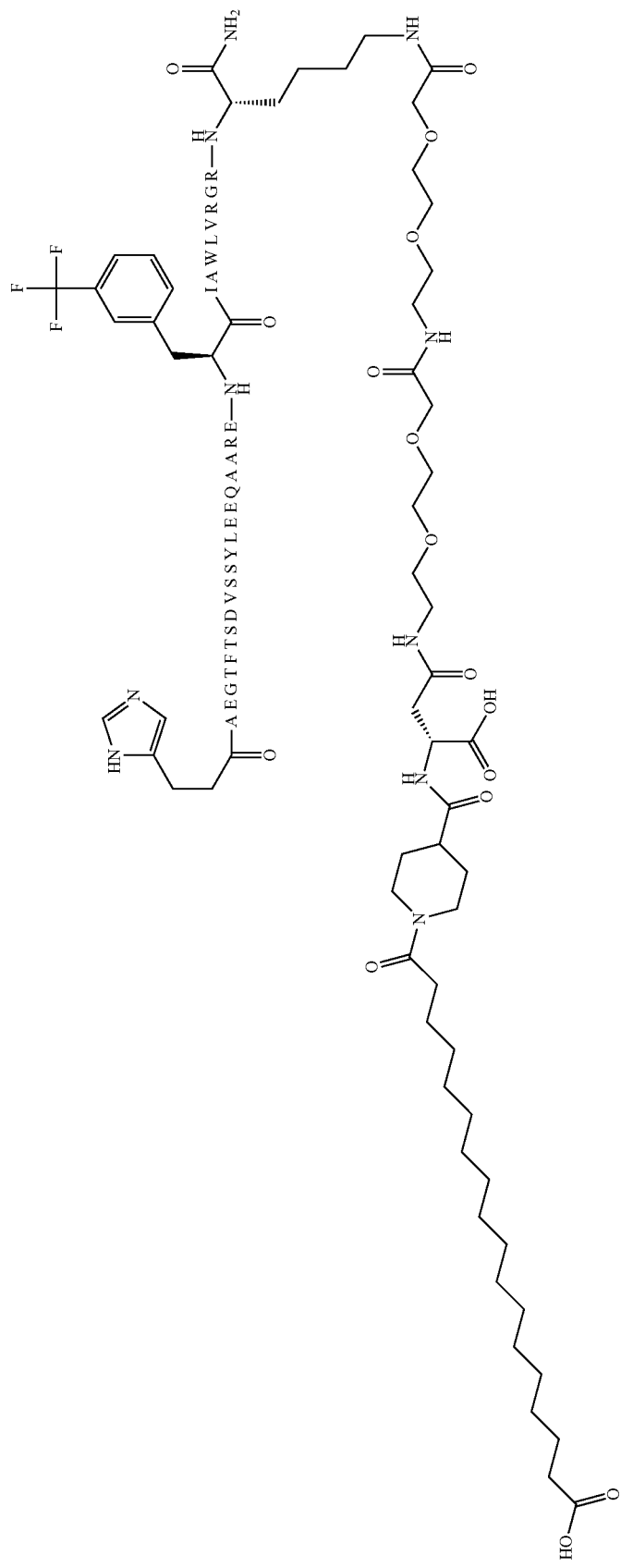

Preparation method: A
HPLC (method B):
RT=11.92 min
LCMS: m/z=1474.8 $(M+3H)^{3+}$
Calculated MW=4420.0

Example 4

N-epsilon30{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Lys30] GLP-1-(7-37)

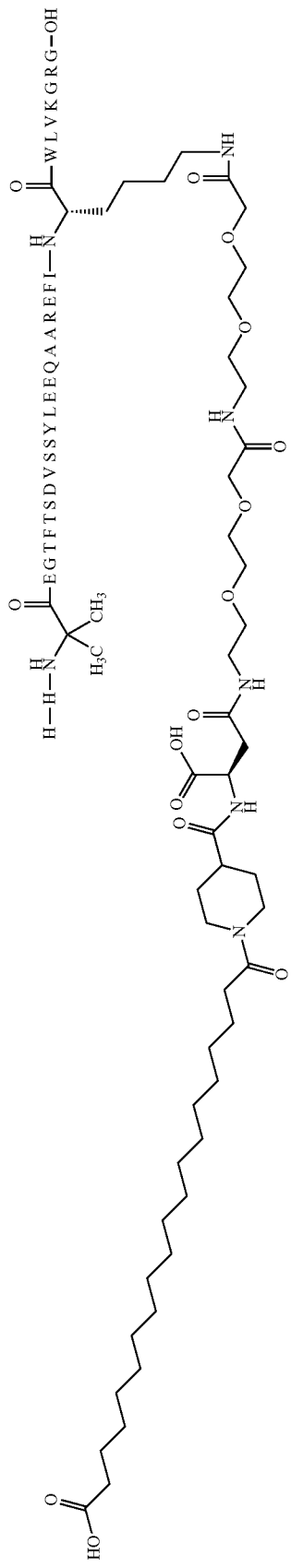

Preparation method: Method A except that the peptide was prepared on an Apex396 from Advanced Chemtech using a molar excess of 8-10 fold amino acid, DIC and HOAt/HOBt (1:1) and the Mtt group was deprotected with hexaflouroisopropanol. The final product was characterized by analytical HPLC and MALDI-MS.
HPLC method I:
RT=27.6 min
MALDI-MS: 4367.9

Example 5

N-epsilon31{2-[2-(2-{2-[2-((S)-3-carboxy-3-{[1-(19-carboxynonadecanoyl)piperidine-4-carbonyl]amino}propionylamino)ethoxy]ethoxy}acetylamino)ethoxy]ethoxy}acetyl [Aib8,Glu22,Arg26,Lys31] GLP-1-(7-37)

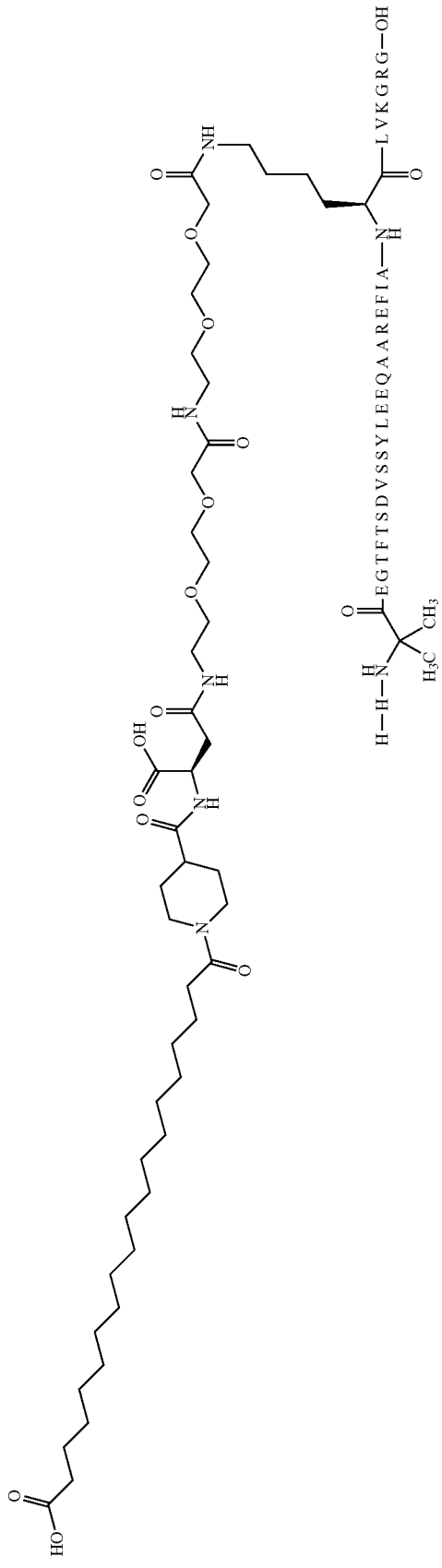

Preparation method: Method A except that the peptide was prepared on an Apex396 from Advanced Chemtech using a molar excess of 8-10 fold amino acid, DIC and HOAt/HOBt (1:1) and the Mtt group was deprotected with hexaflouroisopropanol. The final product was characterized by analytical HPLC and MALDI-MS.
HPLC method I:
RT=28.4 min
MALDI-MS: 4252.5

Example 6

N-epsilon31-(2-{2-[2-(2-{2-[2-((S)-3-Carboxy-3-{[1-(19-carboxy-nonadecanoyl)piperidine-4-carbonyl]amino}propionylamino)ethoxy]ethoxy}acetylamino)ethoxy]ethoxy}acetyl)[Aib8,Glu22,Arg26,Lys31,Arg34]GLP-1-(7-37)

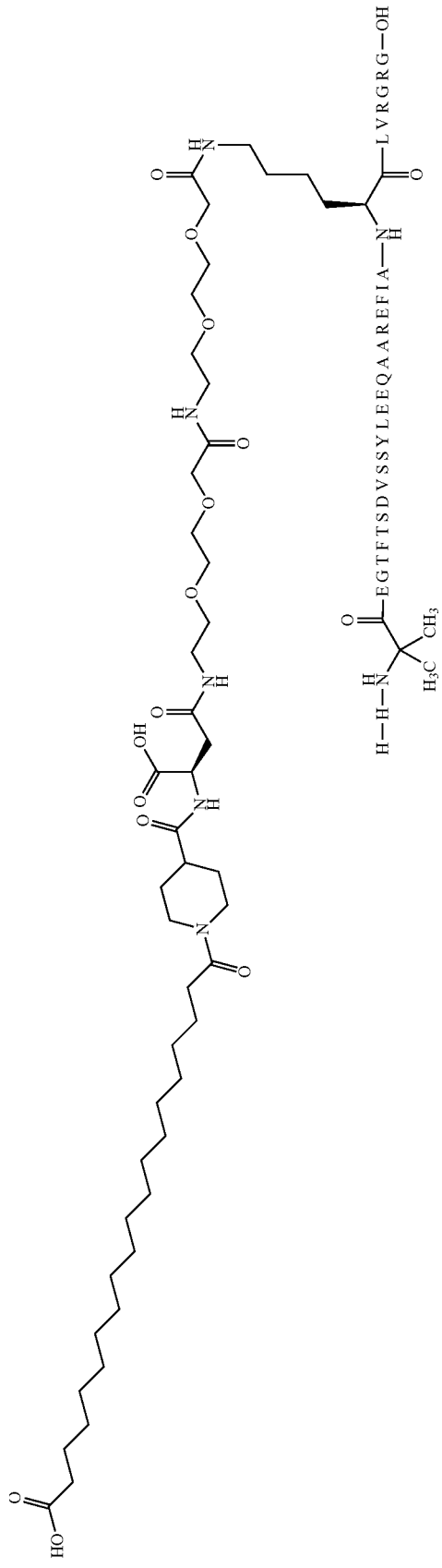

Preparation method: B
The peptide was eluted at 66% acetonitrile.
Structure confirmed by MALDI-MS
Calculated MW=4280.9

Example 7

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37) amide

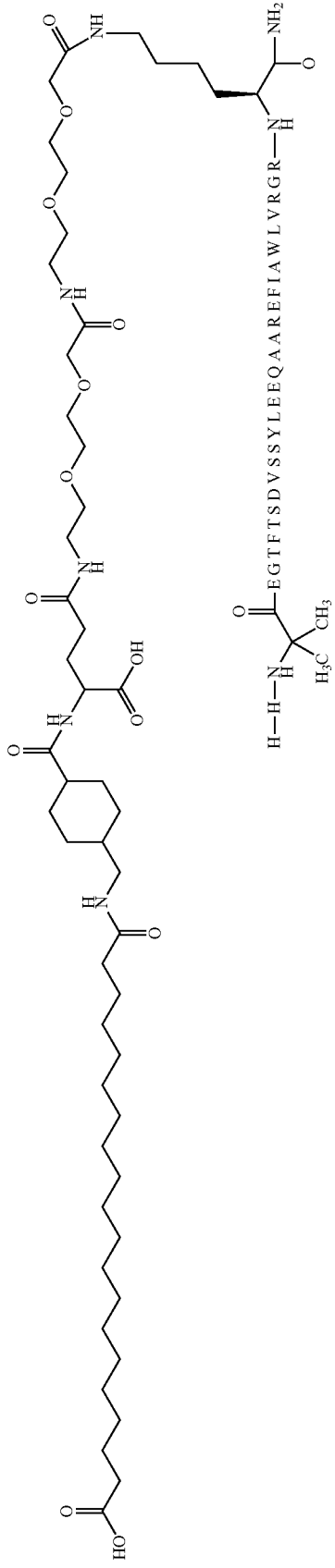

Preparation method: B
The peptide was eluted at 67% acetonitrile.
Structure confirmed by MALDI-MS
Calculated MW=4451.1

Example 8

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37)amide

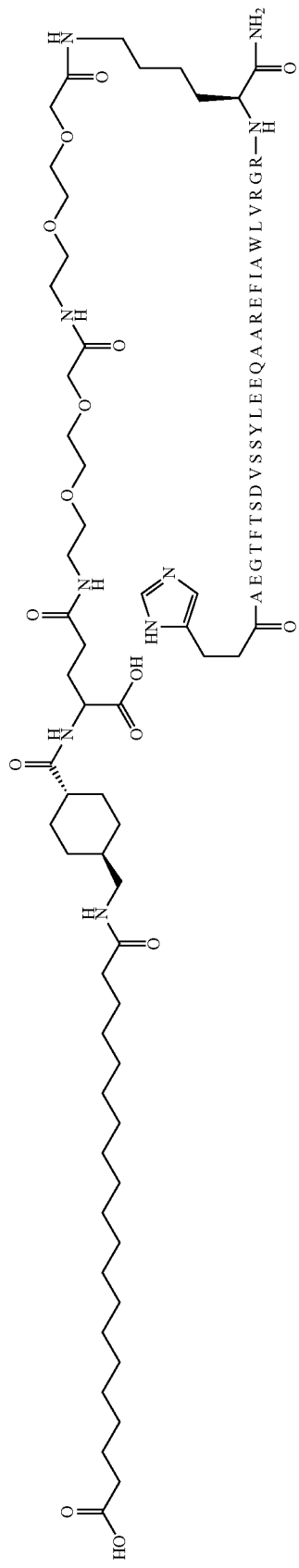

Preparation method: B
The peptide was eluted at 68% acetonitrile.
Structure confirmed by MALDI-MS
Calculated MW=4422.1

Example 9

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37)

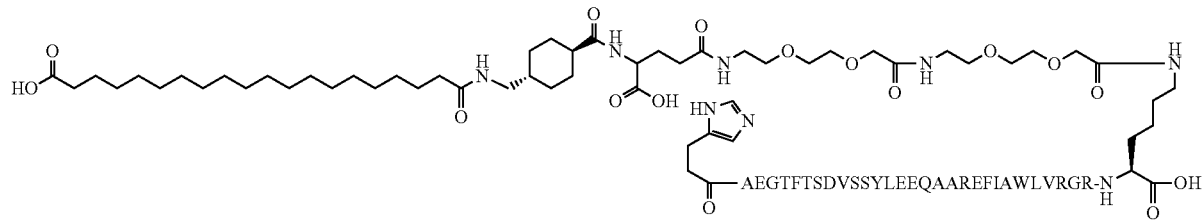

Preparation method: B
The peptide was eluted at 69% acetonitrile.
Structure confirmed by MALDI-MS
Calculated MW=4423.1

Example 10

N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Glu30,Arg34,Lys37]GLP-1-(7-37)

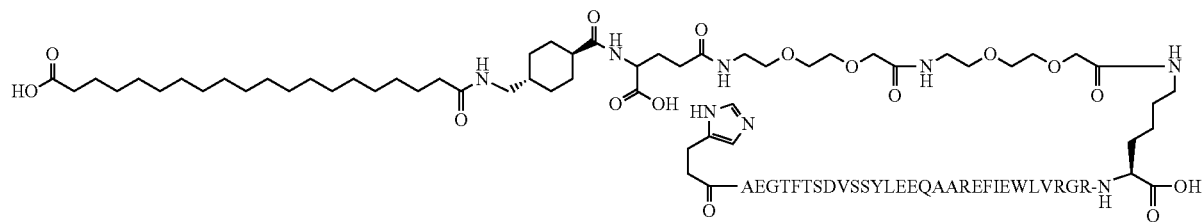

Preparation method: B
The peptide was eluted at 68% acetonitrile.
Structure confirmed by MALDI-MS
Calculated MW=4481.1

Example 11

N-epsilon20-[2-(2-{2-[(S)-4-Carboxy-4-((S)-4-carboxy-4-{12-[4-(16-(1H-tetrazol-5-yl)hexadecanoyl-sulfamoyl)butyrylamino]
dodecanoylamino}butyrylamino)butyrylamino]
ethoxy}ethoxy)acetyl][Aib8,Lys20,Glu22,Arg26,Glu30,Pro37]GLP-1-(7-37)amide

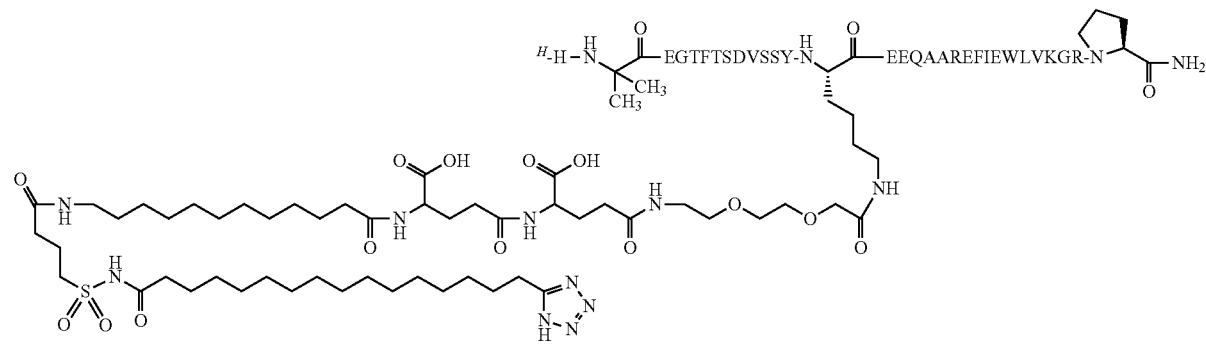

Preparation method: B
The peptide was eluted at 62% acetonitrile.
Structure confirmed by MALDI-MS
Calculated MW=4638.3

Example 12

N-epsilon37-[2-(2-{2-[(S)-4-Carboxy-4-((S)-4-carboxy-4-{12-[4-(16-(1H-tetrazol-5-yl)hexadecanoyl-sulfamoyl)butyrylamino]
dodecanoylamino}butyrylamino)butyrylamino]
ethoxy}ethoxy)acetyl][Aib8,Glu22,Arg26,Arg34,Lys37]GLP-1-(7-37)amide

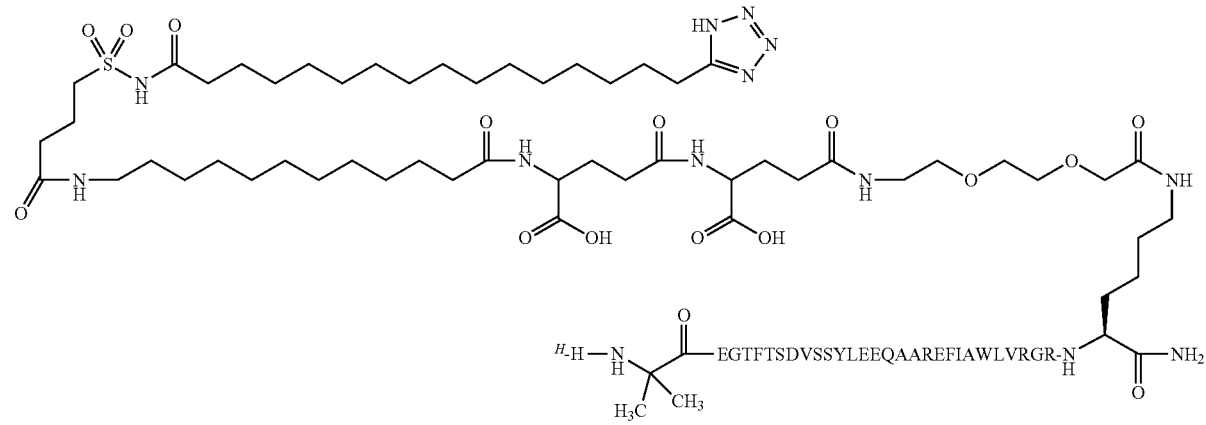

Preparation method: B
The peptide was eluted at 69% acetonitrile.
Structure confirmed by MALDI-MS
Calculated MW=4624.3

Example 13

N-epsilon37-[2-(2-{2-[(S)-4-Carboxy-4-((S)-4-carboxy-4-{12-[4-(16-(1H-tetrazol-5-yl)hexadecanoyl-sulfamoyl)butyrylamino]
dodecanoylamino}butyrylamino)butyrylamino]
ethoxy}ethoxy)acetyl][DesaminoHis7,Glu22,Arg26,
Arg34,Lys37]GLP-1-(7-37)amide

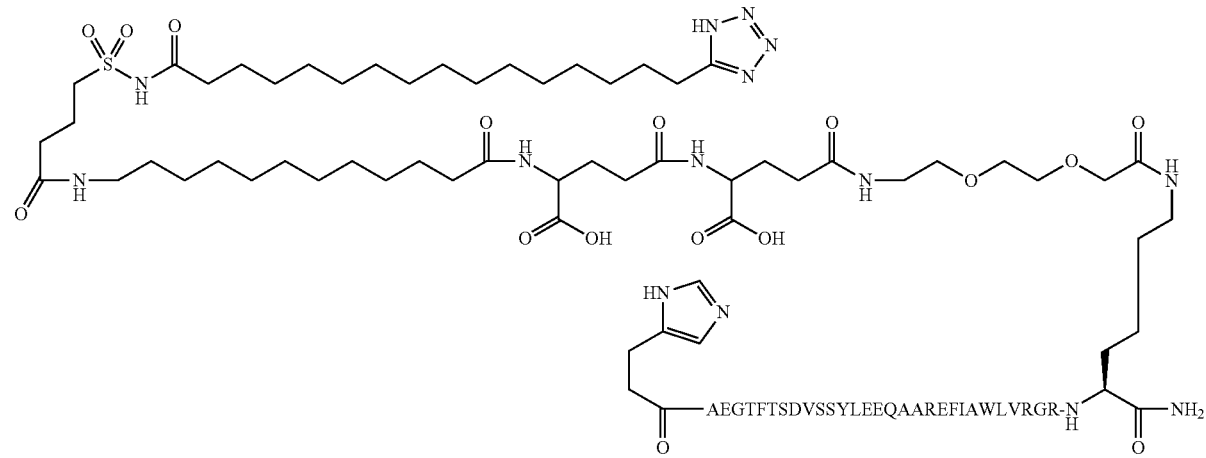

Preparation method: B
The peptide was eluted at 65% acetonitrile.
Structure confirmed by MALDI-MS
Calculated MW=4595.3

Example 14

[Aib8,Glu22,Arg26,Glu30,Pro37]GLP-1-(7-37)Lys
[2-(2-{2-[4-Carboxy-4-(4-carboxy-4-{4-[4-(16-1H-tetrazol-5-yl-hexadecanoylsulfamoyl)butyrylamino]
butyrylamino}butyrylamino)butyrylamino]
ethoxy}ethoxy)acetyl]

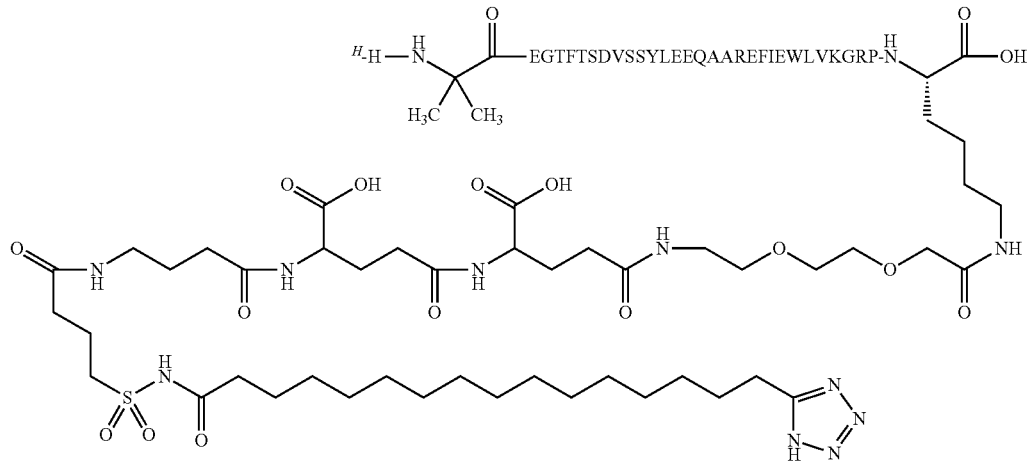

Preparation method: The peptide was prepared on an Apex396 from Advanced Chemtech and attachment of thioamide linker was achieved in two steps. 4-sulfamoylbutyric acid was first coupled the resin using DIC and HOAt/HOBt (1:1). Then, 16-(1H-tetrazol-5-yl)hexadecanoic acid mixed with carbonyldiimidazol in NMP was added to the resin followed by addition of DBU. Otherwise is the same protocol described in the beginning of the example section.

Calculated MW=4640.2

Example 15
N-epsilon37 (Polyethyleneglycol2000)[Desamino-His7,Glu22,Arg26,Arg34,Lys37]GLP-1 (7-37) amide
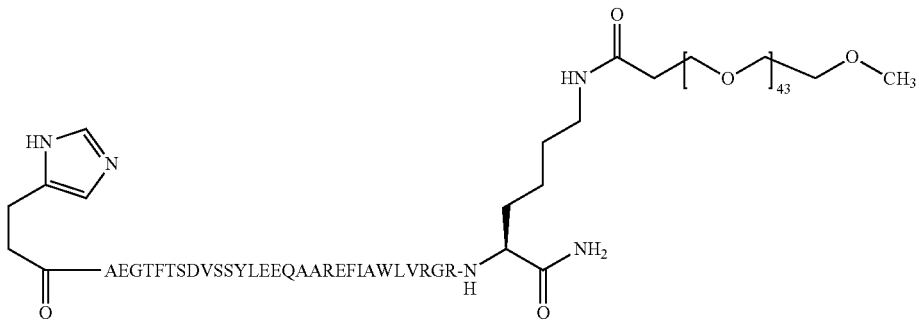
Preparation method: Route III
HPLC (method A1)
RT=40.88 min
LCMS: m/z=Heterogenous but corresponding to stating material+an average of 2000
Calculated $(M+H)^+$=5519
Example 16
N-epsilon37 (3-((2-(2-(2-(2-(2-Hexadecyloxyethoxy) ethoxy) ethoxy)ethoxy)ethoxy))propionyl)[DesaminoHis7,Glu22,Arg26,Arg34,Lys37]GLP-1(7-37)-amide
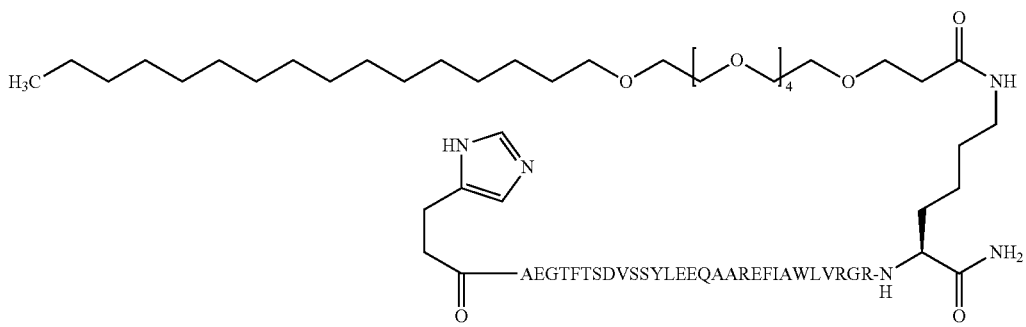

Example 17

N-epsilon37-{2-(2-(2-(2-[2-(2-(4-(hexadecanoy-lamino)-4-carboxybutyrylamino)ethoxy)ethoxy]acetyl)ethoxy)ethoxy)acetyl)}-[desaminoHis7, Glu22,Arg26, Glu30,Arg34,Lys37] (GLP-1-(7-37) amide Preparation method: route III
HPLC (method B6):
RT=42.3 min
LCMS: m/z=1353.3 (M+3H)³⁺
Calculated (M+H)⁺=4055.7

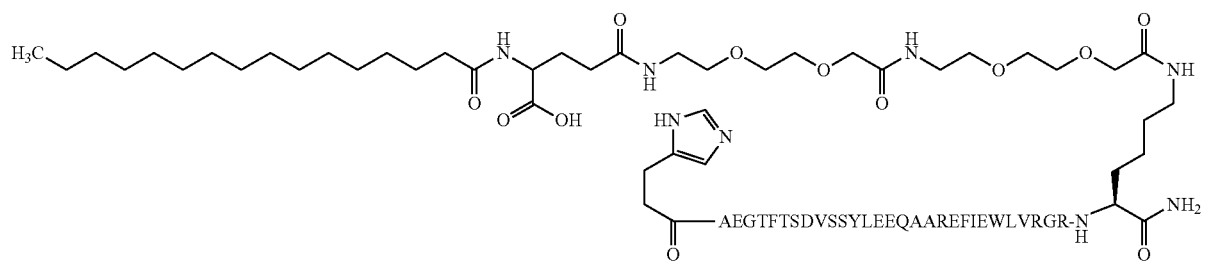

Preparation method: A
HPLC (method B6):
RT=36.1 min
LCMS: m/z=1419.0 (M+3H)³⁺
Calculated (M+H)⁺=4254.8

Example 18

N-epsilon37-{2-(2-(2-(2-[2-(2-(4-(hexadecanoy-lamino)-4-carboxybutyrylamino)ethoxy)ethoxy]acetyl)ethoxy)ethoxy)acetyl)}-[desaminoHis7, Glu22, Arg26,Arg34,Lys 37] (GLP-1-(7-37)amide

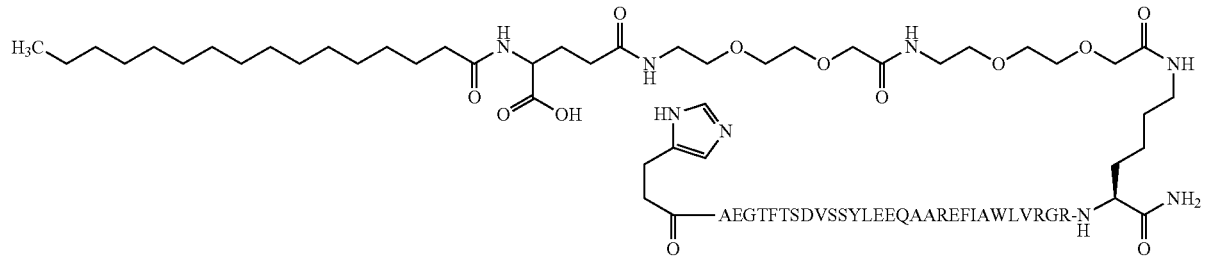

Preparation method: A
HPLC (method B6):
RT=36.06 min
LCMS: m/z=1399 (M+3H)³⁺
Calculated (M+H)⁺=4196.8

Example 19

N-epsilon37-(2-(2-(2-(2-(2-(2-(2-(2-(Octade-canoylamino)ethoxy)ethoxy)acetylamino)ethoxy)ethoxy)acetylamino)ethoxy)ethoxy)acetyl][desami-noHis7,Glu22,Arg26,Arg34,Lys37] GLP-1 (7-37) amide

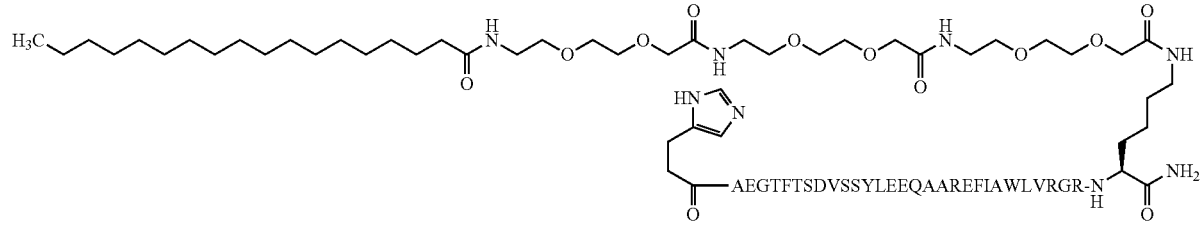

Preparation method: A
HPLC (method B6):
RT=40.1 min
LCMS: m/z=1414.6 (M+3H)$^{3+}$
Calculated (M+H)$^+$=4240.9

Example 20

N-epsilon36-(2-(2-(2-((2-[2-(2-(17-carboxyheptade-canoylamino)ethoxy)ethoxy]acetylamino)ethoxy)ethoxy)acetyl) [Aib8,Glu22,Arg26,Glu30,Lys36] GLP-1-(7-37)Glu-amide

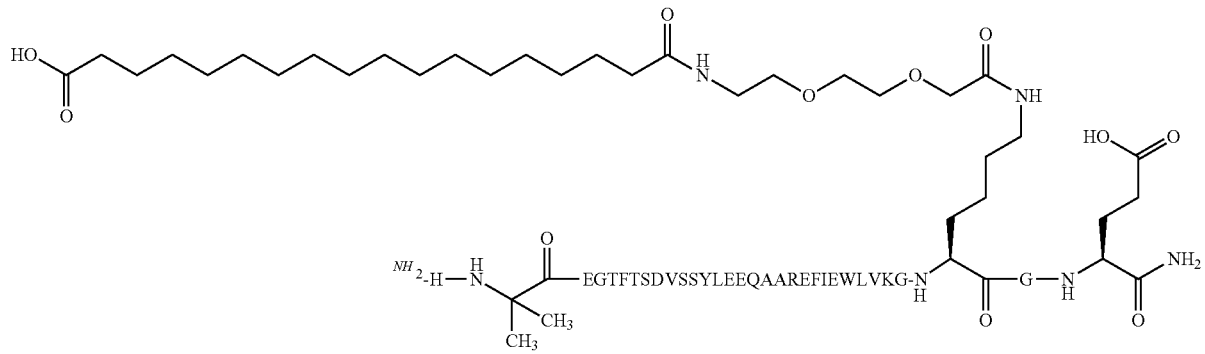

Preparation method: B
The peptide was eluted at 68% acetonitrile.
Structure confirmed by MALDI-MS
Calculated MW=4069.6

Example 21

N-epsilon37-[4-(16-(1H-Tetrazol-5-yl)hexade-canoylsulfamoyl)butyryl][DesaminoHis7,Glu22,Arg26,Arg34,Lys37]GLP-1-(7-37)amide

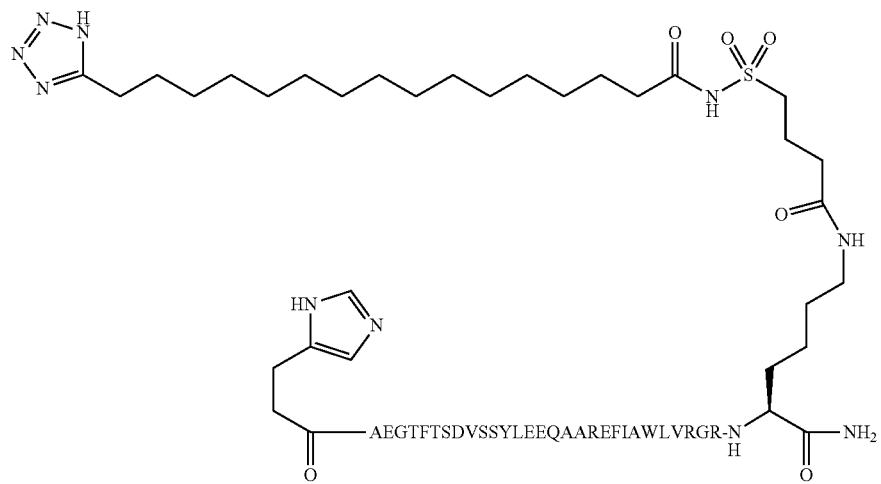

Preparation method: B
The peptide was eluted at 64% acetonitrile.
Structure confirmed by MALDI-MS
Calculated MW=3994.6

Example 22

N-epsilon37-[2-(2-{2-[2-(2-{2-[(S)-4-Carboxy-4-(19-carboxynonadecanoylamino)butyrylamino]ethoxy}ethoxy)acetylamino]ethoxy}ethoxy)acetyl][DesaminoHis7,Glu22,Arg26,Arg34,Lys37]GLP-1-(7-37)

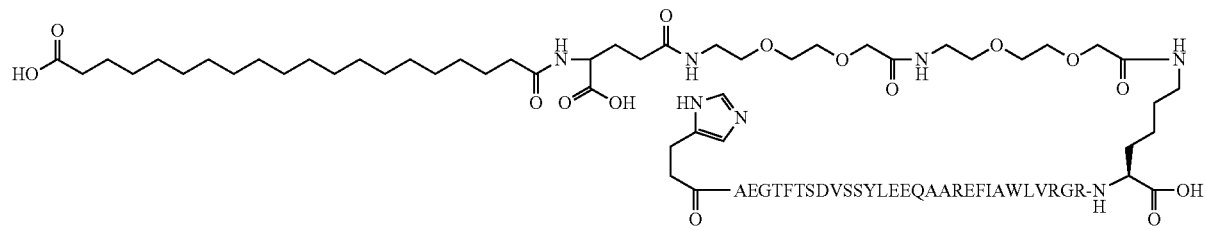

Preparation method: B
The peptide was eluted at 67% acetonitrile.
Structure confirmed by MALDI-MS
Calculated MW=4283.9

Example 23

N-epsilon31-[2-(2-{2-[2-(2-{2-[4-Carboxy-4-(17-carboxy-heptadecanoylamino)butyrylamino]ethoxy}ethoxy) acetylamino]ethoxy}ethoxy)acetyl][Aib8,Glu22,Arg26,Lys31]GLP-1-(7-37)

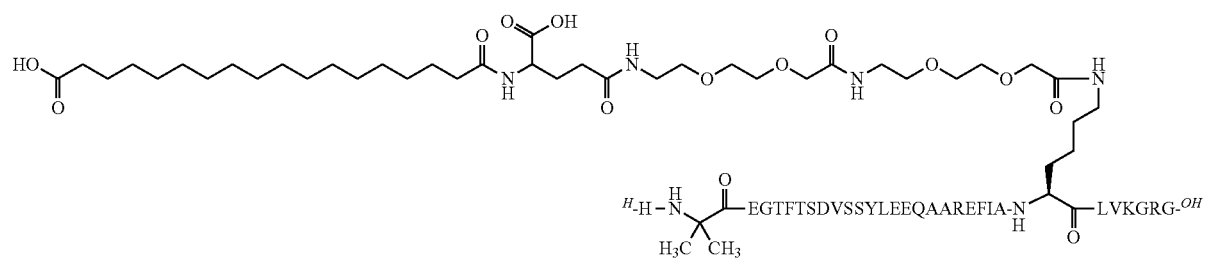

Preparation method: Method A except that the peptide was prepared on an Apex396 from Advanced Chemtech using a molar excess of 8-10 fold amino acid, DIC and HOAt/HOBt (1:1) and the Mtt group was deprotected with hexaflouroisopropanol. The final product was characterized by analytical HPLC and MALDI-MS.
HPLC method I:
RT=27.2 min
MALDI-MS: 4127.9

Example 24

N-epsilon20-(2-{2-[2-(2-{2-[((S)-4-Carboxy-4-hexadecanoylamino-butyrylamino)ethoxy]ethoxy}acetylamino)ethoxy]ethoxy}-acetyl)[Aib8,Lys20,Glu22,Arg26,Glu30,Pro37]GLP-1-(7-37) amide

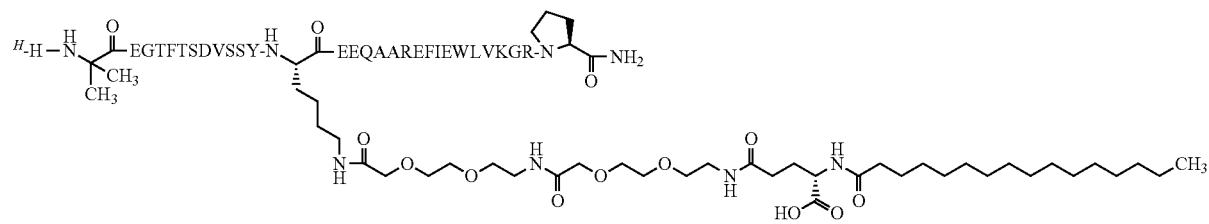

Preparation method: B
The peptide was eluted at 66% acetonitrile.
Structure confirmed by MALDI-MS
Calculated MW=4239.8

Example 25

N-epsilon37-(2-{2-[2-((S)-4-Carboxy-4-{(S)-4-carboxy-4-[(S)-4-carboxy-4-(19-carboxy-nonadecanoylamino)butyrylamino]butyrylamino}butyrylamino)ethoxy]ethoxy}acetyl)[DesaminoHis7,Glu22,Arg26,Arg34,Lys37]GLP-1-(7-37)

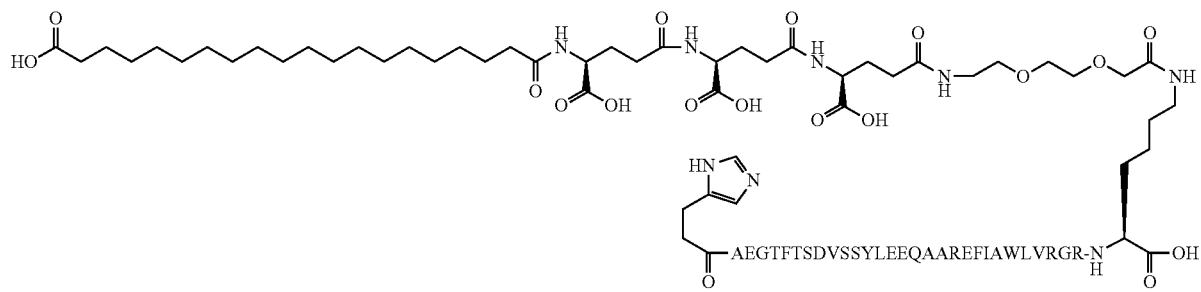

Preparation method: B
The peptide was eluted at 65% acetonitrile.
Structure confirmed by MALDI-MS
Calculated MW=4397.0

Example 26

N-epsilon37-{2-[2-(2-{(S)-4-[(S)-4-(12-{4-[16-(2-tert-Butyl-2H-tetrazol-5-yl)-hexadecanoylsulfamoyl]butyrylamino}dodecanoylamino)-4-carboxybutyrylamino]-4-carboxybutyrylamino}ethoxy)ethoxy]acetyl}[DesaminoHis7,Glu22,Arg26,Arg34,Lys37]GLP-1 (7-37)

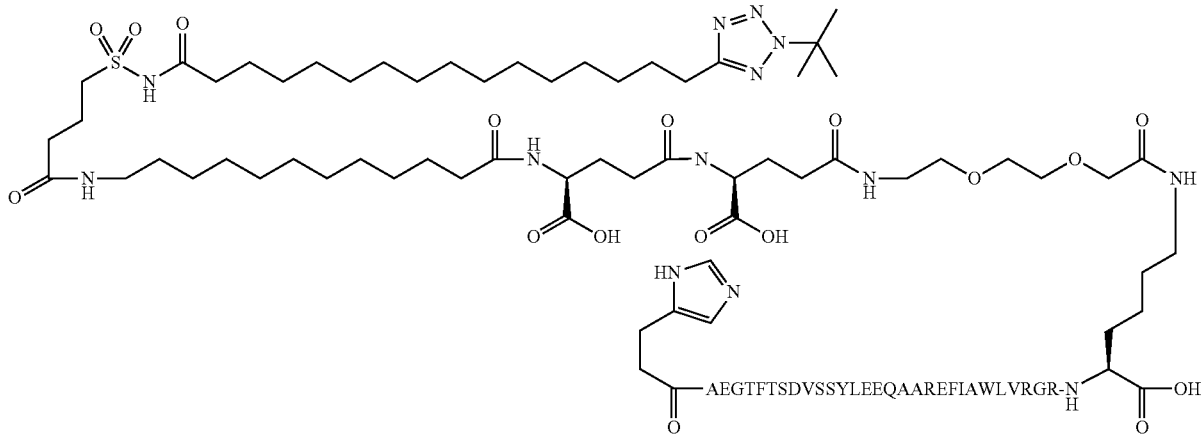

Preparation method B
The peptide was eluted at 74% acetonitrile
Structure confirmed by MALDI-MS
Calculated MW=4652.4

Example 27

N-epsilon37-[2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl] [Aib8,Glu22,Arg26,Arg34,Lys37]GLP-1-(7-37).

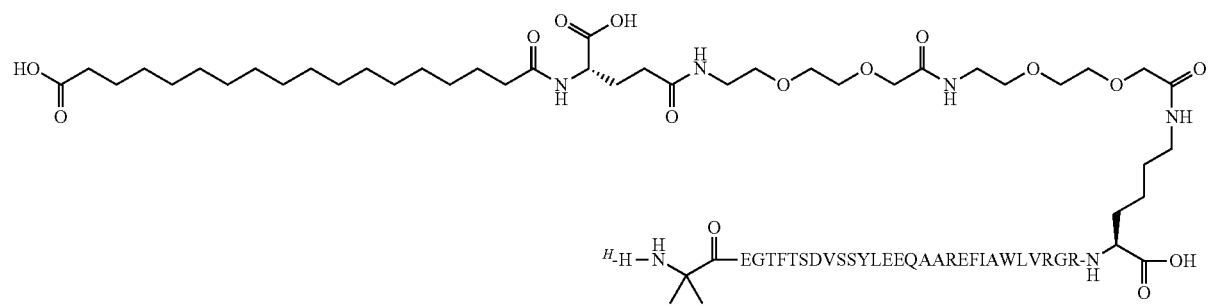

Preparation analogous to SPPS Method B.
HPLC method 02_B6_1:
RT=34.27 min
LCMS: m/z=1072 (M+4H)$^{4+}$
Calculated (M)=4284.9

Example 28

N-alpha37-[2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl] [Aib8,Glu22,Arg26,Arg34,epsilon-Lys37] GLP-1-(7-37)peptide

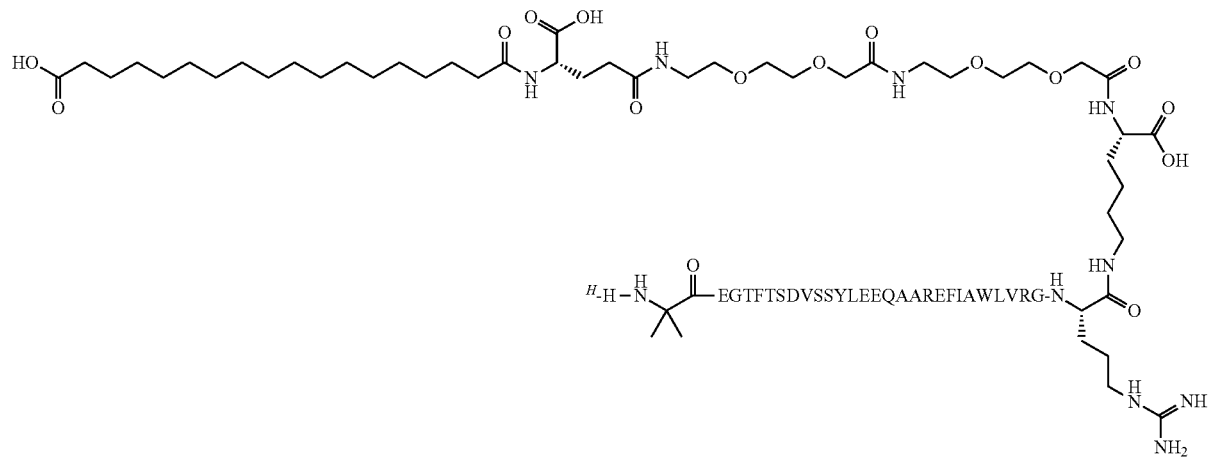

Preparation analogous to SPPS Method B.
HPLC method I_BDSB2:
RT=10.19 min
LCMS: m/z=1072 (M+4H)$^{4+}$
Calculated (M)=4284.9

Example 29

N-epsilon37-[2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl] [desaminoHis7,Glu22,Arg26,Arg34,Lys37] GLP-1-(7-37)

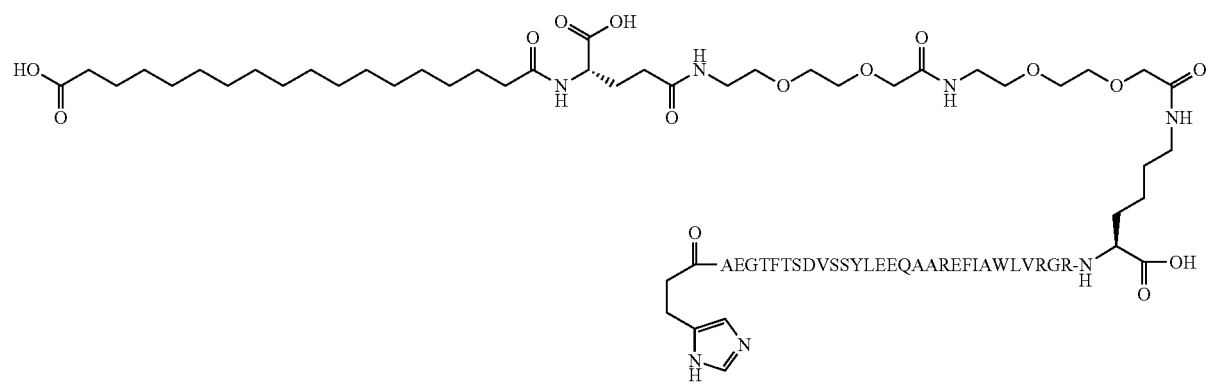

Preparation analogous to SPPS Method B.
HPLC method I_BDSB2:
RT=9.96 min
LCMS: m/z=1064 (M+4H)$^{4+}$
Calculated (M)=4255.8

Example 30

N-epsilon36-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [desaminoHis7, Glu22, Arg26, Glu30, Arg34, Lys36]GLP-1-(7-37)-Glu-Lys peptide

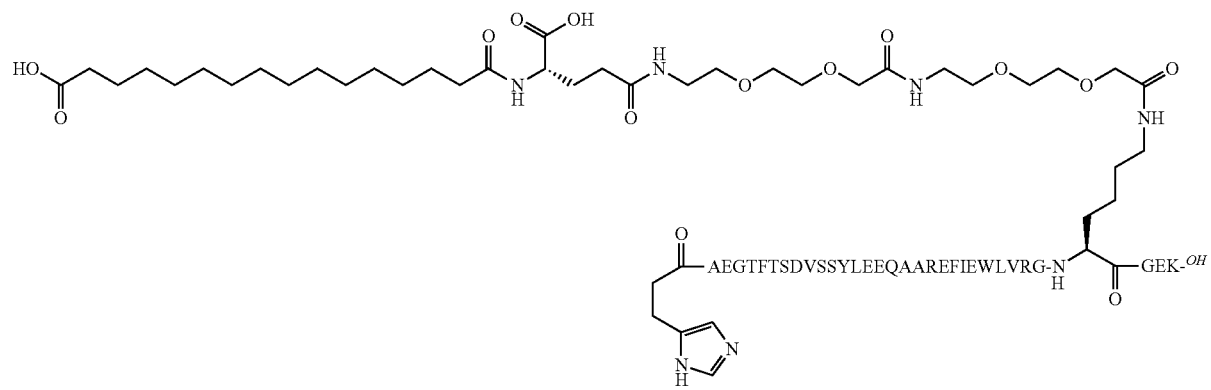

Preparation analogous to SPPS Method B.
HPLC method I_BDSB2:
RT=6.40 min
LCMS: m/z=1111 (M+4H)$^{4+}$
Calculated (M)=4444.0

Example 31

[desaminoHis7, Glu22, Arg26, Glu30, Arg34]GLP-1-(7-37)-Glu-Lys(2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl) peptide

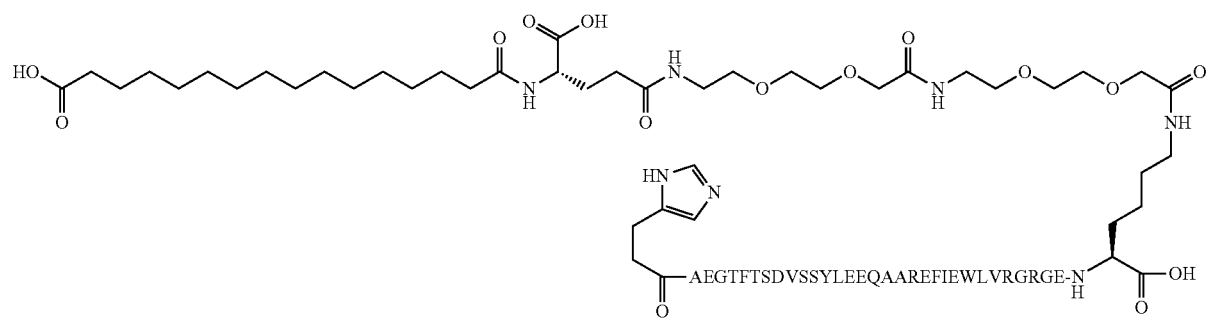

Preparation analogous to SPPS Method B.
HPLC method I_BDSB2:
RT=6.52 min
LCMS: m/z=1119 (M+4H)$^{4+}$
Calculated (M)=4472

Example 32

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37)

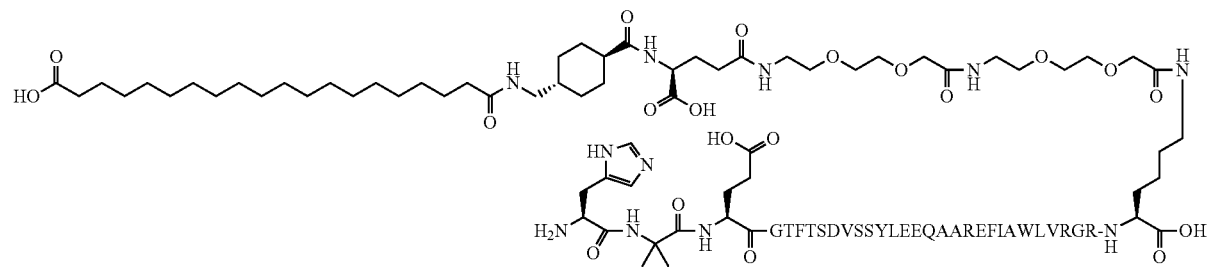

Preparation analogous to SPPS Method B.
HPLC method 02_B6_1:
RT=33.58 min
LCMS: m/z=1114 (M+4H)$^{4+}$
Calculated (M)=4451.1

Example 33

N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl]-[Aib8,Glu22, Arg26,Arg34, Aib35, Lys37] GLP-1-(7-37)

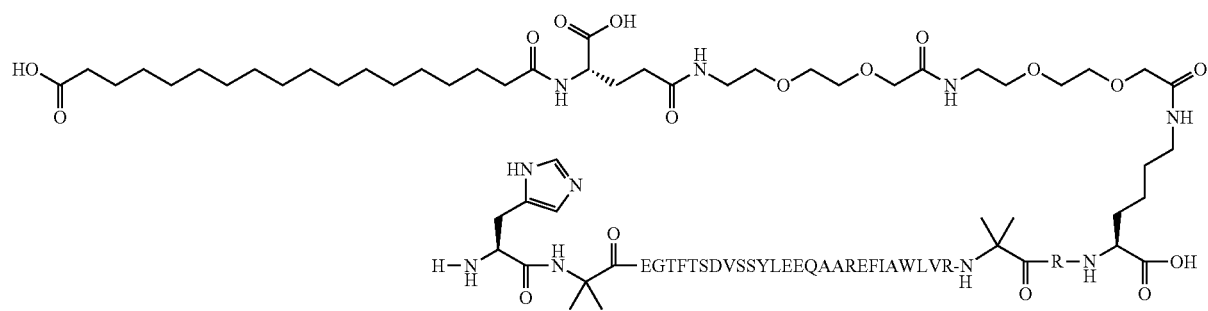

Preparation analogous to SPPS Method B.
UPLC method 04_A3_1:
RT=9.81 min
LCMS: m/z=1079 (M+4H)$^{4+}$
Calculated (M)=4312.9

Example 34

N-epsilon31-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib8,Glu22,Val25,Arg26,Lys31,Arg34,Arg35,Arg37]GLP-1-(7-37)

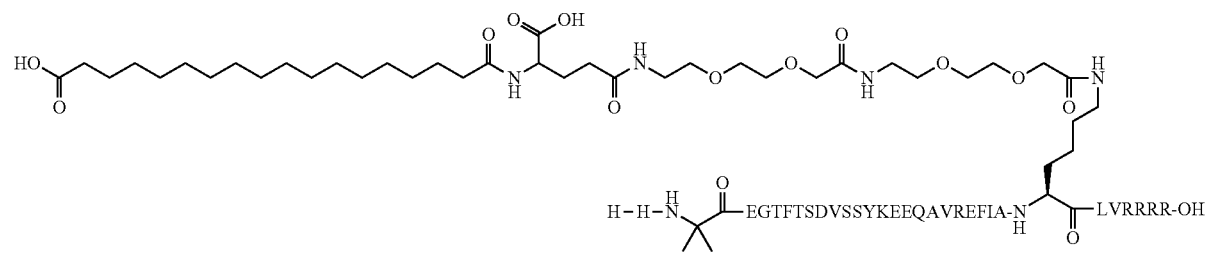

Preparation method: The peptide was prepared by SPPS Method C and the final product was characterized by analytical HPLC and MALDI-MS.
HPLC (02-B4-4): RT=7.9 min
HPLC (neutral, 30-60% over 16 min): RT=5.6 min
MALDI-MS: 4395
Calculated MW=4397

Example 35

N-epsilon31{2-(2-{2-[2-(2-{2-[4-Carboxy-4-(17-carboxy-heptadecanoylamino)butyrylamino]ethoxy}ethoxy)acetylamino]ethoxy}ethoxy)acetyl}-[Aib8,Glu22,Val25,Arg26,Lys31,Arg34,Arg35,Arg37)]GLP-1(7-37)yl [Arg39,Arg40,Arg41]

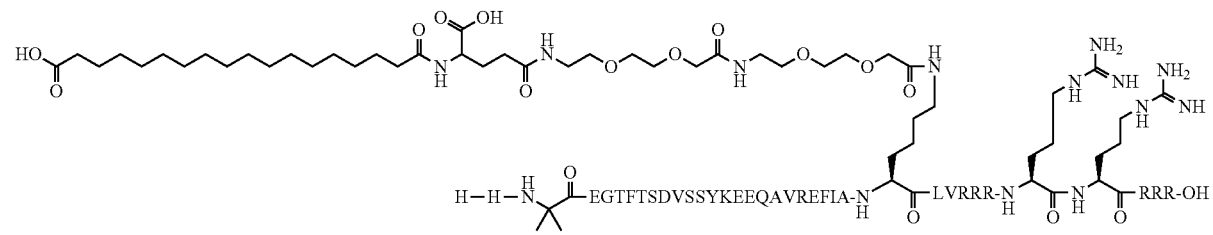

Preparation method: The peptide was prepared by SPPS Method C and the final product was characterized by analytical HPLC and LC-MS.
HPLC (02-B4-4): RT=7.36 min
HPLC (neutral): RT=17.5 min
MALDI-MS: 5022
Calculated MW=5021.8

Example 36

N-epsilon31-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Glu22,Val25,Arg26,Lys31,Lys35,Lys36]GLP-1-(7-36) amide

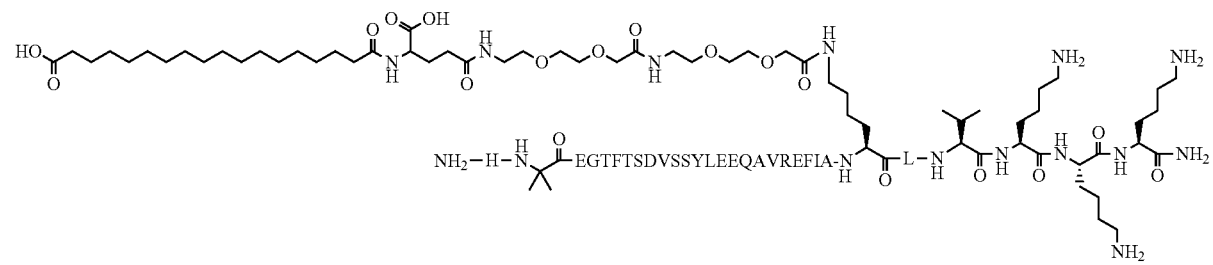

Preparation method: The peptide was prepared by SPPS Method C and the final product was characterized by analytical HPLC and MALDI-MS.
HPLC (02-B4-2): RT=8.4 min
HPLC (04-A3-1): RT=7.8 min
MALDI-MS: 4141
Calculated MW=4140.8

Example 37

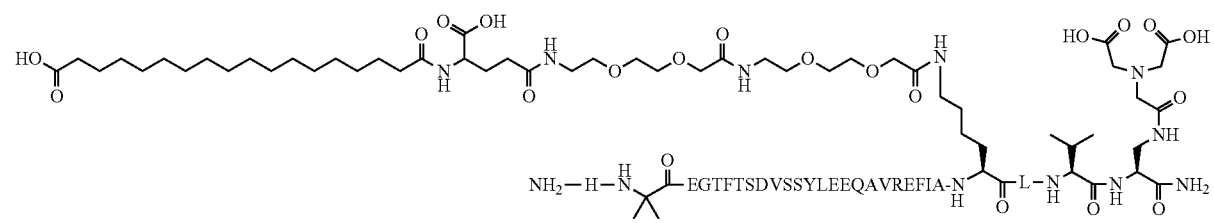

N-epsilon31-{2-(2-{2-[2-(2-{2-[4-Carboxy-4-(17-carboxy-heptadecanoylamino)butyrylamino]ethoxy}ethoxy)acetylamino]ethoxy}ethoxy)acetyl}-N-beta34-(2-(bis-carboxymethylamino)acetyl)[Aib8,Glu22,Val25,Arg26,Lys31,Dap34] GLP-1(7-34) amide
Preparation method: The peptide was prepared by SPPS Method C and the final product was characterized by analytical HPLC and MALDI-MS.
HPLC (02-86-1): RT=36.7 min
HPLC (A4-A3-1): RT=8.9 min
MALDI-MS: 4015.9
Calculated MW=4015.5

Example 38

N-epsilon-37-[(S)-4-carboxy-4-(2-{2-[2-(2-{2-[2-(17-carboxyheptadecanoylamino) ethoxy] ethoxy}acetylamino) ethoxy]ethoxy}acetylamino) butyryl] [Aib8,Glu22,Arg26,34,Lys37] GLP-1 (7-37)

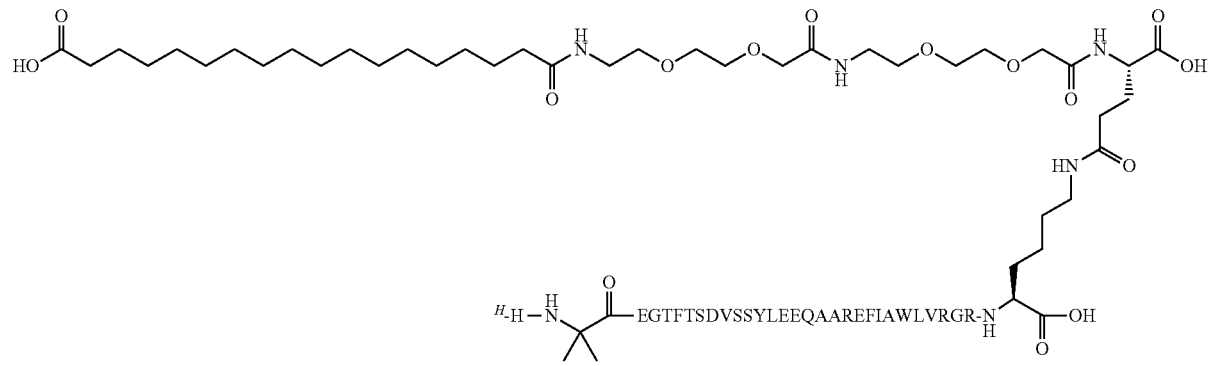

Preparation analogous to SPPS Method B.
UPLC method 04_A3_1:
RT=10.26 min
LCMS: m/z=1071.7 (M+4H)$^{4+}$
Calculated (M)=4284.9

BIOLOGICAL FINDINGS

Protraction of GLP-1 Derivatives after i.v. or s.c. Administration

The protraction of a number GLP-1 derivatives of the invention may be determined by monitoring the concentration thereof in plasma after sc administration to healthy pigs, using the methods described below. For comparison also the concentration in plasma of GLP-1(7-37) after sc. administration may be followed. The protraction of other GLP-1 derivatives of the invention can be determined in the same way.

Example 39

Pharmacokinetic Testing in Minipigs

A number of GLP-1 derivatives of the invention (the compounds of Examples 1, 4, 5, 7, 8, 9, 13, and 22) were subjected to pharmacokinetic testing in minipigs. Liraglutide was included in the test for comparative purposes. A second comparative compound was also included, viz. a GLP-1 derivative with the substitutions (22E+26R), which is described in Example 63 of WO 2005/027978.

Generally, the test substances are to be dissolved in a vehicle suitable for subcutaneous or intravenous administration. The concentration is to be adjusted so the dosing volume is approximately 1 ml. In the present study the test substances were administered subcutaneously.

The study was performed in 12 male Göttingen minipigs from Ellegaard Göttingen Minipigs ApS. An acclimatisation period of approximately 10 days was allowed before the animals entered the study. At start of the acclimatisation period the minipigs were about 5 months old and in the weight range of 8-10 kg.

The study was conducted in a suitable animal room with a room temperature set at 21-23° C. and the relative humidity to 50%. The room was illuminated to give a cycle of 12 hours light and 12 hours darkness. Light was from 06.00 to 18.00 h. The animals were housed in pens with straw as bedding, six together in each pen. The animals had free access to domestic quality drinking water during the study, but were fasted from approximately 4 pm the day before dosing until approximately 12 hours after dosing. The animals were weighed on arrival and on the days of dosing.

The animals received a single subcutaneous injection. The subcutaneous injection was given on the right side of the neck, approximately 5-7 cm from the ear and 7-9 cm from the middle of the neck. The injections were given with a stopper on the needle, allowing 0.5 cm of the needle to be introduced. Each test substance was given to three animals. Each animal received a dose of 2 nmol/kg body weight. Six animals were dosed per week while the remaining six were rested.

A full plasma concentration-time profile was obtained from each animal. Blood samples were collected according to the following schedule:
After Intravenous Administration (not Applicable in the Present Study):
Predose (0), 0.17 (10 minutes), 0.5, 1, 2, 4, 6, 8, 12, 24, 48, 72, 96, and 120 hours after injection.
After Subcutaneous Administration:
Predose (0), 0.5, 1, 2, 4, 6, 8, 12, 24, 48, 72, 96, and 120 hours after injection. At each sampling time, 2 ml of blood was drawn from each animal. The blood samples were taken from a jugular vein.

The blood samples were collected into test tubes containing a buffer for stabilisation in order to prevent enzymatic degradation of the GLP-1 derivatives.

Plasma was immediately transferred to Micronic-tubes. Approximately 200 μl plasma was transferred to each Micronic-tube. The plasma was stored at −20° C. until assayed. The plasma samples were assayed for the content of GLP-1 derivatives using an immunoassay.

The plasma concentration-time profiles were analysed by a non-compartmental pharmacokinetic analysis. The following pharmacokinetic parameters were calculated at each occasion: AUC, AUC/Dose, AUC$_{\%\ Extrap}$, $C_{max}$, $t_{max}$, $\lambda_z$, $t_{1/2}$, CL, CL/f, $V_z$, $V_z$/f and MRT.

All tested GLP-1 derivatives of the invention had a half-life after subcutaneous administration in minipigs in the range of 40-100 hours. The half-lives of the comparative compounds liraglutide and Compound 135 were 18 hours, and 28 hours, respectively.

Selected derivatives of the invention are tested in Danish Landrace pigs.

Pharmacokinetic Testing of GLP-1 Derivatives in Pigs

Pigs (50% Duroc, 25% Yorkshire, 25% Danish Landrace, app 40 kg) are fasted from the beginning of the experiment. To each pig 0.5 nmol of test derivative per kg body weight is administered in a 50 µM isotonic solution (5 mM phosphate, pH 7.4, 0.02% Tween®-20 (Merck), 45 mg/ml mannitol (pyrogen free, Novo Nordisk). Blood samples are drawn from a catheter in vena jugularis. 5 ml of the blood samples are poured into chilled glasses containing 175 µl of the following solution: 0.18 M EDTA, 15000 KIE/ml aprotinin (Novo Nordisk) and 0.30 mM Valine-Pyrrolidide (Novo Nordisk), pH 7.4. Within 30 min, the samples are centrifuged for 10 min at 5-6000*g. Temperature is kept at 4° C. The supernatant is pipetted into different glasses and kept at minus 20° C. until use.

The plasma concentrations of the peptides are determined in a sandwich ELISA or by RIA using different mono- or polyclonal antibodies. Choice of antibodies depends of the GLP-1 derivatives. The time at which the peak concentration in plasma is achieved varies within wide limits, depending on the particular GLP-1 derivative selected.

General Assay Protocol for Sandwich ELISA in 96-Wells Microtiterplate

Coating buffer (PBS): Phosphate buffered saline, pH7.2
Wash-buffer (PBS-wash): Phosphate buffered saline, 0.05% v/v Tween 20, pH 7.2
Assay-buffer (BSA-buffer): Phosphate buffered saline, 10 g/l Bovin Serum Albumin
(Fluka 05477), 0.05% v/v Tween 20, pH 7.2
Streptavidin-buffer Phosphate buffered saline, 0.5 M NaCl, 0.05% v/v Tween 20, pH 7.2
Standard: Individual derivatives in a plasma-matrix
A-TNP: Nonsens antibody
AMDEX: Streptavin-horseradish-peroxodase (Amersham RPN4401V)
TMB-substrate: 3,3',5,5'tetramethylbenzidine (<0.02%), hydrogen peroxide The assay was carried out as follows (volumen/well):
1.) coat with 100 µl catching antibody 5 µg/ml in PBS-buffer
   incubate o/n, 4° C.
   5×PBS-wash
   blocked with last wash in minimum 30 minute
   then empty the plate
2.) 20 µl sample+100 µl biotinylated detecting antibody 1 µg/ml in BSA-buffer with 10 µg/ml A-TNP
   incubate 2 h, room temperature, on a shaker→5×PBS-wash, then empty the plate
3.) 100 µl AMDEX 1:8000 in Streptavidin-buffer
   incubate 45-60 minute, room temperature, on a shaker
   5×PBS-wash, then empty the plate
4.) 100 µl TMB-substrate
   incubate x minute at room temperature on a shaker
   stop the reaction with 100 µl 4 M H$_3$PO$_4$
   Read the absorbance at 450 nm with 620 nm as reference
   The concentration in the samples was calculated from standard curves.

General Assay Protocol for RIA

DB-buffer: 80 mM phosphate buffer, 0.1% Human serum albumin, 10 mM EDTA, 0.6 mM thiomersal, pH 7.5
FAM-buffer: 40 mM phosphate buffer, 0.1% Human Serum Albumin, 0.6 mM thiomersal, pH 7.5
Charcoal: 40 mM phosphate buffer, 0.6 mM thiomersal, 16.7% bovine plasma, 15 g/l activated carbon, pH 7.5 (mix the suspension minimum 1 h before use at 4° C.)
Standard: Individual derivatives in a plasma-matrix The assay was carried out in minisorp tubes 12×75 mm (volumen/tube) as follows:

|  | Db-buffer | SAMPLE | Antibody | FAM-buf. | Tracer | Charcoal | H$_2$O |
|---|---|---|---|---|---|---|---|
| Day 1 | | | | | | | |
| Total | | | | | 100 µL | | |
| NSB | 330 µL | | | 100 µL | | | |
| Sample | 300 µL | 30 µL | 100 µL | | 100 µL | | |
| Mix, incubate o/n at 4° C. | | | | | | | |
| Day 2 | | | | | | | |
| Total | | | | | | | 1.5 mL |
| NSB | | | | | | 1.5 mL | |
| Sample | | | | | | 1.5 mL | |

Mix—incubate 30 min at 4° C.—centrifuge at 3000 rpm, 30 min—immediately after transfer supernatants to new tubes, close with stopper and count on gamma-counter for 1 minute.

The concentration in the samples was calculated from individual standard curves.

GLP-1 Radio Receptor Assay (RRA):

The method is a radiometric-ligand binding assay using LEADseeker imaging particles. The assay is composed of membrane fragments containing the GLP-1 receptor, unlabeled GLP-1 analogues, human GLP-1 labelled with $^{125}$I and PS LEADseeker particles coated with wheat germ agglutinin (WGA). Cold and $^{125}$I-labelled GLP-1 will compete for the binding to the receptor. When the LEADseeker particles are added they will bind to carbohydrates residues on the membrane fragments via the WGA-residues. The proximity between the $^{125}$I-molecules and the LEADseeker particles causes light emission from the particles. The LEADseeker will image the emitted light and it will be reversibly correlated to the amount of GLP-1 analogue present in the sample.

Reagents & Materials:

Pre treatment of animal plasma: Animal plasma was heat treated for 4 hrs at 56° C. and centrifuged at 10.000 rpm for 10 minutes. Afterwards, Val-Pyr (10 µM) and aprotenin (500 KIE/mL) was added and stored at <−18° C. until use.

GLP-1 analogues calibrators: GLP-1 analogues were spiked into heat-treated plasma to produce dilution lines ranging from approximately 1 µM to 1 pM.

GLP-1 RRA assay buffer: 25 mM Na-HEPES (pH=7.5), 2.5 mM CaCl$_2$, 1 mM MgCl$_2$, 50 mM NaCl, 0.1% ovalbumin, 0.003% tween 20, 0.005% bacitracin, 0.05% NaN$_3$.

GLP-1 Receptor Suspension: GLP-1 receptor membrane fragments were purified from baby hamster kidney (BHK) cells stably expressing the human pancreatic GLP-1 receptor. Stored <−80° C. until use.
WGA-Coupled Polystyrene LEADseeker Imaging Beads (RPNQ0260, Amersham): The beads were reconstituted with GLP-1 RRA assay buffer to a concentration of 13.3 mg/mL. The GLP-1 receptor membrane suspension was then added and incubated cold (2-8° C.) at end-over-end for at least 1 hr prior to use.
[$^{125}$I]-GLP-1(7-36)amide (Novo Nordisk A/S). Stored <−18° C. until use.
Ethanol 99.9% vol (De Dansk Spritfabrikker A/S): Stored <−18° C. until use.
MultiScreen® Solvinert 0.45 μm hydrophobic PTFE plates (MSRPN0450, Millipore Corp.)
Poly propylene plates (cat. no. 650201, Greiner Bio-One)
White polystyrene 384-well plates (cat. no. 781075, Greiner Bio-One)
Apparatus:
Horizontal plate mixer
Centrifuge with a standard swinging-bucket microtitre plate rotor assembly
UltraVap—Drydown Sample Concentrator (Porvair)
LEADseeker™ Multimodality Imaging System (Amersham)
Assay PROCEDURE:
Sample Preparation:
Mount the MultiScreen® Solvinert filter plate on a chemical-comparable receiver plate (i.e. poly propylene plates) to collect the filtrate.
Add 150 μL ice-cold ethanol 99.9% into the empty wells of the MultiScreen® Solvinert filter plate followed by 50 μL calibrator or plasma sample. Place the storage lid on the filter plate.
Incubate 15 minutes at 18-22° C. on a horizontal plate mixer. Place the assembled filter and receiver plate, with the lid, into a standard swinging-bucket microtitre plate rotor assembly. The filtrate is then collected in the empty wells of the receiver plate at 1500 rpm for 2 minutes.
Dry down the filtrate by using the UltraVap with heated (40° C.) $N_2$ for duration of 15 miuntes. Reconstitute the dry material by adding 100 μL GLP-1 RRA assay buffer into each well. Incubate for 5 minutes on a horizontal mixer.
GLP-1 Radio Receptor Assay:
Use the following pipetting scheme and white polystyrene 384-well plates:
  35 μL GLP-1 RRA assay buffer
  5 μL reconstituted filtrate.
  10 μL [$^{125}$I]-GLP-1(7-36)amide. The stock solution was diluted in GLP-1 RRA assay buffer to 20.000 cpm/well prior to use.
  15 μL GLP-1 receptor membrane fragments (≈0.5 μg/well) pre-coated to WGA-polystyrene LEADseeker imaging beads (0.2 mg/well)
Seal the plates and incubate over night at 18-22° C.
The light emission from each wells are detected by using the LEADseeker™ Multimodality Imaging System for duration of 10 minutes.

Example 40

Stimulation of cAMP Formation in a Cell Line Expressing the Cloned Human GLP-1 Receptor The potencies of a number of GLP-1 derivatives of the invention were determined as described below, i.e. as the stimulation of the formation of cyclic AMP (cAMP) in a medium containing the human GLP-1 receptor. For comparison, the potencies of two known GLP-1 derivates were also determined, viz. that of liraglutide, and that of Compound 135, a GLP-1 derivative with the substitutions (22E+26R), which is described in Example 63 of WO 2005/027978.

Purified plasma membranes from a stable transfected cell line, BHK467-12A (tk-ts13), expressing the human GLP-1 receptor was stimulated with the GLP-1 derivative in question, and the potency of cAMP production was measured using the AlphaScreen™ cAMP Assay Kit from Perkin Elmer Life Sciences.

A stable transfected cell line has been prepared at NN A/S, Denmark, and a high expressing clone was selected for screening. The cells were grown at 5% $CO_2$ in DMEM, 5% FCS, 1% Pen/Strep (Penicillin/Streptomycin) and 0.5 mg/ml of the selection marker G418.

Cells at approximate 80% confluence were washed 2× with PBS (Phosphate Buffered Saline) and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenized by the Ultrathurax for 20-30 sec. in 10 ml of Buffer 1 (20 mM Na-HEPES, 10 mM EDTA, pH=7.4), centrifuged 15 min at 20.000 rpm and the pellet resuspended in 10 ml of Buffer 2 (20 mM Na-HEPES, 0.1 mM EDTA, pH=7.4). The suspension was homogenized for 20-30 sec and centrifuged 15 min at 20.000 rpm. Suspension in Buffer 2, homogenization and centrifugation was repeated once and the membranes were resuspended in Buffer 2 and ready for further analysis or stored at −80° C.

The functional receptor assay was carried out by measuring the peptide induced cAMP production by The AlphaScreen Technology. The basic principle of The AlphaScreen Technology is a competition between endogenous cAMP and exogenously added biotin-cAMP. The capture of cAMP is achieved by using a specific antibody conjugated to acceptor beads. Formed cAMP was counted and measured at a AlphaFusion Microplate Analyzer. The $EC_{50}$ values were calculated using the Graph-Pad Prisme software (version 5).

TABLE 1

Potency of GLP-1 derivatives

| Compound of Example No. | Potency [$EC_{50}$/nM] |
|---|---|
| 1 | 0.37 |
| 2 | 0.20 |
| 3 | 0.35 |
| 4 | 0.52 |
| 5 | 0.20 |
| 6 | 0.18 |
| 7 | 0.58 |
| 8 | 0.66 |
| 9 | 0.50 |
| 10 | 0.66 |
| 11 | 0.61 |
| 12 | 1.80 |
| 13 | 1.97 |
| 14 | 0.29 |
| 15 | 0.03 |
| 16 | 0.15 |
| 17 | 0.16 |
| 18 | 0.02 |
| 19 | 0.05 |
| 20 | 0.22 |
| 21 | 1.27 |
| 22 | 1.35 |
| 23 | 0.02 |
| 24 | 0.01 |
| 25 | 0.36 |
| 26 | 0.25 |

TABLE 1-continued

Potency of GLP-1 derivatives

| Compound of Example No. | Potency [$EC_{50}$/nM] |
|---|---|
| 27 | 0.05 |
| 28 | 0.08 |
| 29 | 0.10 |
| 30 | 0.21 |
| 31 | 0.04 |
| 32 | 0.46 |
| 33 | 0.06 |
| 34 | 1.27 |
| 35 | 0.74 |
| 36 | 0.14 |
| 37 | 0.34 |
| 38 | 0.07 |
| Liraglutide | 0.10 |
| Compound 135 | 4.00 |

As it is apparent from Table 1, very many of the GLP-1 derivatives are more potent than the prior art GLP-1 derivative of liraglutide (the lower the $EC_{50}$ value the better). All GLP-1 derivatives of the invention are much more potent than the Compound 135.

Example 41

Albumin Binding Affinity

The affinities of a number of GLP-1 derivatives of the invention for human serum albumin (HSA) were measured by a competition scintillation proximity assay (SPA) as described in the following.

Streptavidin-SPA beads (GE Healthcare RPNQ0009) were incubated with biotinylated HSA for 5 hours. The beads were washed with buffer to remove unbound HSA. The beads were mixed with a $^{125}$I-labeled acylated GLP-1 analogue (N-epsilon37-[2-(2-[2-((S)-4-((S)-4-(12-[4-(16-(1H-tetrazol-5-yl)hexadecanoylsulfamoyl)butyrylamino]dodecanoylamino)-4-carboxybutyrylamino)-4-carboxybutyrylamino)ethoxy]ethoxy)acetyl][Aib8,$^{125}$I-Tyr19,Glu22,Arg26,Arg34,Lys37] GLP-1(7-37)-$NH_2$) in a buffer containing 100 mM Hepes, 100 mM NaCl, 10 mM $MgSO_4$, 0.025% Tween-20, pH 7.4. The mixture was pipetted into the wells of a Perkin Elmer Optiplate-96 6005290 (100 µl per well) and 100 µl of a dilution series of the GLP-1 derivative to be measured was added in the same buffer. After 20 hours of gentle rocking at room temperature the plates were centrifuged and counted on a TopCounter. Bound cpm was plotted as a function of GLP-1 derivative concentration and the $EC_{50}$ value of the competition curve was used as a measure of the affinity of the derivative for HSA.

The albumin binding affinities ($EC_{50}$, in nM) of various GLP-1 derivatives of the invention are shown in Table 2 below.

TABLE 2

Albumin binding affinity

| Compound of Example No. | Albumin binding affinity ($EC_{50}$/nM) |
|---|---|
| 11, 26, 32 | 1-100 |
| 5, 13, 27, 33 | 100-150 |
| 14, 25, 37 | 150-200 |
| 2, 4, 6, 20, 28 | 200-400 |
| 1, 22, 29, 36 | 400-800 |
| 7, 9, 12, 35 | 800-1500 |
| 3, 8, 23, 24, 31 | 1500-2000 |
| 18, 21, 30, 34 | above 2000 |

As it is apparent from Table 2, several of the GLP-1 derivatives of the invention have a high albumin binding affinity corresponding to an $EC_{50}$ of below 2000 nM (the lower the $EC_{50}$, the higher the albumin binding affinity).

Example 42

Binding to the Extracellular Domain of the GLP-1 Receptor

For a number of GLP-1 derivatives of the invention (the compounds of Examples 1, 3, 4, 5, 6, 14, 15, 16, 17, 18, 19, 21, 22, 23, and 24), the affinity of the binding to the isolated N-terminal extracellular domain of the GLP-1R receptor (nGLP-1R) was measured as described below. Liraglutide was included for comparison.

The affinity is a measure of the ability of the GLP-1 derivative in question to displace $^{125}$I-Exendin-4(9-39) from binding to nGLP-1R, and the binding to nGLP-1R was measured in the following assay: The protein nGLP-1R was prepared as described by Runge et al 2007 (Biochemistry, vol. 46, pp. 5830-5840), biotinylated and immobilized on streptavidin-coated SPA beads. The nGLP1R in 0.1M $NaHCO_3$ was biotinylated using 75 µg BNHS (Sigma H1759) to 1 mg protein. The biotinylated nGLP1R was subsequently dialyzed against PBS. All reagents and derivatives were diluted in PBS with 0.05% v/v Tween 20. The binding assay was carried out in 96 well OptiPlates (PerkinElmer 6005290) in a final volume of 200 µl. Each well contained 2 mg streptavidin coated SPA beads (PerkinElmer RPNQ007), 0.1 pmol biotinylated nGLP1R, 50 pCi $^{125}$I-Exendin (9-39) and test peptide in final concentrations ranging from 1000 nM to 0.064 nM. The plates were incubated on a shaker at RT for 3 hours. The SPA particles were spun down by centrifugation for 10 min at 1500 rpm and the plates were counted in a TopCount-NXT (PerkinElmer).

The $IC_{50}$ value is read from the respective curve as the concentration of the GLP-1 derivative in question which displaces 50% of $^{125}$I-Exendin-4(9-39) from binding to nGLP-1R.

The affinity of liraglutide to nGLP-1R ($IC_{50}$) was determined to 1500 nM. The tested GLP-1 derivatives of the invention had affinities ranging from 2.0-276 (nM), with six compounds in the range of 2.0-10.0 nM. All tested GLP-1 derivatives of the invention accordingly exhibit an improved binding affinity to the N-terminal GLP-1 receptor, relative to liraglutide (the lower the $IC_{50}$ value, the better the binding).

Example 43

Dose-Response Study in db/db Mice

A number of GLP-1 derivatives of the invention (the compounds of Examples 1, 7, 8, 9, 11, 12, 13, 20, 22, and 27) were tested in a dose-response study in an obese, diabetic mouse model (db/db mice) as described in the following.

Fifty db/db mice (Taconic, Denmark), 10-12 weeks of age, were housed according to standard animal welfare rules of Novo Nordisk and were given free access to standard chow (e.g. Altromin 1324, Brogaarden, Gentofte, Denmark) and tap water and kept at 24° C. After 1 week of acclimatisation, the basal blood glucose was assessed twice. Based on the mean blood glucose values, 42 mice were selected for further experimentation and allocated to 7 groups (n=6) with matching blood glucose levels. The mice were used in experiments of 3-6 days' duration for up to 4 times, following which they were euthanized.

The seven groups received treatment as follows:
1: Vehicle, s.c.
2: GLP-1 derivative, 0.3 nmol/kg, s.c.
3: GLP-1 derivative, 1 nmol/kg, s.c.
4: GLP-1 derivative, 3 nmol/kg, s.c.
5: GLP-1 derivative, 10 nmol/kg, s.c.
6: GLP-1 derivative, 30 nmol/kg, s.c.
7: GLP-1 derivative, 100 nmol/kg, s.c.

Vehicle: 50 mM phosphate, 0.05% tween 80, pH 8. The GLP-1 derivative was dissolved in the vehicle, e.g. to concentrations of 0.05, 0.17, 0.5, 1.7, 5 and 17 nmol/ml and 300 microliter were administered s.c. per mouse weighing 50 g (6 ml/kg).

On the day of dosing, the compound in question was dosed at approximately 9 am (time 0). At time—½ h (8.30 am) blood glucose was assessed, following which the mice were weighed. Blood glucose was assessed several times on the day of dosing, usually at time 1, 3 and 6 h (10 am, 12 am and 3 pm).

On the following days, the blood glucose was assessed at time 24, 48, 72, and 96 h after dosing (i.e. at 9 am on day 2, 3, 4, 5), followed by weighing. In some studies, blood glucose and body weight was furthermore assessed 120 h (day 6) after dosing.

The mice were weighed individually on a digital weight.

Samples for the measurement of blood glucose were obtained from the tail tip capillary of conscious mice. Blood, 10 µl, was collected into heparinised capillaries and transferred to 500 µl glucose buffer (EBIO buffer solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

The half-lives (T½) were calculated according to the following mathematical model: Assuming that
(1) the disappearance of the compounds from plasma is monoexponential;
(2) the effect on blood glucose (deltaBG) can be described by a standard sigmoidal dose-response curve;
(3) the first 6 hours of absorption and distribution are ignored and only the return of the glucose from the bottom to the baseline (minimum to 0) is fitted;
then the glucose response (Y) (for example deltaBG) can be described by the following equation:

$$Y = Bottom + (Top - Bottom)/(1 + Dose^* \exp(-\ln 2^* t/T\frac{1}{2})/ED50),$$

where the variables ED50 and T½ are defined as follows:
ED50 is the dose giving rise to half maximal effect on BG (in nmol/kg)

T½ is the half-life (in hours); and the following are global Constants:
Top (the response after return to baseline glucose), and Bottom (the response at maximal glucose fall); and the following is a constant for each data set (each dose):
Dose (the administered dose (in nmol/kg)).
All data sets are fitted simultaneously.

All compounds tested had a half-life (T½) in the range of 10-30 hours.

Example 44

Alpha-Helix Content

The content of α-helical (alpha-helical) structure for a number of GLP-1 derivatives of the invention (the compounds of Examples 3, 4, 5, 7, 8, 9, 11, 12, 13, 14, 21, 22, and 24) was estimated using circular dichroism (CD) spectroscopy, as described below. Liraglutide was included in the test for comparative purposes.

Far-UV circular dichroism spectra were recorded on a Jasco 3-715 spectropolarimeter on 5 µM (uM, micro-Molar) peptide in 10 mM Tris/ClO$_4$ pH 8.0. Raw data were subtracted buffer background and normalised to molar elipticity in units of $M^{-1}$ $cm^{-1}$ based on the concentration of peptide bonds and the intensity value at 222 nm was extracted.

The intensity at 222 nm was used as a measure of alpha-helical content, i.e the signal is proportional to the alpha-helical content such that a value of $-1$ $M^{-1}$ $cm^{-1}$ corresponds to 10% of alpha-helical structure (Venyaminov and Yang 1996: "Determination of protein secondary structure" In Circular Dichroism and conformational analysis of biomolecules (Ed. Fasman GD, Plenum Press NY), pp. 69-108).

From the spectra, the values for the molar elipticity (Δε, or delta epsilon) were derived and the corresponding alpha-helical content estimated. The overall spectra features of the GLP-1 derivatives in the range of 200-250 nm are described by two bands with minima at 206 nm and 222 nm respectively. This is in accordance with a secondary structure with a significant alpha-helical stretch.

The value of delta epsilon at 222 nm for liraglutide in 5 uM concentration was below −3.6, corresponding to an alpha-helical content of liraglutide of below 36%.

The values of delta epsilon at 222 nm for the compounds of Examples 4, 5, 11, and 14 in 5 uM concentration were in the range of −2.0 to −3.6, corresponding to alpha-helical contents in the range of 20-36%.

The values of delta epsilon at 222 nm for the compounds of Examples 3, 7, 8, 9, 12, 13, 21, 22, and 24 in 5 uM concentration were in the range of −3.7 to −6.0, corresponding to alpha-helical contents in the range of 37-60%.

The invention claimed is:

1. A GLP-1 derivative which comprises a modified GLP-1(7-37) sequence having:
   i) a total of 3-12 amino acid modifications as compared to GLP-1(7-37) (SEQ ID No: 1), including
      a) a desamino-histidine residue at a position equivalent to position 7 of GLP-1 (7-37),
      b) a Glu residue at a position equivalent to position 22 of GLP-1(7-37), and
      c) an Arg residue at a position equivalent to position 26 of GLP-1(7-37); and
   ii) which is derivatised with an albumin binding residue or pegylated in a position selected from a position equivalent to position 18, 20, 23, 30, 31, 34, 36 or 37 of GLP-1(7-37).

2. The GLP-1 derivative according to claim 1, which comprises 3-8 amino acid substitutions as compared to GLP-1(7-37) (SEQ ID No: 1).

3. The GLP-1 derivative according to claim 1, which comprises 1-3 amino acid deletions as compared to GLP-1(7-37) (SEQ ID No: 1).

4. The GLP-1 derivative according to claim 1 which comprises 1-4 amino acid additions as compared to GLP-1(7-37) (SEQ ID No: 1).

5. The GLP-1 derivative according to claim 1, which comprises a non-natural amino acid at a position equivalent to position 8 of GLP-1(7-37) (SEQ ID No: 1).

6. The GLP-1 derivative according to claim 1, which has an Arg residue at a position equivalent to position 34 of GLP-1 (7-37) and which is derivatised with an albumin binding residue or pegylated in a position selected from a position equivalent to position 36 or 37 of GLP-1(7-37).

7. The GLP-1 derivative according to claim 1 having the sequence of formula (I):

```
Formula (I)
                                              (SEQ ID No: 2)
Xaa7-Xaa8-Xaa9-Gly-Thr-Phe-Thr-Ser-Asp-Xaa16-

Ser-Xaa18-Tyr-Xaa20-Glu-Glu-Xaa23-Xaa24-Xaa25-

Arg-Xaa27-Xaa28-Ile-Xaa30-Xaa31-Leu-Xaa33-Xaa34-

Xaa35-Xaa36-Xaa37-Xaa38-Xaa39-Xaa40-Xaa41-R
``` wherein ($Xaa_7$-$Xaa_8$) is (desamino-histidine-alanine), or (desamino-histidine-Aib);

$Xaa_9$ is Glu, or a Glu derivative;

$Xaa_{16}$ is Val, or Leu;

$Xaa_{18}$ is Ser, Lys, Cys, or Arg;

$Xaa_{20}$ is Leu, or Lys;

$Xaa_{23}$ is Gln, Glu, Lys, Cys, or Arg;

$Xaa_{24}$ is Ala, or Asn;

$Xaa_{25}$ is Ala, or Val;

Xaa$_{27}$ is Glu, Ala, or Leu;
Xaa$_{28}$ is Phe, or a Phe derivative;
Xaa$_{30}$ is Ala, Glu, Lys, or Arg;
Xaa$_{31}$ is Trp, Cys, or Lys;
Xaa$_{33}$ is Val, Cys, or Lys;
Xaa$_{34}$ is Lys, Cys, Glu, Asn, Dap, or Arg;
Xaa$_{35}$ is Gly, Arg, Lys, Aib, or absent;
Xaa$_{36}$ is Arg, Lys, or absent;
Xaa$_{37}$ is Gly, Aib, Cys, Lys, epsilon-amino-Lys, Pro, Arg, or absent;
Xaa$_{38}$ is Lys, Glu, Arg, or absent;
Xaa$_{39}$ is Lys, Arg, or absent;
Xaa$_{40}$ is Arg, or absent;
Xaa$_{41}$ is Arg, or absent; and
R is amide, or absent;
provided that if Xaa$_{37}$, Xaa$_{38}$, Xaa$_{39}$, or Xaa$_{40}$ is absent, then each amino acid residue downstream is also absent; and which is derivatised with an albumin binding residue or pegylated in a position selected from a position equivalent to position 18, 20, 23, 30, 31, 34, 36, 37, or 39 of GLP-1(7-37) (SEQ ID No: 1).

8. The GLP-1 derivative according to claim 7, which comprises 4-6 amino acid substitutions as compared to GLP-1(7-37) (SEQ ID No: 1).

9. The GLP-1 derivative according to claim 8, wherein Xaa$_{34}$ is Arg.

10. The GLP-1 derivative according to claim 9, which is derivatised with an albumin binding residue or pegylated in a position selected from a position equivalent to position 36 or 37 of GLP-1(7-37) (SEQ ID No: 1).

11. A GLP-1 derivative having the sequence of formula (II):

```
Formula (II)
                                        (SEQ ID No: 3)
Xaa₇-Xaa₈-Glu-Gly-Thr-Phe-Thr-Ser-Asp-Val-Ser- Xaa₁₈-Tyr-Leu-Glu-Glu-Gln-Ala-Ala-Arg-Glu-Phe- Ile-Xaa₃₀-Xaa₃₁-Leu-Xaa₃₃-Xaa₃₄-Xaa₃₅-Xaa₃₆-Xaa₃₇-

Xaa₃₈-Xaa₃₉-Xaa₄₀-Xaa₄₁-R
``` wherein
Xaa$_7$ is desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine, or 4-pyridylalanine;
Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{18}$ is Ser, Lys, or Arg;
Xaa$_{30}$ is Ala, Glu, Lys, or Arg;
Xaa$_{31}$ is Lys, or Trp;
Xaa$_{33}$ is Val, or Lys;
Xaa$_{34}$ is Lys, Glu, Dap, or Arg;
Xaa$_{35}$ is Gly, Arg, Lys, Aib, or absent;
Xaa$_{36}$ is Arg, Lys, or absent;
Xaa$_{37}$ is Gly, Aib, Lys, epsilon-amino-Lys, Pro, Arg, or absent;
Xaa$_{38}$ is Lys, Glu, Arg, or absent;
Xaa$_{39}$ is Lys, Arg, or absent;
Xaa$_{40}$ is Arg, or absent;
Xaa$_{41}$ is Arg, or absent; and
R is amide, or is absent;
provided that if Xaa$_{37}$, Xaa$_{38}$, Xaa$_{39}$, or Xaa$_{40}$ is absent, then each amino acid residue downstream is also absent; and which is derivatised with an albumin binding residue or pegylated in a position selected from a position equivalent to position 18, 20, 23, 30, 31, 34, 36, 37, or 39 of GLP-1(7-37) (SEQ ID No: 1).

12. The GLP-1 derivative according to claim 11, which comprises 4-6 amino acid substitutions as compared to GLP-1(7-37) (SEQ ID No: 1).

13. The GLP-1 derivative according to claim 12, wherein Xaa$_{34}$ is Arg.

14. The GLP-1 derivative according to claim 13, which is derivatised with an albumin binding residue or pegylated in a position selected from a position equivalent to position 36 or 37 of GLP-1(7-37) (SEQ ID No: 1).

15. The GLP-1 derivative according to claim 14, where in Xaa$_7$ is desamino-histidine.

16. A GLP-1 derivative which is selected from the following:
N-epsilon37{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis7,Glu22,Arg26,Arg34,Lys37]GLP-1(7-37)amide;
N-epsilon37-[2-(2-[2-(2-[2-(2-((R)-3-[1-(17-Carboxy-heptadecanoyl)piperidin-4-ylcarbonylamino]3-carboxypropionylamino)ethoxy)ethoxy]acetylamino)ethoxy]ethoxy)acetyl][DesaminoHis7,Glu22,Arg26,Arg34,Phe(m-CF3)28]GLP-1-(7-37)amide;
N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37)amide;
N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37);
N-epsilon37-[2-(2-{2-[2-(2-{2-[(S)-4-Carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Glu30,Arg34,Lys37]GLP-1-(7-37);
N-epsilon37-[2-(2-{2-[(S)-4-Carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][DesaminoHis7,Glu22,Arg26,Arg34,Lys37]GLP-1-(7-37)amide;
N-epsilon37 (Polyethyleneglycol2000)[DesaminoHis7,Glu22,Arg26,Arg34,Lys37]GLP-1 (7-37) amide;
N-epsilon37 (3-((2-(2-(2-(2-(2-Hexadecyloxyethoxy)ethoxy) ethoxy)ethoxy)ethoxy))propionyl)[DesaminoHis7,Glu22,Arg26,Arg34,Lys37]GLP-1(7-37)-amide;
N-epsilon37-{2-(2-(2-(2-[2-(2-(4-(hexadecanoylamino)-4-carboxybutyrylamino)ethoxy)ethoxy]acetyl)ethoxy)ethoxy)acetyl)}-[desaminoHis7,Glu22,Arg26, Glu30,Arg34,Lys37] (GLP-1-(7-37)amide
N-epsilon37-{2-(2-(2-(2-[2-(2-(4-(hexadecanoylamino)-4-carboxybutyrylamino)ethoxy)ethoxy]acetyl)ethoxy)ethoxy)acetyl)}-[desaminoHis7,Glu22, Arg26,Arg34, Lys 37] (GLP-1-(7-37))amide;
N-epsilon37-(2-(2-(2-(2-(2-(2-(2-(2-(Octadecanoylamino)ethoxy)ethoxy)acetylamino)ethoxy)ethoxy)

acetylamino)ethoxy)ethoxy)acetyl)[desaminoHis7, Glu22,Arg26,Arg34,Lys37] GLP-1 (7-37)amide N-epsilon37-[4-(16-(1H-Tetrazol-5-yl)hexadecanoylsulfamoyl)butyryl][DesaminoHis7,Glu22,Arg26,Arg34,Lys37]GLP-1-(7-37)amide;

N-epsilon37-[2-(2-{2-[2-(2-{2-[(S)-4-Carboxy-4-(19-carboxynonadecanoylamino)butyrylamino]ethoxy}ethoxy)acetylamino]ethoxy}ethoxy)acetyl][DesaminoHis7,Glu22,Arg26,Arg34,Lys37]GLP-1-(7-37);

N-epsilon37-(2-{2-[2-((S)-4-Carboxy-4-{(S)-4-carboxy-4-[(S)-4-carboxy-4-(19-carboxy-nonadecanoylamino)butyrylamino]butyrylamino}butyrylamino)ethoxy]ethoxy}acetyl)[DesaminoHis7,Glu22,Arg26,Arg34,Lys37]GLP-1-(7-37);

N-epsilon37-{2-[2-(2-{(S)-4-[(S)-4-(12-{4-[16-(2-tert-Butyl-2H-tetrazol-5-yl)-hexadecanoylsulfamoyl]butyrylamino}dodecanoylamino)-4-carboxybutyrylamino]-4-carboxybutyrylamino}ethoxy)ethoxy]acetyl}[DesaminoHis7,Glu22,Arg26,Arg34,Lys37]GLP-1 (7-37);

N-epsilon37-[2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl][desaminoHis7,Glu22,Arg26,Arg34,Lys37] GLP-1-(7-37);

N-epsilon36-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [desaminoHis7, Glu22,Arg26,Glu30,Arg34,Lys36]GLP-1-(7-37)-Glu-Lys peptide;

[desaminoHis7,Glu22,Arg26,Glu30,Arg34]GLP-1-(7-37)-Glu-Lys(2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl)peptide.

17. A pharmaceutical composition comprising a derivative according to claim 1 or a pharmaceutically acceptable salt, amide, alkyl, or ester thereof, and a pharmaceutically acceptable excipient.

18. A pharmaceutical composition comprising a derivative according to claim 11 or a pharmaceutically acceptable salt, amide, alkyl, or ester thereof, and a pharmaceutically acceptable excipient.

19. A pharmaceutical composition comprising a derivative according to claim 16 or a pharmaceutically acceptable salt, amide, alkyl, or ester thereof, and a pharmaceutically acceptable excipient.

20. A method of treating hyperglycemia, type 2 diabetes, impaired glucose tolerance, type 1 diabetes or obesity in a subject in need thereof, the method comprising to the subject a therapeutically effective amount of a pharmaceutical composition according to claim 17.

21. A method of treating hyperglycemia, type 2 diabetes, impaired glucose tolerance, type 1 diabetes or obesity in a subject in need thereof, the method comprising to the subject a therapeutically effective amount of a pharmaceutical composition according to claim 18.

22. A method of treating hyperglycemia, type 2 diabetes, impaired glucose tolerance, type 1 diabetes or obesity in a subject in need thereof, the method comprising to the subject a therapeutically effective amount of a pharmaceutical composition according to claim 19.

* * * * *

SEQUENCE LISTING

<160> NUMBER OF SEQ ID NOS: 3

<210> SEQ ID NO 1
<211> LENGTH: 31
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: Human GLP-1(7-37)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(35)
<220> FEATURE:
<221> NAME/KEY: MISC_FEATURE
<222> LOCATION: (1)..(2)
<223> OTHER INFORMATION: Xaa is (L-histidine-Aib), (desamino-histidine-
      alanine), or (desamino-Aib)
<220> FEATURE:
<221> NAME/KEY: MISC_FEATURE
<222> LOCATION: (3)..(3)
<223> OTHER INFORMATION: Xaa is Glu, or a Glu derivative
<220> FEATURE:
<221> NAME/KEY: MISC_FEATURE
<222> LOCATION: (10)..(10)
<223> OTHER INFORMATION: Xaa is Val, or Leu
<220> FEATURE:
<221> NAME/KEY: MISC_FEATURE
<222> LOCATION: (12)..(12)
<223> OTHER INFORMATION: Xaa is Ser, Lys, Cys, or Arg
<220> FEATURE:
<221> NAME/KEY: MISC_FEATURE
<222> LOCATION: (14)..(14)
<223> OTHER INFORMATION: Xaa is Leu, or Lys
<220> FEATURE:
<221> NAME/KEY: MISC_FEATURE
<222> LOCATION: (17)..(17)
<223> OTHER INFORMATION: Xaa is Gln, Glu, Lys, Cys, or Arg
<220> FEATURE:
<221> NAME/KEY: MISC_FEATURE
<222> LOCATION: (18)..(18)
<223> OTHER INFORMATION: Xaa is Ala, or Asn
<220> FEATURE:
<221> NAME/KEY: MISC_FEATURE
<222> LOCATION: (19)..(19)
<223> OTHER INFORMATION: Xaa is Ala, or Val
<220> FEATURE:
<221> NAME/KEY: MISC_FEATURE
<222> LOCATION: (21)..(21)
<223> OTHER INFORMATION: Xaa is Glu, Ala, or Leu
<220> FEATURE:
<221> NAME/KEY: MISC_FEATURE
<222> LOCATION: (22)..(22)
<223> OTHER INFORMATION: Xaa is Phe, or a Phe derivative
<220> FEATURE:
<221> NAME/KEY: MISC_FEATURE
<222> LOCATION: (24)..(24)
<223> OTHER INFORMATION: Xaa is Ala, Glu, Lys, or Arg
<220> FEATURE:
<221> NAME/KEY: MISC_FEATURE
<222> LOCATION: (25)..(25)
<223> OTHER INFORMATION: Xaa is Trp, Cys, or Lys
<220> FEATURE:
<221> NAME/KEY: MISC_FEATURE
<222> LOCATION: (27)..(27)
<223> OTHER INFORMATION: Xaa is Val, Cys, or Lys
<220> FEATURE:
<221> NAME/KEY: MISC_FEATURE
<222> LOCATION: (28)..(28)
<223> OTHER INFORMATION: Xaa is Lys, Cys, Glu, Asn, Dap, or Arg
<220> FEATURE:
<221> NAME/KEY: MISC_FEATURE
<222> LOCATION: (29)..(29)
<223> OTHER INFORMATION: Xaa is Gly, Arg, Lys, Aib, or absent
<220> FEATURE:
<221> NAME/KEY: MISC_FEATURE

```
<222> LOCATION: (30)..(30)
<223> OTHER INFORMATION: Xaa is Arg, Lys, or absent
<220> FEATURE:
<221> NAME/KEY: MISC_FEATURE
<222> LOCATION: (31)..(31)
<223> OTHER INFORMATION: Xaa is Gly, Aib, Cys, Lys, epsilon-amino-Lys,
      Pro, Arg, or absent
<220> FEATURE:
<221> NAME/KEY: MISC_FEATURE
<222> LOCATION: (32)..(32)
<223> OTHER INFORMATION: Xaa is Lys, Glu, Arg, or absent
<220> FEATURE:
<221> NAME/KEY: MISC_FEATURE
<222> LOCATION: (33)..(33)
<223> OTHER INFORMATION: Xaa is Lys, Arg, or absent
<220> FEATURE:
<221> NAME/KEY: MISC_FEATURE
<222> LOCATION: (34)..(34)
<223> OTHER INFORMATION: Xaa is Arg, or absent
<220> FEATURE:
<221> NAME/KEY: MISC_FEATURE
<222> LOCATION: (35)..(35)
<223> OTHER INFORMATION: Xaa is Arg, or absent

<400> SEQUENCE: 2

Xaa Xaa Xaa Gly Thr Phe Thr Ser Asp Xaa Ser Xaa Tyr Xaa Glu Glu
1               5                   10                  15

Xaa Xaa Xaa Arg Xaa Xaa Ile Xaa Xaa Leu Xaa Xaa Xaa Xaa Xaa Xaa
            20                  25                  30

Xaa Xaa Xaa
        35

<210> SEQ ID NO 3
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(35)
<220> FEATURE:
<221> NAME/KEY: MISC_FEATURE
<222> LOCATION: (1)..(1)
<223> OTHER INFORMATION: Xaa is L-histidine, D-histidine, desamino-
      histidine, 2-amino-histidine, beta-hydroxy-histidine,
      homohistidine, N-alpha-acetyl-histidine, alpha-fluoromethyl-
      histidine, alpha-methyl-histidine, 3-pyridylalanine,
      2-pyridylalanine, or 4-pyridylalanine
<220> FEATURE:
<221> NAME/KEY: MISC_FEATURE
<222> LOCATION: (2)..(2)
<223> OTHER INFORMATION: Xaa is Ala,Gly,Val,Leu,Ile,Lys,Aib,
      (1-aminocyclopropyl)carboxylic acid,
      (1-aminocyclobutyl)carboxylic acid,
      (1-aminocyclopentyl)carboxylic acid, (1-aminocyclohexyl)
      carboxylic acid, (1-aminocyclohexyl) carboxylic acid, (1-
      aminocycloheptyl) carboxylic acid, or (1-aminocyclooctyl)
      carboxylic acid
<220> FEATURE:
<221> NAME/KEY: MISC_FEATURE
<222> LOCATION: (12)..(12)
<223> OTHER INFORMATION: Xaa is Ser, Lys or Arg
<220> FEATURE:
<221> NAME/KEY: MISC_FEATURE
<222> LOCATION: (24)..(24)
<223> OTHER INFORMATION: Xaa is Ala, Glu, Lys, or Arg
<220> FEATURE:
<221> NAME/KEY: MISC_FEATURE
<222> LOCATION: (25)..(25)
<223> OTHER INFORMATION: Xaa is Lys or Trp
<220> FEATURE:
<221> NAME/KEY: MISC_FEATURE
<222> LOCATION: (27)..(27)
<223> OTHER INFORMATION: Xaa is Val, or Lys
```

```
<220> FEATURE:
<221> NAME/KEY: MISC_FEATURE
<222> LOCATION: (28)..(28)
<223> OTHER INFORMATION: Xaa is Lys, Glu, Dap, or Arg
<220> FEATURE:
<221> NAME/KEY: MISC_FEATURE
<222> LOCATION: (29)..(29)
<223> OTHER INFORMATION: Xaa is Gly, Arg, Lys, Aib, or absent
<220> FEATURE:
<221> NAME/KEY: MISC_FEATURE
<222> LOCATION: (30)..(30)
<223> OTHER INFORMATION: Xaa is Arg, Lys, or absent
<220> FEATURE:
<221> NAME/KEY: MISC_FEATURE
<222> LOCATION: (31)..(31)
<223> OTHER INFORMATION: Xaa is Gly, Aib, Lys, epsilon-amino-Lys, Pro,
      Arg, or absent
<220> FEATURE:
<221> NAME/KEY: MISC_FEATURE
<222> LOCATION: (32)..(32)
<223> OTHER INFORMATION: Xaa is Lys, Glu, Arg, or absent
<220> FEATURE:
<221> NAME/KEY: MISC_FEATURE
<222> LOCATION: (33)..(33)
<223> OTHER INFORMATION: Xaa is Lys, Arg, or absent
<220> FEATURE:
<221> NAME/KEY: MISC_FEATURE
<222> LOCATION: (34)..(34)
<223> OTHER INFORMATION: Xaa is Arg, or absent
<220> FEATURE:
<221> NAME/KEY: MISC_FEATURE
<222> LOCATION: (35)..(35)
<223> OTHER INFORMATION: Xaa is Arg, or absent

<400> SEQUENCE: 3

Xaa Xaa Glu Gly Thr Phe Thr Ser Asp Val Ser Xaa Tyr Leu Glu Glu
1               5                   10                  15

Gln Ala Ala Arg Glu Phe Ile Xaa Xaa Leu Xaa Xaa Xaa Xaa Xaa Xaa
            20                  25                  30

Xaa Xaa Xaa
        35
```